(12) United States Patent
Corvey et al.

(10) Patent No.: US 9,234,039 B2
(45) Date of Patent: Jan. 12, 2016

(54) PEPTIDE OR PEPTIDE COMPLEX BINDING TO ALPHA2 INTEGRIN AND METHODS AND USES INVOLVING THE SAME

(75) Inventors: Carsten Corvey, Frankfurt am Main (DE); Horst Blum, Frankfurt am Main (DE); Béatrice Cameron, Paris (FR); Tarik Dabdoubi, Paris (FR); Stephanie Decary, Paris (FR); Nicolas Baurin, Paris (FR); David Papin, Paris (FR); Christian Lange, Frankfurt am Main (DE)

(73) Assignee: SANOFI, Paris (FR)

( * ) Notice: Subject to any disclaimer, the term of this patent is extended or adjusted under 35 U.S.C. 154(b) by 66 days.

(21) Appl. No.: 13/819,620

(22) PCT Filed: Aug. 30, 2011

(86) PCT No.: PCT/EP2011/064926
§ 371 (c)(1),
(2), (4) Date: Feb. 27, 2013

(87) PCT Pub. No.: WO2012/028622
PCT Pub. Date: Mar. 8, 2012

(65) Prior Publication Data
US 2013/0156786 A1    Jun. 20, 2013

(30) Foreign Application Priority Data

Aug. 31, 2010   (EP) .................................... 10305929

(51) Int. Cl.
| | | |
|---|---|---|
| A61K 39/00 | (2006.01) | |
| A61K 39/395 | (2006.01) | |
| C07K 16/28 | (2006.01) | |
| G01N 33/68 | (2006.01) | |

(52) U.S. Cl.
CPC ........ *C07K 16/2839* (2013.01); *G01N 33/6857* (2013.01); *C07K 2317/24* (2013.01); *C07K 2317/33* (2013.01); *C07K 2317/55* (2013.01); *C07K 2317/567* (2013.01); *C07K 2317/76* (2013.01); *C07K 2317/92* (2013.01); *C07K 2317/94* (2013.01); *G01N 2333/70546* (2013.01)

(58) Field of Classification Search
None
See application file for complete search history.

(56) References Cited

U.S. PATENT DOCUMENTS

| | | | |
|---|---|---|---|
| 5,939,598 A | 8/1999 | Kucherlapati | |
| 6,136,310 A * | 10/2000 | Hanna et al. ............... | 424/154.1 |
| 6,291,196 B1 * | 9/2001 | Vielkind ...................... | 435/7.23 |
| 6,737,056 B1 | 5/2004 | Presta | |
| 7,700,321 B2 | 4/2010 | McPherson et al. | |
| 2003/0118592 A1 | 6/2003 | Ledbetter et al. | |
| 2003/0133939 A1 | 7/2003 | Ledbetter | |
| 2004/0228856 A1 | 11/2004 | Presta | |
| 2005/0281828 A1 | 12/2005 | Bowdish et al. | |
| 2007/0128190 A1 | 6/2007 | Lazarides et al. | |
| 2007/0141052 A1 | 6/2007 | Watkins et al. | |
| 2008/0138349 A1 | 6/2008 | Stavenhagen | |
| 2009/0004186 A1 | 1/2009 | Shitara et al. | |
| 2010/0047243 A1 | 2/2010 | Burden et al. | |
| 2010/0215651 A1 | 8/2010 | Blein et al. | |
| 2011/0059075 A1 | 3/2011 | Wittrup et al. | |
| 2012/0100140 A1 | 4/2012 | Reyes | |

FOREIGN PATENT DOCUMENTS

| | | |
|---|---|---|
| CA | 2676529 A1 | 7/2008 |
| KR | 2008074184 A | 8/2008 |
| KR | 2009114449 A | 11/2009 |
| WO | 9954342 A1 | 10/1999 |
| WO | 0042072 A2 | 7/2000 |
| WO | 2005103081 A2 | 11/2005 |
| WO | 2006105338 A2 | 10/2006 |
| WO | 2007041635 A2 | 4/2007 |
| WO | 2007044616 A2 | 4/2007 |
| WO | 2007056858 A1 | 5/2007 |
| WO | 2007106915 A2 | 9/2007 |
| WO | 2008090959 A1 | 7/2008 |
| WO | 2008114011 A2 | 9/2008 |
| WO | 2009032661 A1 | 3/2009 |
| WO | 2010052556 A1 | 5/2010 |
| WO | 2010095270 A1 | 8/2010 |
| WO | 2011005481 A1 | 1/2011 |
| WO | 2011091078 A2 | 7/2011 |

OTHER PUBLICATIONS

ABCAM Product Datasheet. Anti-Integrin alpha 2 antibody [AK7] (FITC) ab30486. pp. 1-2, Sep. 8, 2014.*
Londrigan et al. Monkey Rotavirus Binding to α2β1 Integrin Requires the α2βI Domain and is Facilitated by the Homologous β1 Subunit. Journal of Virology, Sep. 2003, p. 9486-9501.*
Jarvis et al. Distinct roles of GPVI and integrin α2β1 in platelet shape change and aggregation induced by different collagens. Br J Pharmacol. Sep. 2002; 137(1): 107-117.*
Smith et al. Mapping the Collagen-binding Site in the I Domain of the Glycoprotein Ia/IIa (Integrin α2β1. The Journal of Biological Chemistry vol. 275, No. 6, Issue of Feb. 11, pp. 4205-4209, 2000.*
Klimka et al.,Human anti-CD30 recombinant antibodies by guided phage antibody selection using cell panning. British Journal of Cancer (2000) 83:252-260.*
Beiboer et al., Guided selection of a pan carcinoma specific antibody reveals similar binding characteristics yet structural divergence between the original murine antibody and its human equivalent. J. Mol. Biol. 296: 833-849 (2000).*
Almagro, Juan C., and Johan Fransson. "Humanization of antibodies." Front Biosci 13 (2008): 1619-1633.

(Continued)

*Primary Examiner* — Maher Haddad
(74) *Attorney, Agent, or Firm* — Lathrop & Gage LLP; James H. Velema, Esq.

(57) ABSTRACT

The present invention relates to a peptide or peptide complex binding to α2 integrin, to one or more nucleic acid(s) coding for the peptide or peptide complex, a recombinant cell producing the peptide or peptide complex, a method for producing the peptide or peptide complex, a pharmaceutical composition comprising the peptide or peptide complex or the nucleic acid(s) for use as a medicament, a method for detecting α2 integrin and a screening method.

17 Claims, 22 Drawing Sheets

(56) References Cited

OTHER PUBLICATIONS

Ward, E. Sally, et al. "Binding activities of a repertoire of single immunoglobulin variable domains secreted from *Escherichia coli*." Nature 341.6242 (1989): 544-546.

Vajdos, Felix F., et al. "Comprehensive functional maps of the antigen-binding site of an anti-ErbB2 antibody obtained with shotgun scanning mutagenesis."Journal of molecular biology 320.2 (2002): 415-428.

Bird, Robert E., et al. "Single-chain antigen-binding proteins." Science 242.4877 (1988): 423-426.

Durocher, Yves, Sylvie Perret, and Amine Kamen. "High-level and high-throughput recombinant protein production by transient transfection of suspension-growing human 293-EBNA1 cells." Nucleic acids research 30.2 (2002): e9-e9.

Gonnet, Gaston H., Mark A. Cohen, and Steven A. Benner. "Exhaustive matching of the entire protein sequence database." Science 256.5062 (1992): 1443-1445.

Heap, Caroline J., et al. "Analysis of a 17-amino acid residue, virus-neutralizing microantibody." Journal of general virology 86.6 (2005): 1791-1800.

Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.

Holliger, Philipp, Terence Prospero, and Greg Winter. ""Diabodies": small bivalent and bispecific antibody fragments." Proceedings of the National Academy of Sciences 90.14 (1993): 6444-6448.

Marks, James D., et al. "By-Passing Immunization: Building High Affinity Human Antibodies by Chain Shuffling." Nature Biotechnology 10.7 (1992): 779-783.

Padlan, Eduardo A., C. Abergel, and J. P. Tipper. "Identification of specificity-determining residues in antibodies." The FASEB journal 9.1 (1995): 133-139.

Sazinsky, Stephen L, Engineering aglycosylated antibody variants with immune effector functions. Massachusetts Institute of Technology. Dept. of Biological Engineering. Dissertation, 2008, pp. 1-114.

Kriegelstein et al., "Collagen-binding integrin $\alpha$ 1 $\beta$ 1 regulates intestinal inflammation in experimental colitis", J. Clin.Invest. 110(12):1773-82 (2002).

De Fougerolles el. al., "Regulation of inflammation by collagen-binding integrins $\alpha$ 1 $\beta$ 1 and $\alpha$ 2 $\beta$ 1 in models of hypersensitivity and arthritis", J. Clin. Invest., 105:721-729 (2000).

Senger et al., "The $\alpha$ 1 $\beta$ 1 and $\alpha$ 2 $\beta$ 1 Integrins Provide Critical Support for Vascular Endothelial Growth Factor Signaling, Endothelial Cell Migration, and Tumor Angiogenesis", Am. J. Pathol., 160(1):195-204 (2002).

Vanhoorelbeke et al., "Inhibition of Platelet Adhesion to Collagen as a New Target for Antithrombolic Drugs", Curr. Drug Targets Cardiovasc. Haematol. Disord., 3(2)125-40 (2003).

Bhatt and Topol, "Scientific and Therapeutic Advances in Antiplatelet Therapy", Nat. Rev. Drug Discov., 2 (1):15-28 (2003).

Takada and Hemler, "The Primary Structure of the VLA-2/Collagen Receptor a2 Subunit (Platelet GPia): Homology to Other Integrins and the Presence of a Possible Collagen-binding Domain", J. Cell Biol., vol. 109, pp. 397-407, (1989).

Argraves, W.S, "Amino Acid Sequence of the Human Fibronectin Receptor," J. Cell. Biol. Sep 105(3):1183-90, (1987).

Kamata et al., "Identification of Putative Ligand Binding Sites within I Domain of Integrin $\alpha$ 2 $\beta$ 1(VLA-2, CD49b/CD29), J. Biol.Chem.", vol. 269, No. 13, pp. 9659-9663 (1994).

Schumaker, et al., "Ultracentrifuge Studies of the Binding of IgG of Different Subclasses to the Clq Subunit of the First Component of Complement", Biochemistry, 15:5175-81, (1976).

Idusogie et al., "Mapping of the C1q Binding Site on Rituxan, a Chimeric Antibody with a Human IgG1 Fc", J. Immunol. Methods, 164:4178-4184, (2000).

Hangan et al., "Integrin VLA-2 (a2b1) Function in Postextravasation Movement of Human Rhabdomyosarcoma RD Cells in the Liver", Cancer Res. 56:3142-3149 (1996).

Nieswandt and Watson, "Platelet-collagen interaction: is GPVI the central receptor?", Blood 102(2):449-461 (2003).

Emsley et al., "Crystal Structure of the I Domain from Integrin $\alpha$ 1 $\beta$ 1", J. Biol. Chem., vol. 272, No. 45, 28512-28517, (1997).

Natsume et al., Engineered antibodies of the IgG1/IgG3 mixed isotype with enhanced cytotoxic activities, Cancer Research, vol. 68, No. 10, pp. 3863-3872, (2008).

Umana, et al., "Novel 3(rd) generation humanized type IICD20 antibody with glycoengineered fc and modified elbow hinge for enhanced ADCC and superior apoptosis induction.", Blood, vol. 108, No. 11, Part 1, p. 72A, (Abstract of Oral Sessions) (2006).

International Search Report and Written Opinion in related application PCT/IB11/00344, 21 pages, Sep. 28, 2011.

Hughes et al. 'Platelet integrin alpha2 I-domain specific antibodies produced via domain specific DNA vaccination combined with variable gene phage display.' Thrombosis and Haemostasis-Stuttgart 2005, vol. 94, No. 5, pp. 1318.

Schoolmeester et al. 'Monoclonal antibody IAC-1 is specific for activated $\alpha$2$\beta$1 and binds to amino acids 199 to 201 of the integrin $\alpha$2 I-domain.' Blood. 2004, vol. 104, No. 2, pp. 390-396.

International Search Report for International Application No. PCT/EP2011/064926, dated May 16, 2012 (8 pages).

Written Opinion of the International Searching Authority for International Application No. PCT/EP2011/064926, dated Feb. 28, 2013 ( 13 pages).

Winkler et al. 'Changing the antigen binding specificity by single point mutations of an anti-p24 (HIV-1) antibody.' The Journal of Immunology. 2000, vol. 165, No. 8, pp. 4505-4514.

Brown et al. 'Tolerance of single, but not multiple, amino acid replacements in antibody VH CDR 2: a means of minimizing B cell wastage from somatic hypermutation?.' 1996, The Journal of immunology, vol. 156, No. 9, pp. 3285-3291.

\* cited by examiner

| Parameter+ | Estimate | SD | CV(%) | 95%CI |
|---|---|---|---|---|
| KD (nM) | 0.2146 | 0.01291 | 6.0 | [0.1899 ; 0.2425] |

Fig.4
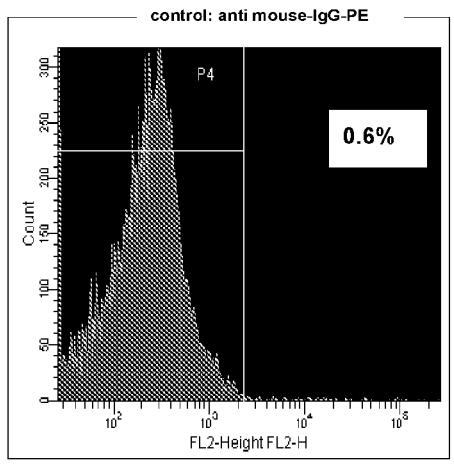
Figure 4a
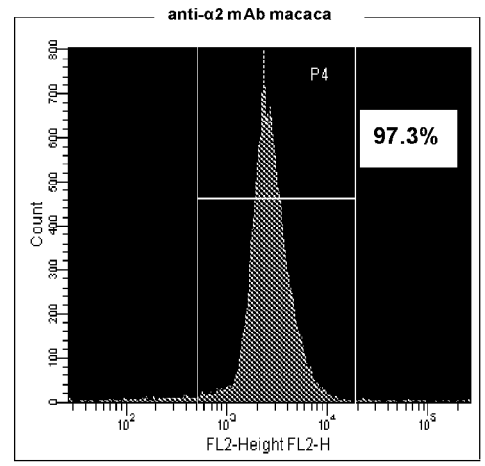
Figure 4b
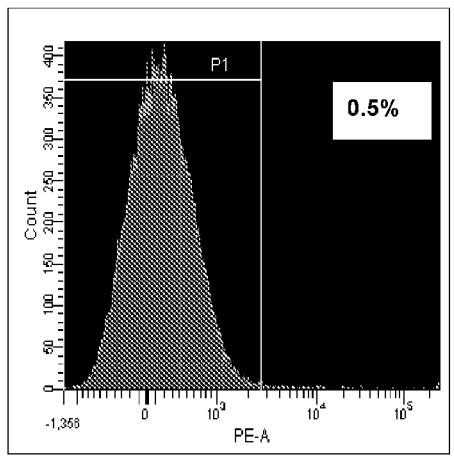
Figure 4c
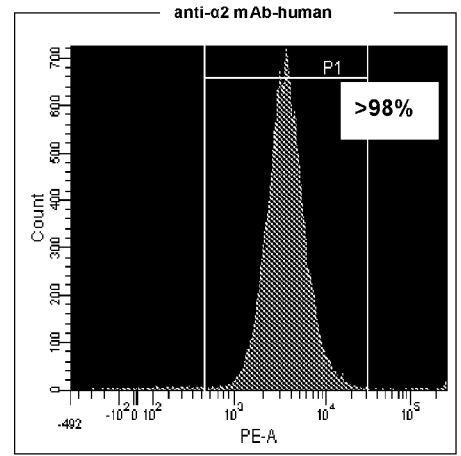
Figure 4d

Fig.5

Fig. 5a) Light chain variable domain of the anti-α2-integrin mAb

NIVLTQSPAS LAVSLGQRAT ISCRASESVE SYGNSFIYWY QQKPGQAPKL LIYLASNLAS GVPARFSGSG
SRTDFTLTID PVEADDAATY YCQQNNEDPY TFGGGTKLEI K (SEQ ID NO:1)

AACATTGTGCTGACCCAATCTCCAGCTTCTTTGGCTGTGTCTCTAGGGCAGAGGGCCACCATATCCTGCAGAGCCAG
TGAAAGTGTTGAGAGTTATGGCAACAGTTTTATTTACTGGTACCAGCAGAAACCAGGACAGGCACCCAAACTCCTCA
TCTATCTTGCATCCAACCTAGCATCTGGGGTCCCTGCCAGGTTCAGTGGCAGTGGGTCTAGGACAGACTTCACCCTC
ACCATTGATCCTGTGGAGGCTGATGATGCTGCAACCTATTACTGTCAGCAAAATAATGAGGATCCGTACACGTTCGG
AGGGGGGACCAAGCTGGAAATAAAA (SEQ ID NO:12)

Fig. 5b) Heavy chain variable domain the anti-α2-integrin mAb

QVQLHQPGAE LVKPGAPVKL SCKASGYTFT SYWMNWVKQR PGPGLEWIGR IDPSDSETHY NQKFKDKATL
TVDKSSSTAY IQLSSLTSED SAVYYCAKVG RGYFDYWGQG TTLTVSS (SEQ ID NO:2)

CAGGTCCAACTGCATCAGCCTGGGGCTGAACTTGTGAAGCCTGGGGCTCCAGTGAAGCTGTCCTGCAAGGCTTCTGG
CTACACCTTCACCAGCTACTGGATGAACTGGGTGAAGCAGAGGCCTGGACGAGGCCTCGAGTGGATTGGCAGGATTG
ATCCTTCCGATAGTGAAACTCACTACAATCAAAAGTTCAAGGACAAGGCCACACTGACTGTAGACAAATCCTCCAGC
ACAGCCTACATCCAACTCAGCAGCCTGACATCTGAGGACTCTGCGGTCTATTACTGTGCAAAGGTGGGACGGGGGTA
CTTTGACTACTGGGGCCAAGGCACCACTCTCACAGTCTCCTCA (SEQ ID NO:13)

Fig.6

Fig. 6a: CDRs of the heavy chain variable domain

HCDR1
GYTFTSYWMN (SEQ ID NO:3)

HCDR2
RIDPSDSETHYNQKFK (SEQ ID NO:4)

HCDR3
VGRGYFDY (SEQ ID NO:5)

Figure 6b: CDRs of the light chain variable domain

LCDR1:
RASESVESYGNSFIY (SEQ ID NO: 6)

LCDR2:
LASNLAS (SEQ ID NO: 7)

LCDR3:
QQNNEDPYT (SEQ ID NO: 8)

Fig.7

Fig. 7a: chimeric (anti alpha 2VL-IGKC CL) Light Chain

```
NIVLTQSPASLAVSLGQRATISCRASESVESYGNSFIYWYQQKPGQAPKLLIYLASNLASGVPA
RFSGSGSRTDFTLTIDPVEADDAATYYCQQNNEDPYTFGGGTKLEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
```

(Amino Acid Sequence: SEQ ID NO:9)

```
AACATTGTGCTGACCCAATCTCCAGCTTCTTTGGCTGTGTCTCTAGGGCAGAGGGCCACCATATCCTGCAGAGCCAG
TGAAAGTGTTGAGAGTTATGGCAACAGTTTTATTTACTGGTACCAGCAGAAACCAGGACAGGCACCCAAACTCCTCA
TCTATCTTGCATCCAACCTAGCATCTGGGGTCCCTGCCAGGTTCAGTGGCAGTGGGTCTAGGACAGACTTCACCCTC
ACCATTGATCCTGTGGAGGCTGATGATGCTGCAACCTATTACTGTCAGCAAAATAATGAGGATCCGTACACGTTCGG
AGGGGGGACCAAGCTGGAAATAAAACGTACGGTGCCGCTCCTTCCGTGTTCATCTTCCCTCCCTCCGACGAGCAGC
TGAAGTCCGGCACCGCCTCCGTGGTGTGTCTGCTGAACAACTTCTACCCTCGGGAGGCCAAGGTGCAGTGGAAGGTG
GACAACGCCCTGCAGTCCGGCAACTCCCAGGAGTCCGTCACCGAGCAGGACTCCAAGGACAGCACCTACTCCCTGTC
CTCCACCCTGACCCTGTCCAAGGCCGACTACGAGAAGCACAAGGTGTACGCCTGTGAGGTGACCCACCAGGGCCTGT
CCAGCCCTGTGACCAAGTCCTTCAACCGGGGCGAGTGC
```

(coding Sequence: SEQ ID NO:14)

Fig.7b: Chimeric (anti α2 VH-IGHG4 CH1) mAb

```
QVQLHQPGAELVKPGAPVKLSCKASGYTFTSYWMNWVKQRPGRGLEWIGRIDPSDSETHYNQKF
KDKATLTVDKSSSTAYIQLSSLTSEDSAVYYCAKVGRGYFDYWGQGTTLTVSSASTKGPSVFPL
APCSRSTSESTAALGCLVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLFPPKPKDTLMISRTPEV
TCVVVDVSQEDPEVQFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSLSLSLG
```

(Amino Acid Sequence: SEQ ID NO:10)

```
CAGGTCCAACTGCATCAGCCTGGGGCTGAACTTGTGAAGCCTGGGGCTCCAGTGAAGCTGTCCTGCAAGGCTTCTGG
CTACACCTTCACCAGCTACTGGATGAACTGGGTGAAGCAGAGGCCTGGACGAGGCCTCGAGTGGATTGGCAGGATTG
```

Fig. 7b (cont.)

```
ATCCTTCCGATAGTGAAACTCACTACAATCAAAAGTTCAAGGACAAGGCCACACTGACTGTAGACAAATCCTCCAGC
ACAGCCTACATCCAACTCAGCAGCCTGACATCTGAGGACTCTGCGGTCTATTACTGTGCAAAGGTGGGACGGGGGTA
CTTTGACTACTGGGGCCAAGGCACCACTCTCACAGTCTCCTCAGCCAGCACCAAGGGCCCTTCCGTGTTCCCTCTGG
CCCCTTGCTCCCGGTCCACCTCCGAGTCCACCGCCGCTCTGGGCTGCCTGGTGAAGGACTACTTCCCTGAGCCTGTG
ACCGTGTCCTGGAACTCTGGCGCCCTGACCTCCGGCGTGCACACCTTCCCTGCCGTGCTGCAGTCCTCCGGCCTGTA
CTCCCTGTCCTCCGTGGTGACCGTGCCTTCCTCCTCCCTGGGCACCAAGACCTACACCTGTAACGTGGACCACAAGC
CTTCCAACACCAAGGTGGACAAGCGGGTGGAGTCCAAGTACGGCCCTCCTTGCCCTCCCTGCCCTGCCCCTGAGTTC
GAGGGCGGACCTAGCGTGTTCCTGTTCCCTCCTAAGCCTAAGGACACCCTGATGATCTCCCGGACCCCTGAGGTGAC
CTGTGTGGTGGTGGACGTGTCCCAGGAGGACCCTGAGGTCCAGTTCAACTGGTACGTGGACGGCGTGGAGGTGCACA
ACGCCAAGACCAAGCCTCGGGAGGAGCAGTTCAATTCCACCTACCGGGTGGTGTCTGTGCTGACCGTGCTGCACCAG
GACTGGCTGAACGGCAAAGAATACAAGTGTAAGGTCTCCAACAAGGGCCTGCCCTCCTCCATCGAGAAACCATCTC
CAAGGCCAAGGGCCAGCCTAGGGAGCCTCAGGTGTACACCCTGCCTCCTAGCCAGGAAGAGATGACCAAGAACCAGG
TGTCCCTGACCTGTCTGGTGAAGGGCTTCTACCCTTCCGACATCGCCGTGGAGTGGGAGTCCAACGGCCAGCCTGAG
AACAACTACAAGACCACCCCTCCTGTGCTGGACTCCGACGGCTCCTTCTTCCTGTACTCCAGGCTGACCGTGGACAA
GTCCCGGTGGCAGGAGGGCAACGTCTTTTCCTGCTCCGTGATGCACGAGGCCCTGCACAACCACTACACCCAGAAGT
CCCTGTCCCTGTCTCTGGGC
```

(coding Sequence: SEQ ID NO:15)

Fig. 7c: Chimeric (anti α2 VH-IGHG1 CH1) heavy chain Fab fragment

```
QVQLHQPGAELVKPGAPVKLSCKASGYTFTSYWMNWVKQRPGRGLEWIGRIDPSDSETHYNQKF
KDKATLTVDKSSSTAYIQLSSLTSEDSAVYYCAKVGRGYFDYWGQGTTLTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHT*HHHHHH*
```

(Amino Acid Sequence: SEQ ID NO:11)

```
CAGGTCCAACTGCATCAGCCTGGGGCTGAACTTGTGAAGCCTGGGGCTCCAGTGAAGCTGTCCTGCAAGGCTTCTGG
CTACACCTTCACCAGCTACTGGATGAACTGGGTGAAGCAGAGGCCTGGACGAGGCCTCGAGTGGATTGGCAGGATTG
ATCCTTCCGATAGTGAAACTCACTACAATCAAAAGTTCAAGGACAAGGCCACACTGACTGTAGACAAATCCTCCAGC
ACAGCCTACATCCAACTCAGCAGCCTGACATCTGAGGACTCTGCGGTCTATTACTGTGCAAAGGTGGGACGGGGGTA
CTTTGACTACTGGGGCCAAGGCACCACTCTCACAGTCTCCTCAGCCAGCACCAAGGGCCCATCCGTGTTCCCTCTGG
CCCCTTCCTCCAAGTCCACCTCCGGCGGCACCGCCGCTCTGGGCTGCCTGGTGAAGGACTACTTCCCTGAGCCTGTG
ACCGTGTCCTGGAACTCTGGCGCCCTGACCAGCGGCGTGCACACCTTCCCTGCCGTGCTGCAGTCCTCCGGCCTGTA
CTCCCTGTCCTCCGTGGTGACCGTGCCTTCCTCCTCCCTGGGCACCCAGACCTACATCTGTAACGTGAACCACAAGC
CCTCCAACACCAAGGTGGACAAGAAGGTGGAGCCTAAGTCCTGTGACAAGACCCACACCCATCACCATCACCATCAC
```

(coding Sequence: SEQ ID NO:16)

Fig.8

Human constant regions for generation of chimeric antibody constructs

Swiss-Prot: Q502W4

>gi|74740177|sp|Q502W4|Q502W4_HUMAN IGKC protein
RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC (Amino Acid Sequence: SEQ ID NO:17)

Swiss-Prot: P01861.1 (S108P, L115E)

>gi|121047|sp|P01861.1|IGHG4_HUMAN RecName: Full=Ig gamma-4 chain C region
ASTKGPSVFPLAPCSRSTSESTAALGCLVKDYFPEPVTVSWNSGALTSGVHTFPAVLQSSGLYSLSSVVTVPSSSLG
TKTYTCNVDHKPSNTKVDKRVESKYGPPCPPCPAPEFEGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSSIEKTISKAKGQPREPQVYTL
PPSQEEMTKNQVSLTCLVKGFYPSDIAVEWESNGQPENNYKTTPPVLDSDGSFFLYSRLTVDKSRWQEGNVFSCSVM
HEALHNHYTQKSLSLSLGK (Amino Acid Sequence: SEQ ID NO:18)

Swiss-Prot: Q569F4

>gi|74735951|sp|Q569F4|Q569F4_HUMAN IGHG1 protein
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPGK (Amino Acid Sequence: SEQ ID NO:19)

Fig.9

Human α2 and β1 integrin sequences

α2 integrin precursor according to accession No: NP_002194.2:

```
   1 mgpertgaap lplllvlals qgilncclay nvglpeakif sgpsseqfgy avqqfinpkg
  61 nwllvgspws gfpenrmgdv ykcpvdlsta tceklnlqts tsipnvtemk tnmslglilt
 121 rnmgtggflt cgplwaqqcg nqyyttgvcs dispdfqlsa sfspatqpcp slidvvvvcd
 181 esnsiypwda vknflekfvq gldigptktq vgliqyannp rvvfnlntyk tkeemivats
 241 qtsqygqdlt ntfgaiqyar kyaysaasgg rrsatkvmvv vtdgeshdgs mlkavidqcn
 301 hdnilrfgia vlgylnrnal dlknlikeik aiasioLery ffnvsdeaal lekagtlgeq
 361 ifsiegtvqg gdnfqmemsq vgfsadyssq ndilmlgavg afgwsgtivq ktshghlifp
 421 kqafdqilqd rnhssylgys vaaistgest hfvagapran ytgqivlysv nengnitviq
 481 ahrgdqigsy fgsvlcsvdv dkdtitdvll vgapmymsdl kkeegrvylf tikegilgqh
 541 qflegpegie ntrfgsaiaa lsdinmdgfn dvivgsplen qnsgavyiyn ghqgtirtky
 601 sqkilgsdga frshlqyfgr sldgygdlng dsitdvsiga fgqvvqlwsq siadvaieas
 661 ftpekitlvn knaqiilklc fsakfrptkq nnqvaivyni tldadgfssr vtsrglfken
 721 nerclqknmv vnqaqscpeh iiyiqepsdv vnsldlrvdi slenpgLspa leaysetakv
 781 fsipfhkdcg edglcisdlv ldvrqipaaq eqpfivsnqn krltfsvtlk nkresayntg
 841 ivvdfsenlf fasfslpvdg tevtcqvaas qksvacdvgy palkreqqvt ftinfdfnlq
 901 nlqnqaslsf qalsesqeen kadnlvnlki pllydaeihl trstninfye issdgnvpsi
 961 vhsfedvgpk fifslkvttg svpvsmatvi ihipqyLkek nplmylLgvq tdkagdiscn
1021 adinplkigq tsssvsfkse nfrhtkelnc rtascsnvtc wlkdvhmkge yfvnvttriw
1081 ngtfasstfq tvqltaaaei ntynpeiyvi edntvtiplm imkpdekaev ptgviigsii
1141 agillllalv ailwklgffk rkyekmtknp deidettels s
                                                    (SEQ ID NO:20)
```

α2 integrin coding sequence (hs) according to NCBI accession No: NM_002203.3:

Fig. 9 (cont.)

```
   1 atggggccag aacggacagg ggccgcgccg ctgccgctgc tgctggtgtt agcgctcagt
  61 caaggcattt taaattgttg tttggcctac aatgttggtc tcccagaagc aaaaatattt
 121 tccggtcctt caagtgaaca gtttggctat gcagtgcagc agtttataaa tccaaaaggc
 181 aactggttac tggttggttc accctggagt ggctttcctg agaaccgaat gggagatgtg
 241 tataaatgtc ctgttgacct atccactgcc acatgtgaaa aactaaattt gcaaacttca
 301 acaagcattc caaatgttac tgagatgaaa accaacatga gcctcggctt gatcctcacc
 361 aggaacatgg gaactggagg ttttctcaca tgtggtcctc tgtgggcaca gcaatgtggg
 421 aatcagtatt acacaacggg tgtgtgttct gacatcagtc ctgattttca gctctcagcc
 481 agcttctcac ctgcaactca gccctgccct tccctcatag atgttgtggt tgtgtgtgat
 541 gaatcaaata gtatttatcc ttgggatgca gtaaagaatt ttttggaaaa atttgtacaa
 601 ggcctggata taggccccac aaagacacag gtggggttaa ttcagtatgc caataatcca
 661 agagttgtgt ttaacttgaa cacatataaa accaagaag aaatgattgt agcaacatcc
 721 cagacatccc aatatggtgg ggacctcaca aacacattcg gagcaattca atatgcaaga
 781 aaatatgctt attcagcagc ttctggtggg cgacgaagtg ctacgaaagt aatggtagtt
 841 gtaactgacg gtgaatcaca tgatggttca atgttgaaag ctgtgattga tcaatgcaac
 901 catgacaata tactgaggtt tggcatagca gttcttgggt acttaaacag aaacgccctt
 961 gatactaaaa atttaataaa agaataaaa gcaatcgcta gtattccaac agaaagatac
1021 ttttcaatg tgtctgatga agcagctcta ctagaaaagg ctgggacatt aggagaacaa
1081 attttcagca ttgaaggtac tgttcaagga ggagacaact ttcagatgga aatgtcacaa
1141 gtgggattca gtgcagatta ctcttctcaa aatgatattc tgatgctggg tgcagtggga
1201 gcttttggct ggagtgggac cattgtccag aagacatctc atggccattt gatctttcct
1261 aaacaagcct tgaccaaat tctgcaggac agaaatcaca gttcatattt aggttactct
1321 gtggctgcaa tttctactgg agaaagcact cactttgttg ctggtgctcc tcgggcaaat
1381 tataccggcc agatagtgct atatagtgtg aatgagaatg gcaatatcac ggttattcag
1441 gctcaccgag gtgaccagat tggctcctat tttggtagtg tgctgtgttc agttgatgtg
1501 gataaagaca ccattacaga cgtgctcttg gtaggtgcac caatgtacat gagtgaccta
1561 aagaagagg aaggaagagt ctacctgttt actatcaaag agggcatttt gggtcagcac
1621 caatttcttg aaggccccga gggcattgaa aacactcgat ttggttcagc aattgcagct
1681 ctttcagaca tcaacatgga tggctttaat gatgtgattg ttggttcacc actagaaaat
```

Fig. 9 (cont.)

```
1741 cagaattctg gagctgtata catttacaat ggtcatcagg gcactatccg cacaaagtat
1801 tcccagaaaa tcttgggatc cgatggagcc tttaggagcc atctccagta ctttgggagg
1861 tccttggatg gctatggaga tttaaatggg gattccatca ccgatgtgtc tattggtgcc
1921 tttggacaag tggttcaact ctggtcacaa agtattgctg atgtagctat agaagcttca
1981 ttcacaccag aaaaaatcac tttggtcaac aagaatgctc agataattct caaactctgc
2041 ttcagtgcaa agttcagacc tactaagcaa acaatcaag tggccattgt atataacatc
2101 acacttgatg cagatggatt ttcatccaga gtaacctcca ggggttatt taaagaaaac
2161 aatgaaaggt gcctgcagaa gaatatggta gtaaatcaag cacagagttg ccccgagcac
2221 atcatttata tacaggagcc ctctgatgtt gtcaactctt ggatttgcg tgtggacatc
2281 agtctggaaa accctggcac tagccctgcc cttgaagcct attctgagac tgccaaggtc
2341 ttcagtattc cttccacaa agactgtggt gaggacggac tttgcatttc tgatctagtc
2401 ctagatgtcc gacaaatacc agctgctcaa gaacaaccct ttattgtcag caaccaaaac
2461 aaaaggttaa catttttcagt aacgctgaaa ataaaaggg aaagtgcata caacactgga
2521 attgttgttg attttttcaga aaacttgttt tttgcatcat tctccctgcc ggttgatggg
2581 acagaagtaa catgccaggt ggctgcatct cagaagtctg ttgcctgcga tgtaggctac
2641 cctgctttaa agagagaaca acaggtgact tttactatta actttgactt caatcttcaa
2701 aaccttcaga atcaggcgtc tctcagtttc caagccttaa gtgaaagcca agaagaaaac
2761 aaggctgata atttggtcaa cctcaaaatt cctctcctgt atgatgctga aattcactta
2821 acaagatcta ccaacataaa ttttttatgaa atctcttcgg atgggaatgt tccttcaatc
2881 gtgcacagtt ttgaagatgt tggtccaaaa ttcatcttct ccctgaaggt aacaacagga
2941 agtgttccag taagcatggc aactgtaatc atccacatcc ctcagtatac caaagaaaag
3001 aacccactga tgtacctaac tggggtgcaa acagacaagg ctggtgacat cagttgtaat
3061 gcagatatca atccactgaa aataggacaa acatcttctt ctgtatcttt caaaagtgaa
3121 aatttcaggc acaccaaaga attgaactgc agaactgctt cctgtagtaa tgttacctgc
3181 tggttgaaag acgttcacat gaaggagaa tactttgtta atgtgactac cagaatttgg
3241 aacgggactt tcgcatcatc aacgttccag acagtacagc taacggcagc tgcagaaatc
3301 aacacctata accctgagat atatgtgatt gaagataaca ctgttacgat tcccctgatg
3361 ataatgaaac ctgatgagaa agccgaagta ccaacaggag ttataatagg aagtataatt
3421 gctggaatcc ttttgctgtt agctctggtt gcaattttat ggaagctcgg cttcttcaaa
```

Fig. 9 (cont.)

```
3481 agaaaatatg aaaagatgac caaaaatcca gatgagattg atgagaccac agagctcagt
3541 agctga
```
(SEQ ID NO: 21)

β1 integrin isoform 1A precursor (hs) according to NCBI accession No. NP_002202.2:

```
  1 mnlqpifwig lissvccvfa qtdenrclka nakscgeciq agpncgwctn stflqegmpt
 61 sarcddleal kkkgcppddi enprgskdik knknvtnrsk gtaeklkped itqiqpqqlv
121 lrlrsgepqt ftlkfkraed ypidlyylmd lsysmkddle nvkslgtdlm nemrritsdf
181 rigfgsfvek tvmpyistto aklrnpctse qnctspfsyk nvlsltnkge vfnelvgkqr
241 isgnldspeg qfdaimqvav cgsliqwrnv trllvfstda qfhfagdgkl ggivlpndgq
301 chlennmytm shyydypsia hlvqklsenn iqtifavtee fqpvykelkn lipksavgtl
361 sanssnviql iidaynslss evilengkls egvtisyksy ckngvngtge ngrkcsnisi
421 gdevqfeisi tsnkcpkkds dsfkirplgf teevevilqy icececqseg ipespkcheg
481 ngtfecgacr cnegrvgrhc ecstdevnse dmdaycrken sseicsnnge cvcgqcvcrk
541 rdntneiysg kfcecdnfnc drsnglicgg ngvckcrvce cnpnytgsac dcsldtstce
601 asngqicngr gicecgvckc tdpkfqgqtc emcqtclgvc aehkecvqcr afnkgekkdt
661 ctqecsyfni tkvesrdklp qpvqpdpvsh ckekdvddcw fyftysvngn nevmvhvven
721 pecptgpdii pivagvvagi vliglallli wkllmiihdr refakfekek mnakwdtgen
781 piyksavttv vnpkyegk
```
(SEQ ID NO:22)

β1 integrin coding sequence (hs) isoform 1A according to NCBI accession No. NM_002211.3:

```
  1 atcagacgcg cagaggaggc ggggccgcgg ctggtttcct gccgggggc ggctctgggc
 61 cgccgagtcc cctcctcccg ccctgagga ggaggagccg ccgccacccg ccgcgcccga
121 cacccgggag gccccgccag cccgcgggag aggcccagcg ggagtcgcgg aacagcaggc
181 ccgagcccac cgcgccgggc ccggacgcc gcgcggaaaa gatgaattta caaccaattt
241 tctggattgg actgatcagt tcagtttgct gtgtgtttgc tcaaacagat gaaatagat
```

Fig. 9 (cont.)

```
 301 gtttaaaagc aaatgccaaa tcatgtggag aatgtataca agcagggcca aattgtgggt
 361 ggtgcacaaa ttcaacattt ttacaggaag gaatgcctac ttctgcacga tgtgatgatt
 421 tagaagcctt aaaaaagaag ggttgccctc cagatgacat agaaaatccc agaggctcca
 481 aagatataaa gaaaataaa aatgtaacca accgtagcaa aggaacagca gagaagctca
 541 agccagagga tattactcag atccaaccac agcagttggt tttgcgatta agatcagggg
 601 agccacagac atttacatta aaattcaaga gagctgaaga ctatcccatt gacctctact
 661 accttatgga cctgtcttac tcaatgaaag acgatttgga gaatgtaaaa agtcttggaa
 721 cagatctgat gaatgaaatg aggaggatta cttcggactt cagaattgga tttggctcat
 781 ttgtggaaaa gactgtgatg ccttacatta gcacaacacc agctaagctc aggaacccttt
 841 gcacaagtga acagaactgc accagcccat ttagctacaa aatgtgctc agtcttacta
 901 ataaaggaga agtatttaat gaacttgttg gaaaacagcg catatctgga aatttggatt
 961 ctccagaagg tggtttcgat gccatcatgc aagttgcagt tgtggatca ctgattggct
1021 ggaggaatgt tacacggctg ctggtgtttt ccacagatgc cgggtttcac tttgctggag
1081 atgggaaact tggtggcatt gttttaccaa atgatggaca atgtcacctg gaaaataata
1141 tgtacacaat gagccattat tatgattatc cttctattgc tcaccttgtc cagaaactga
1201 gtgaaaataa tattcagaca attttttgcag ttactgaaga atttcagcct gtttacaagg
1261 agctgaaaaa cttgatccct aagtcagcag taggaacatt atctgcaaat tctagcaatg
1321 taattcagtt gatcattgat gcatacaatt ccctttcctc agaagtcatt ttggaaaacg
1381 gcaaattgtc agaaggcgta acaataagtt acaaatctta ctgcaagaac ggggtgaatg
1441 gaacagggga aaatggaaga aaatgttcca atattccat tggagatgag gttcaatttg
1501 aaattagcat aacttcaaat aagtgtccaa aaaggattc tgacagcttt aaaattaggc
1561 ctctgggctt tacggaggaa gtagaggtta ttcttcagta catctgtgaa tgtgaatgcc
1621 aaagcgaagg catccctgaa agtcccaagt gtcatgaagg aaatgggaca tttgagtgtg
1681 gcgcgtgcag gtgcaatgaa gggcgtgttg gtagacattg tgaatgcagc acagatgaag
1741 ttacagtga agacatggat gcttactgca gggaagaaa cagttcagaa atctgcagta
1801 acaatggaga gtgcgtctgc ggacagtgtg tttgtaggaa gagggataat acaaatgaaa
1861 tttattctgg caaattctgc gagtgtgata atttcaactg tgatagatcc aatggcttaa
1921 tttgtggagg aaatggtgtt tgcaagtgtc gtgtgtgtga gtgcaaccccc aactacactg
1981 gcagtgcatg tgactgttct ttggatacta gtacttgtga agccagcaac ggacagatct
```

Fig. 9 (cont.)

```
2041 gcaatggccg gggcatctgc gagtgtggtg tctgtaagtg tacagatccg aagtttcaag
2101 ggcaaacgtg tgagatgtgt cagacctgcc ttggtgtctg tgctgagcat aaagaatgtg
2161 ttcagtgcag agccttcaat aaaggagaaa agaaagacac atgcacacag gaatgttcct
2221 attttaacat taccaaggta gaaagtcggg acaaattacc ccagccggtc caacctgatc
2281 ctgtgtccca ttgtaaggag aaggatgttg acgactgttg gttctatttt acgtattcag
2341 tgaatgggaa caacgaggtc atggttcatg ttgtggagaa tccagagtgt cccactggtc
2401 cagacatcat tccaattgta gctggtgtgg ttgctggaat tgttcttatt ggccttgcat
2461 tactgctgat atggaagctt ttaatgataa ttcatgacag aagggagttt gctaaatttg
2521 aaaaggagaa aatgaatgcc aaatgggaca cgggtgaaaa tcctatttat aagagtgccg
2581 taacaactgt ggtcaatccg aagtatgagg gaaaatgagt actgcccgtg caaatcccac
2641 aacactgaat gcaaagtagc aatttccata gtcacagtta ggtagcttta gggcaatatt
2701 gccatggttt tactcatgtg caggttttga aaatgtacaa tatgtataat ttttaaaatg
2761 ttttattatt ttgaaaataa tgttgtaatt catgccaggg actgacaaaa gacttgagac
2821 aggatggtta ctcttgtcag ctaaggtcac attgtgcctt tttgaccttt tcttcctgga
2881 ctattgaaat caagcttatt ggattaagtg atatttctat agcgattgaa agggcaatag
2941 ttaaagtaat gagcatgatg agagtttctg ttaatcatgt attaaaactg attttttagct
3001 ttacaaatat gtcagtttgc agttatgcag aatccaaagt aaatgtcctg ctagctagtt
3061 aaggattgtt ttaaatctgt tattttgcta tttgcctgtt agacatgact gatgacatat
3121 ctgaaagaca agtatgttga gagttgctgg tgtaaaatac gtttgaaata gttgatctac
3181 aaaggccatg ggaaaaattc agagagttag gaaggaaaaa ccaatagctt taaaacctgt
3241 gtgccatttt aagagttact taatgtttgg taacttttat gccttcactt tacaaattca
3301 agccttagat aaaagaaccg agcaattttc tgctaaaaag tccttgattt agcactattt
3361 acatacaggc catactttac aaagtatttg ctgaatgggg accttttgag ttgaatttat
3421 tttattattt ttattttgtt taatgtctgg tgctttctgt cacctcttct aatcttttaa
3481 tgtatttgtt tgcaattttg gggtaagact tttttatga gtactttttc tttgaagttt
3541 tagcggtcaa tttgcctttt taatgaacat gtgaagttat actgtggcta gcaacagct
3601 ctcacctacg cgagtcttac tttgagttag tgccataaca gaccactgta tgtttacttc
3661 tcaccatttg agttgcccat cttgtttcac actagtcaca ttcttgtttt aagtgccttt
3721 agttttaaca gttcactttt tacagtgcta tttactgaag ttatttatta aatatgccta
```

Fig. 9 (cont.)

```
3781 aaatacttaa atcggatgtc ttgactctga tgtatttat caggttgtgt gcatgaaatt 3841 tttatagatt aagaagttg aggaaaagca aaaaaaaa
```

(SEQ ID NO:23)

Fig.10

Fig. 10a: cDNA encoding LC of anti-α2 integrin mAB atggagacagacacactcctgctatgggtgctgctgctctgggttccaggttccacaggtaacattgtgctgaccca
atctccagcttctttggctgtgtctctagggcagagggccaccatatcctgcagagccagtgaaagtgttgagagtt
atggcaacagtttatttactggtaccagcagaaaccaggacaggcacccaaactcctcatctatcttgcatccaac
ctagcatctggggtccctgccaggttcagtggcagtgggtctaggacagacttcaccctcaccattgatcctgtgga
ggctgatgatgctgcaacctattactgtcagcaaaataatgaggatccgtacacgttcggaggggggaccaagctgg
aaataaaacgggctgatgctgcaccaactgtatccatcttcccaccatccagtgagcagttaacatctggaggtgcc
tcagtcgtgtgcttcttgaacaacttctaccccaaagacatcaatgtcaagtggaagattgatggcagtgaacgaca
aaatggcgtcctgaacagttggactgatcaggacagcaaagacagcacctacagcatgagcagcaccctcacgttga
ccaaggacgagtatgaacgacataacagctatacctgtgaggccactcacaagacatcaacttcacccattgtcaag
agcttcaacaggaatgagtgctag (SEQ ID NO:45)

Fig. 10b: cDNA encoding HC anti-α2 integrin mAB atgggatggagctgtatcatcctcttcttggtagcaacagccacaggtgtccactcccaggtccaactgcatcagcc
tggggctgaacttgtgaagcctggggctccagtgaagctgtcctgcaaggcttctggctacaccttcaccagctact
ggatgaactgggtgaagcagaggcctggacgaggcctcgagtggattggcaggattgatcctccgatagtgaaact
cactacaatcaaaagttcaaggacaaggccacactgactgtagacaaatcctccagcacagcctacatccaactcag
cagcctgacatctgaggactctgcggtctattactgtgcaaaggtgggacgggggtactttgactactggggccaag
gcaccactctcacagtctcctcagctaaaacaacagcccatcggtctatccactggcccctgtgtgtggagataca
actggctcctcggtgactctaggatgcctggtcaagggttatttccctgagccagtgacctttgacctggaactctgg
atccctgtccagtggtgtgcacaccttcccagctgtcctgcagtctgacctctacaccctcagcagctcagtgactg
taacctcgagcacctggcccagccagtccatcacctgcaatgtggcccacccggcaagcagcaccaaggtggacaag
aaaattgagcccagagggcccacaatcaagcctgtcctccatgcaaatgcccagcacctaacctcttgggtggacc
atccgtcttcatcttccctccaaagatcaaggatgtactcatgatctccctgagccccatagtcacatgtgtggtgg
tggatgtgagcgaggatgacccagatgtccagatcagctggtttgtgaacaacgtggaagtacacacagctcagaca
caaacccatagagaggattacaacagtactctccgggtggtcagtgccctcccatccagcaccaggactggatgag
tggcaaggagttcaaatgcaaggtcaacaacaaagacctcccagcgcccatcgagagaaccatctcaaaacccaaag
ggtcagtaagagctccacaggtatatgtcttgcctccaccagaagaagagatgactaagaaacaggtcactctgacc
tgcatggtcacagacttcatgcctgaagacatttacgtggagtggaccaacaacgggaaaacagagctaaactacaa
gaacactgaaccagtcctggactctgatggttcttacttcatgtacagcaagctgagagtggaaaagaagaactggg
tggaaagaaatagctactcctgttcagtggtccacgagggtctgcacaatcaccacacgactaagagcttctcccgg
actcccgggaagtga (SEQ ID NO:46)

Fig. 10c: Amino acid sequence of secreted LC of anti-α2 integrin mAB nivltqspaslavslgqratiscrasesvesygnsfiywyqqkpgqapklliylasnlasgvparfsgsgsrtdftl
tidpveaddaatyycqqnnedpytfgggtkleikradaaptvsifppsseqltsggasvvcflnnfypkdinvkwki
dgserqngvlnswtdqdskdstysmsstltltkdeyerhnsytceathktstspivksfnrnec (SEQ ID NO:47)

Fig. 10d: Amino acid sequence of secreted HC of anti-α2 integrin mAB

```
qvqlhqpgaelvkpgapvklsckasgytftsywmnwvkqrpgrglewigridpsdsethynqkfkdkatltvdksss
tayiqlssltsedsavyycakvgrgyfdywgqgttltvssakttapsvyplapvcgdttgssvtlgclvkgyfpepv
tltwnsgslssgvhtfpavlqsdlytlsssvtvtsstwpsqsitcnvahpasstkvdkkieprgptikpcppckcpa
pnllggpsvfifppkikdvlmislspivtcvvvdvseddpdvqiswfvnnvevhtaqtqthredynstlrvvsalpi
qhqdwmsgkefkckvnnkdlpapiertiskpkgsvrapqvyvlpppeeemtkkqvtltcmvtdfmpediyvewtnng
ktelnykntepvldsdgsyfmysklrvekknwvernsyscsvvheglhnhhttksfsrtpgk
```

(SEQ ID NO:48)

Fig. 10e: Amino acid sequence of comparator antibody

Amino acid sequence of LC of comparator

```
DFVMTQSPAFLSVTPGEKVTITCSAQSSVNYIHWYQQKPDQAPKKLIYDTSKLASGVPSR
FSGSGSGTDYTFTISSLEAEDAATYYCQQWTTNPLTFGQGTKVEIKRTVAAPSVFIFPPS
DEQLKSGTASVVCLLNNFYPREAKVQWKVDNALQSGNSQESVTEQDSKDSTYSLSSTLTL
SKADYEKHKVYACEVTHQGLSSPVTKSFNRGEC
```

(SEQ ID NO.53)

Fig. 10f: Amino acid sequence of HC of comparator

```
QVQLQESGPGLVKPSETLSLTCTVSGFSLTNYGIHWIRQPPGKGLEWLGVIWARGFTN
YNSALMSRLTISKDNSKNQVSLKLSSVTAADTAVYYCARANDGVYYAMDYWGQGTLVT
VSSASTKGPSVFPLAPCSRSTSESTAALGCLVKDYFPEPVTVSWNSGALTSGVHTFPA
VLQSSGLYSLSSVVTVPSSSLGTKTYTCNVDHKPSNTKVDKRVESKYGPPCPPCPAPE
FEGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLY
SRLTVDKSRWQEGNVFSCSVMHEALHNHYTQKSLSLSLG
```

(SEQ ID NO:54)

Fig. 11: Equilibrium dissociation constants $K_D$ for the humanized variants and the comparator as determined by Biacore Fig. 12: Binding of comparator mAb TMC2206 to integrin $\alpha_2$ I domain pre-bound by non-humanized Fab measured using Biacore Fig. 13: Binding of non-humanized Fab to integrin $\alpha_2$ I domain pre-bound by comparator mAb TMC2206

Figure 14: Inhibiton of platelet adhesion to collagen under static conditions using washed platelets ID 20).

SEQUENCE LISTING

<160> NUMBER OF SEQ ID NOS: 62

<210> SEQ ID NO 1
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable domain of
      anti-alpha2-integrin mAb

<400> SEQUENCE: 1

Asn Ile Val Leu Thr Gln Ser Pro Ala Ser Leu Ala Val Ser Leu Gly

```
                  1               5                  10                 15
              Gln Arg Ala Thr Ile Ser Cys Arg Ala Ser Glu Ser Val Glu Ser Tyr
                              20                 25                 30

Gly Asn Ser Phe Ile Tyr Trp Tyr Gln Gln Lys Pro Gly Gln Ala Pro
                          35                 40                 45

Lys Leu Leu Ile Tyr Leu Ala Ser Asn Leu Ala Ser Gly Val Pro Ala
               50                 55                 60

Arg Phe Ser Gly Ser Gly Ser Arg Thr Asp Phe Thr Leu Thr Ile Asp
              65                 70                 75                 80

Pro Val Glu Ala Asp Asp Ala Ala Thr Tyr Tyr Cys Gln Gln Asn Asn
                              85                 90                 95

Glu Asp Pro Tyr Thr Phe Gly Gly Gly Thr Lys Leu Glu Ile Lys
                          100                105                110

<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable domain of
      anti-alpha2-integrin mAb

<400> SEQUENCE: 2

Gln Val Gln Leu His Gln Pro Gly Ala Glu Leu Val Lys Pro Gly Ala
              1               5                  10                 15

Pro Val Lys Leu Ser Cys Lys Ala Ser Gly Tyr Thr Phe Thr Ser Tyr
                              20                 25                 30

Trp Met Asn Trp Val Lys Gln Arg Pro Gly Arg Gly Leu Glu Trp Ile
                          35                 40                 45

Gly Arg Ile Asp Pro Ser Asp Ser Glu Thr His Tyr Asn Gln Lys Phe
               50                 55                 60

Lys Asp Lys Ala Thr Leu Thr Val Asp Lys Ser Ser Ser Thr Ala Tyr
              65                 70                 75                 80

Ile Gln Leu Ser Ser Leu Thr Ser Glu Asp Ser Ala Val Tyr Tyr Cys
                              85                 90                 95

Ala Lys Val Gly Arg Gly Tyr Phe Asp Tyr Trp Gly Gln Gly Thr Thr
                          100                105                110

Leu Thr Val Ser Ser
                      115

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of the heavy chain variable domain

<400> SEQUENCE: 3

Gly Tyr Thr Phe Thr Ser Tyr Trp Met Asn
              1               5                  10

<210> SEQ ID NO 4
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: CDR2 of the heavy chain variable domain

<400> SEQUENCE: 4

Arg Ile Asp Pro Ser Asp Ser Glu Thr His Tyr Asn Gln Lys Phe Lys
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of the heavy chain variable domain

<400> SEQUENCE: 5

Val Gly Arg Gly Tyr Phe Asp Tyr
1               5

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of the light chain variable domain

<400> SEQUENCE: 6

Arg Ala Ser Glu Ser Val Glu Ser Tyr Gly Asn Ser Phe Ile Tyr
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of the light chain variable domain

<400> SEQUENCE: 7

Leu Ala Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of the light chain variable domain

<400> SEQUENCE: 8

Gln Gln Asn Asn Glu Asp Pro Tyr Thr
1               5

<210> SEQ ID NO 9
<211> LENGTH: 218
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric (anti-alpha2-VL-IGKC-CL) light chain

<400> SEQUENCE: 9

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ser Tyr
            20                  25                  30

Gly Asn Ser Phe Ile Tyr Trp Tyr Gln Gln Lys Pro Gly Gln Ala Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Ala Ala Thr Tyr Tyr Cys Gln Gln Asn Asn
                85                  90                  95

Glu Asp Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 10
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric (anti-alpha2-VH-IGHG4-CH1) mAb

<400> SEQUENCE: 10

Gln Val Gln Leu His Gln Pro Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
    50                  55                  60

Lys Asp Lys Ala Thr Leu Thr Val Asp Lys Ser Ser Thr Ala Tyr
65                  70                  75                  80
```

```
Ile Gln Leu Ser Ser Leu Thr Ser Glu Asp Ser Ala Val Tyr Tyr Cys
            85                  90                  95

Ala Lys Val Gly Arg Gly Tyr Phe Asp Tyr Trp Gly Gln Gly Thr Thr
        100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 11
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric (anti-alpha2-VH-IGHG1-CH1) heavy chain Fab fragment

<400> SEQUENCE: 11

Gln Val Gln Leu His Gln Pro Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
    50                  55                  60

Lys Asp Lys Ala Thr Leu Thr Val Asp Lys Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Lys Val Gly Arg Gly Tyr Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr His His His His His His
225                 230

<210> SEQ ID NO 12
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Light chain variable domain of
      anti-alpha2-integrin mAb

<400> SEQUENCE: 12
aacattgtgc tgacccaatc tccagcttct ttggctgtgt ctctagggca gagggccacc      60
atatcctgca gagccagtga aagtgttgag agttatggca cagtttttat ttactggtac     120
cagcagaaac aggacaggc acccaaactc ctcatctatc ttgcatccaa cctagcatct      180
ggggtccctg ccaggttcag tggcagtggg tctaggacag acttcaccct caccattgat     240
cctgtggagg ctgatgatgc tgcaacctat tactgtcagc aaaataatga ggatccgtac     300
acgttcggag gggggaccaa gctggaaata aaa                                  333

<210> SEQ ID NO 13
<211> LENGTH: 351
<212> TYPE: DNA

<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Heavy chain variable domain of
     anti-alpha2-integrin mAb

<400> SEQUENCE: 13

```
caggtccaac tgcatcagcc tggggctgaa cttgtgaagc tggggctcc agtgaagctg      60 tcctgcaagg cttctggcta ccttcacc agctactgga tgaactgggt gaagcagagg     120
cctggacgag gcctcgagtg gattggcagg attgatcctt ccgatagtga aactcactac    180
aatcaaaagt tcaaggacaa ggccacactg actgtagaca atcctccag cacagcctac     240 atccaactca gcagcctgac atctgaggac tctgcggtct attactgtgc aaaggtggga    300
cgggggtact ttgactactg gggccaaggc accactctca cagtctcctc a             351
```

<210> SEQ ID NO 14
<211> LENGTH: 654
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Chimeric (anti-alpha2-VL-IGKC-CL) light chain

<400> SEQUENCE: 14

```
aacattgtgc tgacccaatc tccagcttct ttggctgtgt ctctagggca gagggccacc     60
atatcctgca gagccagtga agtgttgag agttatggca cagttttat ttactggtac     120 cagcagaaac caggacaggc acccaaactc ctcatctatc ttgcatccaa cctagcatct    180
ggggtccctg ccaggttcag tggcagtggg tctaggacag acttcacccct caccattgat    240 cctgtggagg ctgatgatgc tgcaacctat tactgtcagc aaaataatga ggatccgtac    300
acgttcggag gggggaccaa gctggaaata aaacgtacgg tggccgctcc ttccgtgttc    360
atcttccctc cctccgacga gcagctgaag tccggcaccg cctccgtggt gtgtctgctg    420
aacaacttct accctcggga ggccaaggtg cagtggaagg tggacaacgc cctgcagtcc    480
ggcaactccc aggagtccgt caccgagcag gactccaagg acagcaccta ctccctgtcc    540
tccaccctga ccctgtccaa ggccgactac gagaagcaca aggtgtacgc ctgtgaggtg    600
acccaccagg gcctgtccag ccctgtgacc aagtccttca ccggggcga gtgc           654
```

<210> SEQ ID NO 15
<211> LENGTH: 1329
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: Chimeric (anti-alpha2-VH-IGHG4-CH1) mAb

<400> SEQUENCE: 15

```
caggtccaac tgcatcagcc tggggctgaa cttgtgaagc tggggctcc agtgaagctg      60 tcctgcaagg cttctggcta ccttcacc agctactgga tgaactgggt gaagcagagg     120
cctggacgag gcctcgagtg gattggcagg attgatcctt ccgatagtga aactcactac    180
aatcaaaagt tcaaggacaa ggccacactg actgtagaca atcctccag cacagcctac     240 atccaactca gcagcctgac atctgaggac tctgcggtct attactgtgc aaaggtggga    300
```

```
cgggggtact tgactactg gggccaaggc accactctca cagtctcctc agccagcacc        360
aagggccctt ccgtgttccc tctggcccct tgctcccggt ccacctccga gtccaccgcc        420
gctctgggct gcctggtgaa ggactacttc cctgagcctg tgaccgtgtc ctggaactct        480
ggcgccctga cctccggcgt gcacaccttc cctgccgtgc tgcagtcctc cggcctgtac        540
tccctgtcct ccgtggtgac cgtgccttcc tcctccctgg caccaagac ctacacctgt         600 aacgtggacc acaagccttc aacaccaag gtggacaagc gggtggagtc caagtacggc         660
cctccttgcc ctccctgccc tgccctgag ttcgagggcg acctagcgt gttcctgttc          720 cctcctaagc ctaaggacac cctgatgatc tcccggaccc ctgaggtgac ctgtgtggtg        780
gtggacgtgt cccaggagga ccctgaggtc cagttcaact ggtacgtgga cggcgtggag        840
gtgcacaacg ccaagaccaa gcctcgggag gagcagttca attccaccta ccgggtggtg        900
tctgtgctga ccgtgctgca ccaggactgg ctgaacggca agaatacaa gtgtaaggtc        960 tccaacaagg gcctgccctc ctccatcgag aaaaccatct ccaaggccaa gggccagcct       1020
agggagcctc aggtgtacac cctgcctcct agccaggaag agatgaccaa gaaccaggtg       1080
tccctgacct gtctggtgaa gggcttctac ccttccgaca tcgccgtgga gtgggagtcc       1140
aacggccagc ctgagaacaa ctacaagacc accctcctg tgctggactc cgacggctcc        1200
ttcttcctgt actccaggct gaccgtggac aagtcccggt ggcaggaggg caacgtcttt       1260
tcctgctccg tgatgcacga ggccctgcac aaccactaca cccagaagtc cctgtccctg       1320
tctctgggc                                                               1329

<210> SEQ ID NO 16
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric (anti-alpha2-VH-IGHG1-CH1) heavy chain
      Fab fragment

<400> SEQUENCE: 16
caggtccaac tgcatcagcc tggggctgaa cttgtgaagc ctggggctcc agtgaagctg         60
tcctgcaagg cttctggcta caccttcacc agctactgga tgaactgggt gaagcagagg        120
cctggacgag gcctcgagtg gattggcagg attgatcctt ccgatagtga aactcactac        180
aatcaaaagt tcaaggacaa ggccacactg actgtagaca atcctccag cacagcctac         240 atccaactca gcagcctgac atctgaggac tctgcggtct attactgtgc aaaggtggga        300 cggggggtact tgactactg gggccaaggc accactctca cagtctcctc agccagcacc        360
aagggcccat ccgtgttccc tctggcccct tcctccaagt ccacctccgg cggcaccgcc        420
gctctgggct gcctggtgaa ggactacttc cctgagcctg tgaccgtgtc ctggaactct        480
ggcgccctga ccagcggcgt gcacaccttc cctgccgtgc tgcagtcctc cggcctgtac        540
tccctgtcct ccgtggtgac cgtgccttcc tcctccctgg cacccagac ctacatctgt         600 aacgtgaacc acaagccctc aacaccaag gtggacaaga aggtggagcc taagtcctgt         660
gacaagaccc acaccccatca ccatcaccat cac                                    693

<210> SEQ ID NO 17
<211> LENGTH: 107
<212> TYPE: PRT
```

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human IGKC protein (Swiss-Prot: Q502W4)

<400> SEQUENCE: 17

```
Arg Thr Val Ala Ala Pro Ser Val Phe Ile Phe Pro Pro Ser Asp Glu
1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 18
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human IGHG4 protein (Swiss-Prot: P01861.1 (S108P, L115E))

<400> SEQUENCE: 18

```
Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325
```

<210> SEQ ID NO 19
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human IGHG1 protein (Swiss-Prot: Q569F4)

<400> SEQUENCE: 19

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 20
<211> LENGTH: 1181
<212> TYPE: PRT
<213> ORGANISM: Homo sapiens

<400> SEQUENCE: 20

Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
            20                  25                  30

Gly Leu Pro Glu Ala Lys Ile Phe Ser Gly Pro Ser Ser Glu Gln Phe
        35                  40                  45

Gly Tyr Ala Val Gln Gln Phe Ile Asn Pro Lys Gly Asn Trp Leu Leu
    50                  55                  60

Val Gly Ser Pro Trp Ser Gly Phe Pro Glu Asn Arg Met Gly Asp Val
65                  70                  75                  80

Tyr Lys Cys Pro Val Asp Leu Ser Thr Ala Thr Cys Glu Lys Leu Asn
            85                  90                  95

Leu Gln Thr Ser Thr Ser Ile Pro Asn Val Thr Glu Met Lys Thr Asn
            100                 105                 110

Met Ser Leu Gly Leu Ile Leu Thr Arg Asn Met Gly Thr Gly Gly Phe
        115                 120                 125

Leu Thr Cys Gly Pro Leu Trp Ala Gln Gln Cys Gly Asn Gln Tyr Tyr
    130                 135                 140

Thr Thr Gly Val Cys Ser Asp Ile Ser Pro Asp Phe Gln Leu Ser Ala
145                 150                 155                 160

Ser Phe Ser Pro Ala Thr Gln Pro Cys Pro Ser Leu Ile Asp Val Val
            165                 170                 175

Val Val Cys Asp Glu Ser Asn Ser Ile Tyr Pro Trp Asp Ala Val Lys
            180                 185                 190

Asn Phe Leu Glu Lys Phe Val Gln Gly Leu Asp Ile Gly Pro Thr Lys
        195                 200                 205

Thr Gln Val Gly Leu Ile Gln Tyr Ala Asn Asn Pro Arg Val Val Phe
    210                 215                 220

Asn Leu Asn Thr Tyr Lys Thr Lys Glu Glu Met Ile Val Ala Thr Ser
225                 230                 235                 240

Gln Thr Ser Gln Tyr Gly Gly Asp Leu Thr Asn Thr Phe Gly Ala Ile
```

```
                    245                 250                 255
Gln Tyr Ala Arg Lys Tyr Ala Tyr Ser Ala Ser Gly Gly Arg Arg
                260                 265                 270
Ser Ala Thr Lys Val Met Val Val Thr Asp Gly Glu Ser His Asp
            275                 280                 285
Gly Ser Met Leu Lys Ala Val Ile Asp Gln Cys Asn His Asp Asn Ile
290                 295                 300
Leu Arg Phe Gly Ile Ala Val Leu Gly Tyr Leu Asn Arg Asn Ala Leu
305                 310                 315                 320
Asp Thr Lys Asn Leu Ile Lys Glu Ile Lys Ala Ile Ala Ser Ile Pro
                325                 330                 335
Thr Glu Arg Tyr Phe Phe Asn Val Ser Asp Glu Ala Ala Leu Leu Glu
                340                 345                 350
Lys Ala Gly Thr Leu Gly Glu Gln Ile Phe Ser Ile Glu Gly Thr Val
            355                 360                 365
Gln Gly Gly Asp Asn Phe Gln Met Glu Met Ser Gln Val Gly Phe Ser
370                 375                 380
Ala Asp Tyr Ser Ser Gln Asn Asp Ile Leu Met Leu Gly Ala Val Gly
385                 390                 395                 400
Ala Phe Gly Trp Ser Gly Thr Ile Val Gln Lys Thr Ser His Gly His
                405                 410                 415
Leu Ile Phe Pro Lys Gln Ala Phe Asp Gln Ile Leu Gln Asp Arg Asn
                420                 425                 430
His Ser Ser Tyr Leu Gly Tyr Ser Val Ala Ala Ile Ser Thr Gly Glu
            435                 440                 445
Ser Thr His Phe Val Ala Gly Ala Pro Arg Ala Asn Tyr Thr Gly Gln
        450                 455                 460
Ile Val Leu Tyr Ser Val Asn Glu Asn Gly Asn Ile Thr Val Ile Gln
465                 470                 475                 480
Ala His Arg Gly Asp Gln Ile Gly Ser Tyr Phe Gly Ser Val Leu Cys
                485                 490                 495
Ser Val Asp Val Asp Lys Asp Thr Ile Thr Asp Val Leu Leu Val Gly
            500                 505                 510
Ala Pro Met Tyr Met Ser Asp Leu Lys Lys Glu Glu Gly Arg Val Tyr
        515                 520                 525
Leu Phe Thr Ile Lys Glu Gly Ile Leu Gly Gln His Gln Phe Leu Glu
    530                 535                 540
Gly Pro Glu Gly Ile Glu Asn Thr Arg Phe Gly Ser Ala Ile Ala Ala
545                 550                 555                 560
Leu Ser Asp Ile Asn Met Asp Gly Phe Asn Asp Val Ile Val Gly Ser
                565                 570                 575
Pro Leu Glu Asn Gln Asn Ser Gly Ala Val Tyr Ile Tyr Asn Gly His
                580                 585                 590
Gln Gly Thr Ile Arg Thr Lys Tyr Ser Gln Lys Ile Leu Gly Ser Asp
            595                 600                 605
Gly Ala Phe Arg Ser His Leu Gln Tyr Phe Gly Arg Ser Leu Asp Gly
        610                 615                 620
Tyr Gly Asp Leu Asn Gly Asp Ser Ile Thr Asp Val Ser Ile Gly Ala
625                 630                 635                 640
Phe Gly Gln Val Val Gln Leu Trp Ser Gln Ser Ile Ala Asp Val Ala
                645                 650                 655
Ile Glu Ala Ser Phe Thr Pro Glu Lys Ile Thr Leu Val Asn Lys Asn
                660                 665                 670
```

```
Ala Gln Ile Ile Leu Lys Leu Cys Phe Ser Ala Lys Phe Arg Pro Thr
            675                 680                 685

Lys Gln Asn Asn Gln Val Ala Ile Val Tyr Asn Ile Thr Leu Asp Ala
690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
            755                 760                 765

Pro Ala Leu Glu Ala Tyr Ser Glu Thr Ala Lys Val Phe Ser Ile Pro
770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
            835                 840                 845

Leu Phe Phe Ala Ser Phe Ser Leu Pro Val Asp Gly Thr Glu Val Thr
            850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
                885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
            915                 920                 925

Lys Ile Pro Leu Leu Tyr Asp Ala Glu Ile His Leu Thr Arg Ser Thr
930                 935                 940

Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
                965                 970                 975

Val Thr Thr Gly Ser Val Pro Val Ser Met Ala Thr Val Ile Ile His
            980                 985                 990

Ile Pro Gln Tyr Thr Lys Glu Lys Asn Pro Leu Met Tyr Leu Thr Gly
            995                 1000                1005

Val Gln Thr Asp Lys Ala Gly Asp Ile Ser Cys Asn Ala Asp Ile
    1010                1015                1020

Asn Pro Leu Lys Ile Gly Gln Thr Ser Ser Ser Val Ser Phe Lys
    1025                1030                1035

Ser Glu Asn Phe Arg His Thr Lys Glu Leu Asn Cys Arg Thr Ala
    1040                1045                1050

Ser Cys Ser Asn Val Thr Cys Trp Leu Lys Asp Val His Met Lys
    1055                1060                1065

Gly Glu Tyr Phe Val Asn Val Thr Thr Arg Ile Trp Asn Gly Thr
    1070                1075                1080
```

Phe Ala Ser Ser Thr Phe Gln Thr Val Gln Leu Thr Ala Ala Ala
        1085                1090                1095

Glu Ile Asn Thr Tyr Asn Pro Glu Ile Tyr Val Ile Glu Asp Asn
    1100                1105                1110

Thr Val Thr Ile Pro Leu Met Ile Met Lys Pro Asp Glu Lys Ala
    1115                1120                1125

Glu Val Pro Thr Gly Val Ile Ile Gly Ser Ile Ile Ala Gly Ile
    1130                1135                1140

Leu Leu Leu Leu Ala Leu Val Ala Ile Leu Trp Lys Leu Gly Phe
    1145                1150                1155

Phe Lys Arg Lys Tyr Glu Lys Met Thr Lys Asn Pro Asp Glu Ile
    1160                1165                1170

Asp Glu Thr Thr Glu Leu Ser Ser
    1175                1180

<210> SEQ ID NO 21
<211> LENGTH: 3546
<212> TYPE: DNA
<213> ORGANISM: Homo sapiens

<400> SEQUENCE: 21

| | | | | | |
|---|---|---|---|---|---|
| atggggccag | aacggacagg | ggccgcgccg | ctgccgctgc | tgctggtgtt | agcgctcagt | 60 |
| caaggcattt | taaattgttg | tttggcctac | aatgttggtc | tcccagaagc | aaaaatattt | 120 |
| tccggtcctt | caagtgaaca | gtttggctat | gcagtgcagc | agtttataaa | tccaaaaggc | 180 |
| aactggttac | tggttggttc | accctggagt | ggctttcctg | agaaccgaat | gggagatgtg | 240 |
| tataaatgtc | ctgttgacct | atccactgcc | acatgtgaaa | aactaaattt | gcaaacttca | 300 |
| acaagcattc | caaatgttac | tgagatgaaa | accaacatga | gcctcggctt | gatcctcacc | 360 |
| aggaacatgg | gaactggagg | ttttctcaca | tgtggtcctc | tgtgggcaca | gcaatgtggg | 420 |
| aatcagtatt | acacaacggg | tgtgtgttct | gacatcagtc | ctgattttca | gctctcagcc | 480 |
| agcttctcac | ctgcaactca | gccctgccct | tccctcatag | atgttgtggt | tgtgtgtgat | 540 |
| gaatcaaata | gtatttatcc | tgggatgca | gtaaagaatt | ttttggaaaa | atttgtacaa | 600 |
| ggcctggata | taggccccac | aaagacacag | gtggggttaa | ttcagtatgc | caataatcca | 660 |
| agagttgtgt | ttaacttgaa | cacatataaa | accaaagaag | aaatgattgt | agcaacatcc | 720 |
| cagacatccc | aatatggtgg | ggacctcaca | aacacattcg | gagcaattca | atatgcaaga | 780 |
| aaatatgctt | attcagcagc | ttctggtggg | cgacgaagtg | ctacgaaagt | aatggtagtt | 840 |
| gtaactgacg | gtgaatcaca | tgatggttca | atgttgaaag | ctgtgattga | tcaatgcaac | 900 |
| catgacaata | tactgaggtt | tggcatagca | gttcttgggt | acttaaacag | aaacgccctt | 960 |
| gatactaaaa | atttaataaa | agaaataaaa | gcaatcgcta | gtattccaac | agaaagatac | 1020 |
| ttttcaatg | tgtctgatga | agcagctcta | ctagaaaagg | ctgggacatt | aggagaacaa | 1080 |
| attttcagca | ttgaaggtac | tgttcaagga | ggagacaact | tcagatggaa | atgtcacaa | 1140 |
| gtgggattca | gtgcagatta | ctcttctcaa | aatgatattc | tgatgctggg | tgcagtggga | 1200 |
| gcttttggct | ggagtgggac | cattgtccag | aagacatctc | atggccattt | gatctttcct | 1260 |
| aaacaagcct | tgaccaaat | tctgcaggac | agaaatcaca | gttcatattt | aggttactct | 1320 |
| gtggctgcaa | tttctactgg | agaaagcact | cactttgttg | ctggtgctcc | tcgggcaaat | 1380 |
| tataccggcc | agatagtgct | atatagtgtg | aatgagaatg | gcaatatcac | ggttattcag | 1440 |
| gctcaccgag | gtgaccagat | tggctcctat | tttggtagtg | tgctgtgttc | agttgatgtg | 1500 |

```
gataaagaca ccattacaga cgtgctcttg gtaggtgcac caatgtacat gagtgaccta    1560
aagaaagagg aaggaagagt ctacctgttt actatcaaag agggcatttt gggtcagcac    1620
caatttcttg aaggccccga gggcattgaa acactcgat  ttggttcagc aattgcagct    1680
ctttcagaca tcaacatgga tggctttaat gatgtgattg ttggttcacc actagaaaat    1740
cagaattctg gagctgtata catttacaat ggtcatcagg gcactatccg cacaaagtat    1800
tcccagaaaa tcttgggatc cgatggagcc tttaggagcc atctccagta ctttgggagg    1860
tccttggatg gctatggaga tttaaatggg gattccatca ccgatgtgtc tattggtgcc    1920
tttggacaag tggttcaact ctggtcacaa agtattgctg atgtagctat agaagcttca    1980
ttcacaccag aaaaaatcac tttggtcaac aagaatgctc agataattct caaactctgc    2040
ttcagtgcaa agttcagacc tactaagcaa acaatcaag  tggccattgt atataacatc    2100
acacttgatg cagatggatt ttcatccaga gtaacctcca gggggttatt taaagaaaac    2160
aatgaaaggt gcctgcagaa gaatatggta gtaaatcaag cacagagttg ccccgagcac    2220
atcatttata tacaggagcc ctctgatgtt gtcaactctt tggatttgcg tgtggacatc    2280
agtctggaaa accctggcac tagccctgcc cttgaagcct attctgagac tgccaaggtc    2340
ttcagtattc ctttccacaa agactgtggt gaggacggac tttgcatttc tgatctagtc    2400
ctagatgtcc gacaaatacc agctgctcaa gaacaaccct ttattgtcag caaccaaaac    2460
aaaaggttaa cattttcagt aacgctgaaa ataaaaggg  aaagtgcata caacactgga    2520
attgttgttg attttcaga  aaacttgttt tttgcatcat ctccctgcc  ggttgatggg    2580 acagaagtaa catgccaggt ggctgcatct cagaagtctg ttgcctgcga tgtaggctac    2640
cctgctttaa agagagaaca acaggtgact tttactatta actttgactt caatcttcaa    2700
aaccttcaga atcaggcgtc tctcagtttc caagccttaa gtgaaagcca agaagaaac    2760 aaggctgata atttggtcaa cctcaaaatt cctctcctgt atgatgctga aattcactta    2820
acaagatcta ccaacataaa ttttttatgaa atctcttcgg atgggaatgt tccttcaatc    2880
gtgcacagtt ttgaagatgt tggtccaaaa ttcatcttct ccctgaaggt aacaacagga    2940
agtgttccag taagcatggc aactgtaatc atccacatcc ctcagtatac caagaaaaag    3000
aacccactga tgtacctaac tggggtgcaa acagacaagg ctggtgacat cagttgtaat    3060
gcagatatca atccactgaa aataggacaa acatcttctt ctgtatcttt caaaagtgaa    3120
aatttcaggc acaccaaaga attgaactgc agaactgctt cctgtagtaa tgttacctgc    3180
tggttgaaag acgttcacat gaaggagaaa tactttgtta atgtgactac cagaatttgg    3240
aacgggactt tcgcatcatc aacgttccag acagtacagc taacggcagc tgcagaaatc    3300
aacacctata accctgagat atatgtgatt gaagataacc tgttacgat  tcccctgatg    3360 ataatgaaac ctgatgagaa agccgaagta ccaacaggag ttataatagg aagtataatt    3420
gctggaatcc ttttgctgtt agctctggtt gcaattttat ggaagctcgg cttcttcaaa    3480
agaaaatatg aaaagatgac caaaaatcca gatgagattg atgagaccac agagctcagt    3540
agctga                                                              3546
```

<210> SEQ ID NO 22
<211> LENGTH: 798
<212> TYPE: PRT
<213> ORGANISM: Homo sapiens

<400> SEQUENCE: 22

Met Asn Leu Gln Pro Ile Phe Trp Ile Gly Leu Ile Ser Ser Val Cys

-continued

```
1               5                   10                  15
Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
                35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
                100                 105                 110

Gln Ile Gln Pro Gln Gln Leu Val Leu Arg Leu Arg Ser Gly Glu Pro
                115                 120                 125

Gln Thr Phe Thr Leu Lys Phe Lys Arg Ala Glu Asp Tyr Pro Ile Asp
                130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
                180                 185                 190

Met Pro Tyr Ile Ser Thr Thr Pro Ala Lys Leu Arg Asn Pro Cys Thr
                195                 200                 205

Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
                275                 280                 285

Lys Leu Gly Gly Ile Val Leu Pro Asn Asp Gly Gln Cys His Leu Glu
                290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
                355                 360                 365

Gln Leu Ile Ile Asp Ala Tyr Asn Ser Leu Ser Ser Glu Val Ile Leu
                370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430
```

```
Asn Lys Cys Pro Lys Lys Asp Ser Asp Ser Phe Lys Ile Arg Pro Leu
        435                 440                 445
Gly Phe Thr Glu Glu Val Glu Val Ile Leu Gln Tyr Ile Cys Glu Cys
450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
                485                 490                 495
Gly Arg His Cys Glu Cys Ser Thr Asp Glu Val Asn Ser Glu Asp Met
                500                 505                 510
Asp Ala Tyr Cys Arg Lys Glu Asn Ser Ser Glu Ile Cys Ser Asn Asn
            515                 520                 525
Gly Glu Cys Val Cys Gly Gln Cys Val Cys Arg Lys Arg Asp Asn Thr
        530                 535                 540
Asn Glu Ile Tyr Ser Gly Lys Phe Cys Glu Cys Asp Asn Phe Asn Cys
545                 550                 555                 560
Asp Arg Ser Asn Gly Leu Ile Cys Gly Gly Asn Gly Val Cys Lys Cys
                565                 570                 575
Arg Val Cys Glu Cys Asn Pro Asn Tyr Thr Gly Ser Ala Cys Asp Cys
                580                 585                 590
Ser Leu Asp Thr Ser Thr Cys Glu Ala Ser Asn Gly Gln Ile Cys Asn
            595                 600                 605
Gly Arg Gly Ile Cys Glu Cys Gly Val Cys Lys Cys Thr Asp Pro Lys
        610                 615                 620
Phe Gln Gly Gln Thr Cys Glu Met Cys Gln Thr Cys Leu Gly Val Cys
625                 630                 635                 640
Ala Glu His Lys Glu Cys Val Gln Cys Arg Ala Phe Asn Lys Gly Glu
                645                 650                 655
Lys Lys Asp Thr Cys Thr Gln Glu Cys Ser Tyr Phe Asn Ile Thr Lys
                660                 665                 670
Val Glu Ser Arg Asp Lys Leu Pro Gln Pro Val Gln Pro Asp Pro Val
            675                 680                 685
Ser His Cys Lys Glu Lys Asp Val Asp Asp Cys Trp Phe Tyr Phe Thr
        690                 695                 700
Tyr Ser Val Asn Gly Asn Asn Glu Val Met Val His Val Val Glu Asn
705                 710                 715                 720
Pro Glu Cys Pro Thr Gly Pro Asp Ile Ile Pro Ile Val Ala Gly Val
                725                 730                 735
Val Ala Gly Ile Val Leu Ile Gly Leu Ala Leu Leu Leu Ile Trp Lys
                740                 745                 750
Leu Leu Met Ile Ile His Asp Arg Arg Glu Phe Ala Lys Phe Glu Lys
            755                 760                 765
Glu Lys Met Asn Ala Lys Trp Asp Thr Gly Glu Asn Pro Ile Tyr Lys
        770                 775                 780
Ser Ala Val Thr Thr Val Val Asn Pro Lys Tyr Glu Gly Lys
785                 790                 795

<210> SEQ ID NO 23
<211> LENGTH: 3879
<212> TYPE: DNA
<213> ORGANISM: Homo sapiens

<400> SEQUENCE: 23
atcagacgcg cagaggaggc ggggccgcgg ctggtttcct gccggggggc ggctctgggc     60
```

```
cgccgagtcc cctcctcccg cccctgagga ggaggagccg ccgccacccg ccgcgcccga    120
cacccgggag gccccgccag cccgcgggag aggcccagcg ggagtcgcgg aacagcaggc    180
ccgagcccac cgcgccgggc cccggacgcc gcgcggaaaa gatgaattta caaccaattt    240
tctggattgg actgatcagt tcagtttgct gtgtgtttgc tcaaacagat gaaaatagat    300
gtttaaaagc aaatgccaaa tcatgtggag aatgtataca agcagggcca aattgtgggt    360
ggtgcacaaa ttcaacattt ttacaggaag gaatgcctac ttctgcacga tgtgatgatt    420
tagaagcctt aaaaagaag ggttgccctc cagatgacat agaaaatccc agaggctcca    480
aagatataaa gaaaataaa aatgtaacca accgtagcaa aggaacagca gagaagctca    540
agccagagga tattactcag atccaaccac agcagttggt tttgcgatta agatcagggg    600
agccacagac atttacatta aaattcaaga gagctgaaga ctatcccatt gacctctact    660
accttatgga cctgtcttac tcaatgaaag acgatttgga gaatgtaaaa agtcttggaa    720
cagatctgat gaatgaaatg aggaggatta cttcggactt cagaattgga tttggctcat    780
ttgtggaaaa gactgtgatg ccttacatta gcacaacacc agctaagctc aggaacccctt   840 gcacaagtga acagaactgc accagcccat ttagctacaa aaatgtgctc agtcttacta    900
ataaaggaga agtatttaat gaacttgttg gaaaacagcg catatctgga aatttggatt    960
ctccagaagg tggtttcgat gccatcatgc aagttgcagt ttgtggatca ctgattggct    1020
ggaggaatgt tacacggctg ctggtgtttt ccacagatgc cgggtttcac tttgctggag    1080
atgggaaact tggtggcatt gttttaccaa atgatggaca atgtcacctg gaaaataata    1140
tgtacacaat gagccattat tatgattatc cttctattgc tcaccttgtc cagaaactga    1200
gtgaaaataa tattcagaca attttttgcag ttactgaaga atttcagcct gtttacaagg    1260
agctgaaaaa cttgatccct aagtcagcag taggaacatt atctgcaaat tctagcaatg    1320
taattcagtt gatcattgat gcatacaatt cccttctc agaagtcatt ttggaaaacg    1380
gcaaattgtc agaaggcgta acaataagtt acaaatctta ctgcaagaac ggggtgaatg    1440
gaacagggga aaatggaaga aaatgttcca atatttccat tggagatgag gttcaatttg    1500
aaattagcat aacttcaaat aagtgtccaa aaaggattc tgacagcttt aaaattaggc    1560
ctctgggctt tacggaggaa gtagaggtta ttcttcagta catctgtgaa tgtgaatgcc    1620
aaagcgaagg catccctgaa agtcccaagt gtcatgaagg aaatgggaca tttgagtgtg    1680
gcgcgtgcag gtgcaatgaa gggcgtgttg gtagacattg tgaatgcagc acagatgaag    1740
ttaacagtga agacatggat gcttactgca ggaaagaaaa cagttcagaa atctgcagta    1800
acaatggaga gtgcgtctgc ggacagtgtg tttgtaggaa gagggataat acaaatgaaa    1860
tttattctgg caaattctgc gagtgtgata atttcaactg tgatagatcc aatggcttaa    1920
tttgtggagg aaatggtgtt tgcaagtgtc gtgtgtgtga gtgcaaccc aactacactg    1980 gcagtgcatg tgactgttct ttggatacta gtacttgtga agccagcaac ggacagatct    2040
gcaatggccg gggcatctgc gagtgtggtg tctgtaagtg tacagatccg aagtttcaag    2100
ggcaaacgtg tgagatgtgt cagacctgcc ttggtgtctg tgctgagcat aaagaatgtg    2160
ttcagtgcag agccttcaat aaaggagaaa agaaagacac atgcacacag gaatgttcct    2220
attttaacat taccaaggta gaaagtcggg acaaattacc ccagccggtc caacctgatc    2280
ctgtgtccca ttgtaaggag aaggatgttg acgactgttg gttctatttt acgtattcag    2340
tgaatgggaa caacgaggtc atggttcatg ttgtggagaa tccagagtgt cccactggtc    2400
```

```
cagacatcat tccaattgta gctggtgtgg ttgctggaat tgttcttatt ggccttgcat    2460
tactgctgat atggaagctt ttaatgataa ttcatgacag aagggagttt gctaaatttg    2520
aaaaggagaa aatgaatgcc aaatgggaca cgggtgaaaa tcctatttat aagagtgccg    2580
taacaactgt ggtcaatccg aagtatgagg gaaaatgagt actgcccgtg caaatcccac    2640
aacactgaat gcaaagtagc aatttccata gtcacagtta ggtagcttta gggcaatatt    2700
gccatggttt tactcatgtg caggttttga aaatgtacaa tatgtataat ttttaaaatg    2760
ttttattatt ttgaaaataa tgttgtaatt catgccaggg actgacaaaa gacttgagac    2820
aggatggtta ctcttgtcag ctaaggtcac attgtgcctt tttgaccttt tcttcctgga    2880
ctattgaaat caagcttatt ggattaagtg atatttctat agcgattgaa agggcaatag    2940
ttaaagtaat gagcatgatg agagtttctg ttaatcatgt attaaaactg attttagct    3000 ttacaaatat gtcagtttgc agttatgcag aatccaaagt aaatgtcctg ctagctagtt    3060
aaggattgtt ttaaatctgt tattttgcta tttgcctgtt agacatgact gatgacatat    3120
ctgaaagaca agtatgttga gagttgctgg tgtaaaatac gtttgaaata gttgatctac    3180
aaaggccatg ggaaaaattc agagagttag gaaggaaaaa ccaatagctt taaaacctgt    3240
gtgccatttt aagagttact taatgtttgg taacttttat gccttcactt tacaaattca    3300
agccttagat aaaagaaccg agcaattttc tgctaaaaag tccttgattt agcactattt    3360
acatacaggc catactttac aaagtatttg ctgaatgggg accttttgag ttgaatttat    3420
tttattattt ttattttgtt taatgtctgg tgctttctgt cacctcttct aatcttttaa    3480
tgtatttgtt tgcaattttg gggtaagact tttttatga gtacttttc tttgaagttt     3540 tagcggtcaa tttgcctttt taatgaacat gtgaagttat actgtggcta tgcaacagct    3600
ctcacctacg cgagtcttac tttgagttag tgccataaca gaccactgta tgtttacttc    3660
tcaccatttg agttgcccat cttgtttcac actagtcaca ttcttgtttt aagtgccttt    3720
agttttaaca gttcactttt tacagtgcta tttactgaag ttatttatta aatatgccta    3780
aaatacttaa atcggatgtc ttgactctga tgtatttat caggttgtgt gcatgaaatt     3840
tttatagatt aaagaagttg aggaaaagca aaaaaaaa                            3879
```

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-GeneRacer primer for amplifying variable
      domains of anti-alpha2-integrin mAb

<400> SEQUENCE: 24
cgactggagc acgaggacac tga                                              23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: RACEMOG2a: 3'-primer internal to murine hinge
      region for amplifying variable domains of anti-alpha2-integrin mAb

<400> SEQUENCE: 25
aggacagggc ttgattgtgg g                                              21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: CKFOR: 3'-primer internal to murine Ck region
      for amplifying variable domains of anti-alpha2-integrin mAb

<400> SEQUENCE: 26
ctcattcctg ttgaagctct tgac                                           24

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: alpha2mAB-VL FOR: primer for amplifying the
      light chain of anti-alpha2-integrin mAb

<400> SEQUENCE: 27
ctggtggcca ccgccaccgg cgtgcacagc aacattgtgc tgacccaatc tc            52

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: alpha2mAB-VL REV: primer for amplifying the
      light chain of anti-alpha2-integrin mAb

<400> SEQUENCE: 28
accgtacgtt ttatttccag cttggtcccc                                     30

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: alpha2mAB mAB-VH FOR: primer for amplifying the
      heavy chain of anti-alpha2-integrin mAb

<400> SEQUENCE: 29
ctggtggcca ccgccaccgg cgtgcacagc caggtccaac tgcatcagcc tg            52

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: alpha2mAB mAB-VH REV: primer for amplifying the
      heavy chain of anti-alpha2-integrin mAb

```
<400> SEQUENCE: 30 tagggcccctt ggtgctggct gaggagactg tgagagtgg                              39

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Leader FOR1-54: primer for introducing leader
      sequence into the variable chains of anti-alpha2-integrin mAb

<400> SEQUENCE: 31
gctagcacca tgggctggtc ctgcatcatc ctgtttctgg tggccaccgc cacc             54

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Leader FOR1-23: primer for introducing leader
      sequence into the variable chains of anti-alpha2-integrin mAb

<400> SEQUENCE: 32
caagctagca ccatgggctg gtcctg                                             26

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC1: Light chain variable domain of
      anti-alpha2-integrin mAb with humanizing mutations

<400> SEQUENCE: 33

Asn Ile Val Leu Thr Gln Ser Pro Ser Ser Leu Ala Val Ser Val Gly
1               5                  10                  15

Gln Arg Ala Thr Ile Ser Cys Arg Ala Ser Glu Ser Val Glu Ser Tyr
            20                  25                  30

Gly Asn Ser Phe Ile Tyr Trp Tyr Gln Gln Lys Pro Gly Lys Ala Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: LC2: Light chain variable domain of
      anti-alpha2-integrin mAb with humanizing mutations

<400> SEQUENCE: 34

Asn Ile Val Leu Thr Gln Ser Pro Ser Leu Ala Val Ser Val Gly
1               5                   10                  15

Gln Arg Ala Thr Ile Ser Cys Arg Ala Ser Glu Ser Val Glu Ser Tyr
            20                  25                  30

Gly Gln Ser Phe Ile Tyr Trp Tyr Gln Gln Lys Pro Gly Lys Ala Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC3: Light chain variable domain of
      anti-alpha2-integrin mAb with humanizing and stabilizing mutations

<400> SEQUENCE: 35

Asn Ile Val Leu Thr Gln Ser Pro Ser Ser Leu Ser Val Ser Val Gly
1               5                   10                  15

Gln Arg Ala Thr Ile Ser Cys Arg Ala Ser Glu Ser Val Glu Ser Tyr
            20                  25                  30

Gly Asn Ser Phe Ile Tyr Trp Tyr Gln Gln Lys Pro Gly Gln Ala Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC4: Light chain variable domain of
      anti-alpha2-integrin mAb with humanizing and stabilizing mutations

<400> SEQUENCE: 36

Asn Ile Val Leu Thr Gln Ser Pro Ser Ser Leu Ser Val Ser Val Gly
1               5                   10                  15
```

```
Gln Arg Ala Thr Ile Ser Cys Arg Ala Ser Glu Ser Val Glu Ser Tyr
            20                  25                  30

Gly Gln Ser Phe Ile Tyr Trp Tyr Gln Gln Lys Pro Gly Gln Ala Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110
```

<210> SEQ ID NO 37
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC5: Light chain variable domain of
      anti-alpha2-integrin mAb with grafted mutations

<400> SEQUENCE: 37

```
Asn Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Ser Tyr
            20                  25                  30

Gly Asn Ser Phe Ile Tyr Trp Tyr Gln Gln Lys Pro Gly Gln Pro Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Thr Ala Asn Tyr Tyr Cys Gln Gln Asn Asn
                85                  90                  95

Glu Asp Pro Tyr Thr Phe Gly Gly Gly Thr Lys Leu Glu Ile Lys
            100                 105                 110
```

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC1: Heavy chain variable domain of
      anti-alpha2-integrin mAb with humanizing mutations

<400> SEQUENCE: 38

```
Gln Val Gln Leu His Gln Pro Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Arg Ile Asp Pro Ser Asp Ser Glu Thr His Tyr Asn Gln Lys Phe
    50                  55                  60
```

```
Lys Asp Arg Ala Thr Leu Thr Val Asp Lys Ser Ser Thr Ala Tyr
 65                  70                  75                  80

Ile Gln Leu Ser Ser Leu Thr Ser Glu Asp Ser Ala Val Tyr Tyr Cys
                 85                  90                  95

Ala Lys Val Gly Arg Gly Tyr Phe Asp Tyr Trp Gly Gln Gly Thr Thr
            100                 105                 110

Leu Thr Val Val Ser
        115

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC2: Heavy chain variable domain of
      anti-alpha2-integrin mAb with humanizing mutations

<400> SEQUENCE: 39

Gln Val Gln Leu His Gln Pro Gly Ala Glu Leu Val Lys Pro Gly Ala
 1               5                  10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Arg Ile Asp Pro Ser Glu Ser Glu Thr His Tyr Asn Gln Lys Phe
 50                  55                  60

Lys Asp Arg Ala Thr Leu Thr Val Asp Lys Ser Ser Thr Ala Tyr
 65                  70                  75                  80

Ile Gln Leu Ser Ser Leu Thr Ser Glu Asp Ser Ala Val Tyr Tyr Cys
                 85                  90                  95

Ala Lys Val Gly Arg Gly Tyr Phe Asp Tyr Trp Gly Gln Gly Thr Thr
            100                 105                 110

Leu Thr Val Val Ser
        115

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC3: Heavy chain variable domain of
      anti-alpha2-integrin mAb with humanizing and stabilizing mutations

<400> SEQUENCE: 40

Gln Val Gln Leu His Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
 50                  55                  60

Lys Asp Lys Ala Thr Leu Thr Val Asp Lys Ser Ser Thr Ala Tyr
 65                  70                  75                  80
```

```
Ile Gln Leu Ser Ser Leu Thr Ser Glu Asp Ser Ala Val Tyr Tyr Cys
                85                  90                  95

Ala Lys Val Gly Arg Gly Tyr Phe Asp Tyr Trp Gly Gln Gly Thr Thr
            100                 105                 110

Leu Thr Val Val Ser
        115

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC4: Heavy chain variable domain of
      anti-alpha2-integrin mAb with humanizing and stabilizing mutations

<400> SEQUENCE: 41

Gln Val Gln Leu His Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Lys Tyr Tyr Cys
                85                  90                  95

Ala Lys Val Gly Arg Gly Tyr Phe Asp Tyr Trp Gly Gln Gly Thr Thr
            100                 105                 110

Leu Thr Val Val Ser
        115

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC5: Heavy chain variable domain of
      anti-alpha2-integrin mAb with humanizing and stabilizing mutations

<400> SEQUENCE: 42

Gln Val Gln Leu His Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Glu Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95
```

Ala Lys Val Gly Arg Gly Tyr Phe Asp Tyr Trp Gly Gln Gly Thr Thr
            100                 105                 110

Leu Thr Val Val Ser
        115

<210> SEQ ID NO 43
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC6: Heavy chain variable domain of
      anti-alpha2-integrin mAb with humanizing and stabilizing mutations

<400> SEQUENCE: 43

Gln Val Gln Leu His Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Glu Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Lys Tyr Tyr Cys
                85                  90                  95

Ala Lys Val Gly Arg Gly Tyr Phe Asp Tyr Trp Gly Gln Gly Thr Thr
            100                 105                 110

Leu Thr Val Val Ser
        115

<210> SEQ ID NO 44
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC7: Heavy chain variable domain of
      anti-alpha2-integrin mAb with grafted mutations

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Ile
        35                  40                  45

Gly Arg Ile Asp Pro Ser Asp Ser Glu Thr His Tyr Ala Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Val Gly Arg Gly Tyr Phe Asp Tyr Trp Gly Gln Gly Thr Leu
            100                 105                 110

Val Thr Val Ser Ser
     115

<210> SEQ ID NO 45
<211> LENGTH: 717
<212> TYPE: DNA
<213> ORGANISM: Mus musculus

<400> SEQUENCE: 45

| | | | | | | |
|---|---|---|---|---|---|---|
| atggagacag | acacactcct | gctatgggtg | ctgctgctct | gggttccagg | ttccacaggt | 60 |
| aacattgtgc | tgacccaatc | tccagcttct | ttggctgtgt | ctctagggca | gagggccacc | 120 |
| atatcctgca | gagccagtga | aagtgttgag | agttatggca | cagttttat | ttactggtac | 180 |
| cagcagaaac | caggacaggc | acccaaactc | ctcatctatc | ttgcatccaa | cctagcatct | 240 |
| ggggtccctg | ccaggttcag | tggcagtggg | tctaggacag | acttcaccct | caccattgat | 300 |
| cctgtggagg | ctgatgatgc | tgcaacctat | tactgtcagc | aaaataatga | ggatccgtac | 360 |
| acgttcggag | gggggaccaa | gctggaaata | aaacgggctg | atgctgcacc | aactgtatcc | 420 |
| atcttcccac | catccagtga | gcagttaaca | tctggaggtg | cctcagtcgt | gtgcttcttg | 480 |
| aacaacttct | accccaaaga | catcaatgtc | aagtggaaga | ttgatggcag | tgaacgacaa | 540 |
| aatggcgtcc | tgaacagttg | gactgatcag | gacagcaaag | acagcaccta | cagcatgagc | 600 |
| agcaccctca | cgttgaccaa | ggacgagtat | gaacgacata | acagctatac | ctgtgaggcc | 660 |
| actcacaaga | catcaacttc | acccattgtc | aagagcttca | acaggaatga | gtgctag | 717 |

<210> SEQ ID NO 46
<211> LENGTH: 1401
<212> TYPE: DNA
<213> ORGANISM: Mus musculus

<400> SEQUENCE: 46

| | | | | | | |
|---|---|---|---|---|---|---|
| atgggatgga | gctgtatcat | cctcttcttg | gtagcaacag | ccacaggtgt | ccactcccag | 60 |
| gtccaactgc | atcagcctgg | ggctgaactt | gtgaagcctg | gggctccagt | gaagctgtcc | 120 |
| tgcaaggctt | ctggctacac | cttcaccagc | tactggatga | actgggtgaa | gcagaggcct | 180 |
| ggacgaggcc | tcgagtggat | tggcaggatt | gatccttccg | atagtgaaac | tcactacaat | 240 |
| caaaagttca | aggacaaggc | cacactgact | gtagacaaat | cctccagcac | agcctacatc | 300 |
| caactcagca | gcctgacatc | tgaggactct | gcggtctatt | actgtgcaaa | ggtgggacgg | 360 |
| gggtactttg | actactgggg | ccaaggcacc | actctcacag | tctcctcagc | taaaacaaca | 420 |
| gccccatcgg | tctatccact | ggcccctgtg | tgtggagata | caactggctc | ctcggtgact | 480 |
| ctaggatgcc | tggtcaaggg | ttatttccct | gagccagtga | ccttgacctg | gaactctgga | 540 |
| tccctgtcca | gtggtgtgca | caccttccca | gctgtcctgc | agtctgacct | ctacaccctc | 600 |
| agcagctcag | tgactgtaac | ctcgagcacc | tggcccagcc | agtccatcac | ctgcaatgtg | 660 |
| gcccacccgg | caagcagcac | caaggtggac | aagaaaattg | agcccagagg | gcccacaatc | 720 |
| aagccctgtc | ctccatgcaa | atgcccagca | cctaacctct | tgggtggacc | atccgtcttc | 780 |
| atcttccctc | caaagatcaa | ggatgtactc | atgatctccc | tgagccccat | agtcacatgt | 840 |
| gtggtggtgg | atgtgagcga | ggatgaccca | gatgtccaga | tcagctggtt | tgtgaacaac | 900 |
| gtggaagtac | acacagctca | gacacaaacc | catagagagg | attacaacag | tactctccgg | 960 |
| gtggtcagtg | ccctccccat | ccagcaccag | gactggatga | gtggcaagga | gttcaaatgc | 1020 |
| aaggtcaaca | acaaagacct | cccagcgccc | atcgagagaa | ccatctcaaa | acccaaggg | 1080 |

```
tcagtaagag ctccacaggt atatgtcttg cctccaccag aagaagagat gactaagaaa    1140
caggtcactc tgacctgcat ggtcacagac ttcatgcctg aagacattta cgtggagtgg    1200
accaacaacg ggaaaacaga gctaaactac aagaacactg aaccagtcct ggactctgat    1260
ggttcttact tcatgtacag caagctgaga gtggaaaaga gaactgggt ggaaagaaat     1320 agctactcct gttcagtggt ccacgagggt ctgcacaatc accacacgac taagagcttc    1380
tcccggactc ccgggaagtg a                                               1401
```

<210> SEQ ID NO 47
<211> LENGTH: 218
<212> TYPE: PRT
<213> ORGANISM: Mus musculus

<400> SEQUENCE: 47

```
Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ser Tyr
            20                  25                  30

Gly Asn Ser Phe Ile Tyr Trp Tyr Gln Gln Lys Pro Gly Gln Ala Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 48
<211> LENGTH: 447
<212> TYPE: PRT
<213> ORGANISM: Mus musculus

<400> SEQUENCE: 48

```
Gln Val Gln Leu His Gln Pro Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45
```

Gly Arg Ile Asp Pro Ser Asp Ser Glu Thr His Tyr Asn Gln Lys Phe
 50                  55                  60

Lys Asp Lys Ala Thr Leu Thr Val Asp Lys Ser Ser Thr Ala Tyr
 65                  70                  75                  80

Ile Gln Leu Ser Ser Leu Thr Ser Glu Asp Ser Ala Val Tyr Tyr Cys
                 85                  90                  95

Ala Lys Val Gly Arg Gly Tyr Phe Asp Tyr Trp Gly Gln Gly Thr Thr
             100                 105                 110

Leu Thr Val Ser Ser Ala Lys Thr Thr Ala Pro Ser Val Tyr Pro Leu
             115                 120                 125

Ala Pro Val Cys Gly Asp Thr Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
            435                 440                 445

<210> SEQ ID NO 49
<211> LENGTH: 111
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IGLKV79_IGLKJ2

<400> SEQUENCE: 49

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro Tyr Thr Phe Gly Gln Gly Thr Lys Leu Glu Ile Lys
            100                 105                 110

<210> SEQ ID NO 50
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IGHV11_IGHD33_IGHJ8

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Thr Gly Tyr Phe Asp Tyr Trp Gly Gln Gly Thr Leu Val
            100                 105                 110

Thr Val Ser Ser
        115

<210> SEQ ID NO 51
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Vk1LC

<400> SEQUENCE: 51
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Leu Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105
```

<210> SEQ ID NO 52
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Vh1b

<400> SEQUENCE: 52

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Lys Ser Ser Ser Thr Ala Tyr
65              70                  75                  80

Met Glu Leu Ser Ser Leu Arg Ser Glu Asp Thr Ala Val Tyr Tyr Cys
                85                  90                  95

Ala Arg Trp Gly Tyr Asp Tyr Asp Val Phe Tyr Tyr Ala Met Asp Tyr
            100                 105                 110

Trp Gly Gln Gly Thr Leu Val Thr Val Ser Ser
        115                 120
```

<210> SEQ ID NO 53
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain variable domain of anti-integrin 2
      mAb

<400> SEQUENCE: 53

```
Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30
```

His Trp Tyr Gln Gln Lys Pro Asp Gln Ala Pro Lys Lys Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 54
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain variable domain of anti-integrin 2
      mAb

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
 50                  55                  60

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56
```

```
Gly Gly Gly Gly Ser Gly Gly Gly Gly Ser Gly Gly Gly Gly Ser
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      7xHis tag

<400> SEQUENCE: 57

His His His His His His His
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 58

His His His His His His His His
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Gly Gly Ser
1               5

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Gly Gly Ser Gly Gly Gly Gly Ser
1               5                   10

<210> SEQ ID NO 61
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61 gtgcacagc                                                                9

<210> SEQ ID NO 62
<211> LENGTH: 17
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 62
gcttccacca agggccc                                                   17
```

PEPTIDE OR PEPTIDE COMPLEX BINDING TO ALPHA2 INTEGRIN AND METHODS AND USES INVOLVING THE SAME

RELATED APPLICATIONS

This application is a 35 U.S.C. §371 filing of International Application No. PCT/EP2011/064926, filed Aug. 30, 2011, which claims priority to European Patent Application No. 10305929.1, filed on Aug. 31, 2010. The entire contents of each of the above documents are incorporated herein by reference.

SEQUENCE LISTING

The instant application contains a Sequence Listing which has been submitted electronically in ASCII format and is hereby incorporated by reference in its entirety. Said ASCII copy, created on Apr. 22, 2015, is named 543398 SA9-101US_SL.txt and is 91,925 bytes in size.

The present invention relates to a peptide or peptide complex binding to α2 integrin for use in the treatment, prophylaxis or diagnosis, to one or more nucleic acid(s) coding for the peptide or peptide complex, a recombinant cell producing the peptide or peptide complex, a method for producing the peptide or peptide complex, a pharmaceutical composition comprising the peptide or peptide complex or the nucleic acid(s) for use as a medicament, a method for detecting α2 integrin and a screening method.

BACKGROUND OF THE INVENTION

Integrins are transmembrane proteins that mediate interactions between adhesion molecules on adjacent cells and/or the extracellular matrix (ECM). Integrins play diverse roles in several biological processes including cell migration during development and wound healing, cell differentiation and apoptosis. Their activities can also regulate the metastatic and invasive potential of tumor cells. They exist as heterodimers consisting of α and β subunits. Some α and β subunits exhibit specificity for one another and may be designated as a VLA (very late antigen) member. Heterodimers often preferentially bind certain cell adhesion molecules, or constituents of the ECM. Although they have no catalytic activity, integrins can be part of multimolecular signaling complexes known as focal adhesions.

Upon binding to ligands, integrins transduce intracellular signals to the cytoskeleton that modify cellular activity in response to these cellular adhesion events, referred to as outside-in signaling. Such signaling can also activate other integrin subtypes expressed on the same cell, referred to as inside-out signaling. Inside-out signaling further occurs via regulatory signals that originate within cell cytoplasm such as a disruption of the clasp between an α and β subunit, which are then transmitted to the external ligand-binding domain of the receptor. Integrins can play important roles in the cell adhesion events that control development, organ morphogenesis, physiology and pathology as well as normal tissue homeostasis, and immune and thrombotic responses, and in addition, they serve as environmental sensors for the cell.

One of the integrin heterodimers is α2β1 integrin. The α2β1 integrin is expressed on several different cell types, including endothelial and epithelial cells, fibroblasts, lymphocytes, and platelets. The ligand specificity of α2β1 varies with cell type. While it serves as a collagen receptor on platelets and fibroblasts, it can serve as both a collagen and as a laminin receptor on endothelial and epithelial cells.

α2β1 integrin is a molecule composed of an α2 integrin subunit of the family of α integrins, and a β1 integrin subunit from the family of β integrins. The sequences of α2 and β1 integrin are known in the art and are published, e.g. in Takada and Hemler J. Cell Biol. 109(1):397-407, 1989 and Argraves, W. S, J. Cell. Biol. September 105(3): 1183-90 (1987). Example sequences are denoted in FIG. 9 and further sequences can be retrieved from the National Centre for Biotechnology Information (NCBI) data base, e.g. under NCBI accession Numbers NP_002194 NM_002203, NM_002211, NP_002202 (β1 integrin isoform 1A) for homo sapiens α2 and β1 integrin, see also below.

Alternative splice variants, isoforms are known in the art, as well as sequences of non-human origin (such as rodent—mouse, rat, etc—simian or other) and represent possible alternative embodiments as long as they exhibit at least one of the known functions of α2 or β1 integrin.

The α2 subunit is a member of a subset of integrin α subunits that contain an approximately 200 amino acid domain located near the amino terminus often referred to as the I (or inserted) domain. Many I domains, including the $\alpha_2$ and integrin subunit I domain, contain an additional cation binding site, the metal ion-dependent adhesion site (MIDAS) motif. The structural characterisation of the α2 integrin I domain is published, e.g. in Dickeson et. al., J. Biol. Chemistry, 272, 7661-7668 (1997). I domains are important determinants in ligand binding. The amino acid sequence of a human α2 integrin I domain can be gained from FIG. 9, as marked in the α2 integrin sequence (SEQ ID 20).

The α2β1 integrin (very late antigen 2; VLA-2) is expressed on a variety of cell types including platelets, vascular endothelial cells, epithelial cells, activated monocytes/macrophages, fibroblasts, leukocytes, lymphocytes, activated neutrophils and mast cells. The natural ligands for α2β1 include collagen and laminin, both of which are found in extracellular matrix. The α2β1 integrin has been implicated in several biological and pathological processes including collagen-induced platelet aggregation, cell migration on collagen, cell-dependent reorganization of collagen fibers as well as collagen-dependent cellular responses that result in increases in cytokine expression and proliferation, aspects of T-cell, mast cell, and neutrophil function, aspects of delayed type hypersensitivity contact hypersensitivity and collagen-induced arthritis, mammary gland ductal morphogenesis, epidermal wound healing, and processes associated with VEGF-induced angiogenesis.

Platelets normally circulate in the blood in an inactive resting state, however, they are primed to respond rapidly at sites of injury to a wide variety of agonists. Upon stimulation, they undergo shape changes and become highly reactive with plasma proteins, such as fibrinogen and von Willebrand factor (vWf), other platelets, and the endothelial lining of the vessel wall. These interactions all cooperate to facilitate the rapid formation of a hemostatic fibrin platelet plug (Cramer, 2002 in Hemostasis and Thrombosis, $4^{th}$ edition). Upon binding ligand, platelet receptors transduce outside-in signal pathways which in turn, trigger inside-out signaling that results in activation of secondary receptors such as the platelet fibrinogen receptor, αIIbβ3 integrin, leading to platelet aggregation. Even minor activation of platelets can result in platelet thrombotic responses, thrombocytopenia and bleeding complications.

α2 integrin is the only collagen-binding integrin expressed on platelets and has been implicated to play some role in platelet adhesion to collagen and hemostasis (Santoro et al., Thromb. Haemost. 74:813-821 (1995); Vanhoorelbeke et al., Curr Drug Targets Cardiovasc. Haematol. Disord. 3(2): 125-

40 (2003); Sarratt et al., Blood 106(4): 1268-1277 (2005)). Therefore, the inactivation of alpha 2 integrin function would be desirable in order to negatively interfere with platelet aggregation. One such kind of inhibition would e.g. be an allosteric inhibition that locks the integrin in the inactive state.

Integrin/ligand interactions can facilitate leukocyte extravasations into inflamed tissues (Jackson et al., J. Med. Chem. 40:3359-3368 (1997); Gadek et al., Science 295(5557):1086-9 (2002), Sircar et al., Bioorg. Med. Chem. 10:2051-2066 (2002)), and play a role in downstream events following the initial extravasations of leukocytes from the circulation into tissues in response to inflammatory stimuli, including migration, recruitment and activation of pro-inflammatory cells at the site of inflammation (Eble J. A., Curr Pharm Des. 11(7):867-880 (2005)).

Blocking of α2 integrin has been reported to show impact on delayed hypersensitivity responses and efficacy in a murine model of rheumatoid arthritis and a model of inflammatory bowel disease (Kriegelstein et al., J. Clin. Invest. 110(12):1773-82 (2002); de Fougerolles et al., J. Clin. Invest. 105:721-720 (2000) and attenuate endothelial cell proliferation and migration in vitro (Senger et al., Am. J. Pathol. 160(1):195-204 (2002), suggesting that the blocking of α2 integrin might prevent/inhibit abnormal or higher than normal angiogenesis, as observed in various cancers. Furthermore, in a rat colorectal cancer surgery model α2-integrin inhibition was shown to be an effective anti-metastatic (van der Bji et al, Hepatology 47(2): 532-543 (2008)). Lineage commitment of colorectal cancer cells could also be shifted away from malignant phenotype (Kirkland et al J Biol Chem 283(41): 27612-27619 (2008)). As a 2 integrin was shown to mediate the malignant phenotype in pancreatic cancer (Grzesiak and Bouvet, Br J Cancer 94: 1311-1319 (2006) validating this target for a therapeutic approach in this type of aggressive cancer. Moreover, α2β1 integrin is interacting with glycosphingolipids in the progression of prostate cancer suggesting that blockade of this interaction will be of therapeutic use for this type of cancer (van Slambrouck et al., Int J Onco 35: 693-699 (2009). In experimental autoimmune encephalitis (EAE), a murine model of multiple sclerosis (MS), α2 integrin seems to play an important role as treatment with an anti-α2 antibody, given immediately after the onset of the disease, suppressed clinical signs and inflammation of the CNS (Tsunoda et al Brain Pathol 17:45-55 (2007). The mechanism of this therapeutically beneficial action of the anti-α2 antibody is most likely due to the inhibition of the interaction of α2β1 integrin with C1q complement protein. This interaction is a first step in mast-cell-degranulation and mast-cell activation, which is involved in autoimmune and inflammatory diseases, like MS, systemic lupus erythematosus, glomerolonephritis (McCall-Culbreath et al Blood 111 (3562-3570) 2008).

Thus, α2 integrin is an interesting medical target. As integrins are difficult targets for the development of specific inhibitors, and in view of the many different possible therapeutic indications, there is a need for alternative inhibitors binding to α2 integrin, especially inhibitors of alpha 2 integrin exhibiting somewhat different properties when compared with existing α2 integrin inhibitors, which can be used in the treatment of α2 integrin-associated disorders.

SUMMARY OF THE INVENTION

The present invention relates to a α2 integrin antibodies, antigen binding fragments and other binding molecules for use in the treatment, prophylaxis or diagnosis, to one or more nucleic acid(s) coding for the binding molecule, a recombinant cell producing the binding molecule, a method for producing the binding molecule, a pharmaceutical composition comprising the binding molecule or the nucleic acid(s) for use as a medicament, a method for detecting α2 integrin and a screening method.

To this end, a monoclonal antibody against α2 integrin has been generated and tested for its characteristics. It provides for the advantageous characteristics as described in the examples. Particularly, the anti-α2 integrin antibody and monovalent fragments or derivatives thereof have been characterized by a set of experimental data including binding constants, cross-reactivity, domain mapping and in vitro functional data.

It has been found that the monoclonal antibody (mAb) binds to the I-domain of α2-integrin with nM affinities, wherein the binding obviously occurs at an epitope within the I domain that is different from the epitope bound by a comparator antibody of the state of the art that also targets the alpha 2 integrin I domain. All engineered molecules of the antibody according to present invention (IgG4 mAb, Fab) show comparable on- and off-rates in Biacore experiments. They display cross-reactivity to primate α2β1 integrin, whereas no cross-reactivity has been detected against mouse, rat, dog, guinea pig, pig or rabbit α2β1 integrin as tested with platelets from the relevant species.

The tested molecules inhibit the interaction of recombinant α2 integrin with collagen in vitro with low nM $IC_{50}$ values. In addition to the inhibition of collagen, the anti-α2β1 integrin mAB or Fab fragments are able to inhibit platelet adhesion to collagen both in isolated human platelets and human platelet-rich plasma under static conditions. They are also able to inhibit the thrombus formation under flow on a collagen coated surface. The ability to block collagen binding and thus preventing platelet adhesion to collagen is one of the earliest steps in thrombus formation.

Finally, the mAb or Fabs did not cause platelet activation as no increase in GPIIbIIIa activation or P-selectin surface expression observed in ~30 donors for the mAb. Accordingly, the present invention provides monovalent antibodies, antibody fragments or derivatives and their uses to manufacture research, diagnostic and therapeutic agents for the treatment of α2-integrin related disorders as listed below; specific examples include thrombosis, other vascular diseases, cancer and pathological consequences of neo-angiogenesis, autoinflammatory diseases such as multiple sclerosis.

As known to the skilled person, binding characteristics of antibodies are mediated by the variable domains. For binding to an antigen, a variable domain from the heavy chain and a co-acting variable domain from the light chain are usually present in antibodies and arranged in order to allow for the co-action. The variable domain is also referred to as the FV region. More specifically, variable loops, three each on the light (VL) and heavy (VH) chain, are responsible for binding to the antigen. These loops are referred to as the Complementarity Determining Regions (CDRs), LCDR1, LCDR2 and LCDR3 for VL and HCDR1, HCDR2 and HCDR3 for VH. A variety of different arrangements of variable domain from the heavy chain and a co-acting variable domain from the light chain are known in the art. Therefore, it was important to identify one or more suitable variable domains from the heavy chain and one or more co-acting variable domains from the light chain. By sequence alignment, the CDRs of the heavy and light chains have been identified for the α2 integrin antibody specified above.

In a first aspect, present invention relates to a peptide or peptide complex, preferably an isolated monoclonal antibody or antigen binding fragment thereof, wherein said peptide or peptide complex, antibody or fragment specifically binds to the I-domain of a human α2-integrin, said antibody or fragment comprising a heavy chain variable region (VH) domain and a light chain variable region (VL) domain, wherein said antibody or fragment cross-reacts with a non-human primate α2-integrin but does not cross-react with a non-primate α2-integrin.

In a second aspect, present invention relates to a peptide or peptide complex, preferably an isolated monoclonal antibody or antigen binding fragment thereof, wherein said peptide or peptide complex, antibody or fragment specifically binds to the I-domain of a human α2-integrin, said antibody comprising a heavy chain variable region (VH) domain and a light chain variable region (VL) domain, wherein said antibody or fragment competes with a reference antibody for binding to the epitope of the reference antibody, said reference antibody comprising a light chain encoded by the plasmid as deposited with the DSMZ under accession No. DSM 23944 and a heavy chain encoded by either (i) the plasmid as deposited with the DSMZ under accession DSM 23946 or (ii) the plasmid as deposited with the DSMZ under accession No. DSM 23945.

In a third aspect the present invention relates to a peptide or peptide complex comprising one or more of the following components a to f:
(a) LCDR1, wherein LDR1 is RASESVESYGNSFIY (SEQ ID NO:6) or a functionally active variant thereof,
(b) LCDR2, wherein LDR2 is LASNLAS (SEQ ID NO:7) or a functionally active variant thereof,
(c) LCDR3, wherein LDR3 is QQNNEDPYT (SEQ ID NO:8) or a functional active variant thereof,
(d) HCDR1, wherein HDR1 is (GYTFTSYWMN, SEQ ID NO:3) or a functionally active variant thereof,
(e) HCDR2, wherein HDR2 is RIDPSDSETHYNQKFK (SEQ ID NO:4) or a functionally active variant thereof, and
(f) HCDR3, wherein HDR3 is VGRGYFDY (SEQ ID NO:5) or a functional active variant thereof,
and wherein the one or more of the components a) to f) are arranged to allow for binding of the peptide or peptide complex to α2 integrin.

In a fourth aspect, present invention relates to the above peptide or peptide complex for use in the treatment, prophylaxis or diagnosis of an α2-integrin-related disorder or disease.

In a fifth aspect, present invention relates to one or more nucleic acid(s) coding for the peptide or peptide complex of present invention.

In a sixth aspect, present invention relates to a cell heterologously expressing one of the nucleic acids of present invention.

In a seventh aspect, present invention relates to a method for producing a peptide or peptide complex of present invention comprising culturing the cell according to present invention under conditions permitting expression of the peptide or peptide complex and optionally recovering the peptide or peptide complex from the host cell.

In an eighth aspect, present invention relates to a pharmaceutical composition comprising at least one peptide or peptide complex of present invention and/or at least one nucleic acid of present invention for use as a medicament.

In a ninth aspect, present invention relates to a method of diagnosing a disease associated with altered α2 integrin, the method comprising
a) contacting a sample comprising α2 integrin with the peptide or peptide complex of any of claims 1 to 3; and
b) detecting binding of α2 integrin to the peptide or peptide complex; and
c) comparing the binding of step b) with a reference, wherein a altered α2 integrin binding in the sample relative to the reference is indicative of the disease.

In a tenth aspect, present invention relates to an article of manufacture comprising
a) a packaging material,
b) a peptide or peptide complex according to one of the claims 1-3 or a pharmaceutically acceptable salt thereof,
c) a label or a package insert, the insert contained within said packaging material, indicating that said peptide or peptide complex is effective for treatment of a disease or disorder, especially an α2 integrin-related disease disorder.

In a eleventh aspect, present invention relates to a diagnostic kit for the diagnosis of an α2-integrin related disorder or disease comprising a peptide or peptide complex of present invention and a suitable packaging, and possibly suitable instructions for using said peptide or peptide complex in the detection of α2 integrin.

In a twelfth aspect, present invention relates to a method of treatment or diagnosis of an α2 integrin-related disorder or disease using one or more peptide or peptide complexes of present invention and/or one or more nucleic acids of present invention or one of the pharmaceutical compositions of present invention.

In an thirteenth aspect, present invention relates to a method of diagnosing a disease associated with altered α2 integrin, the method comprising
a) contacting a taken sample of an individual with the peptide or peptide complex of present invention; and
b) detecting binding of α2 integrin to the peptide or peptide complex; and
c) comparing the binding of step b) with the binding of α2 integrin to the peptide or peptide complex in one or more reference samples,
wherein an altered binding in the taken sample relative to the binding detected in the one or more reference samples is indicative of the disease.

In certain embodiments, the present invention relates to an isolated monoclonal antibody or antigen binding fragment thereof, wherein said antibody or fragment specifically binds to the I-domain of a human α2-integrin, said antibody or fragment comprising a heavy chain variable region (VH) domain and a light chain variable region (VL) domain, wherein said antibody or fragment cross-reacts with a non-human primate α2-integrin but does not cross-react with a non-primate α2-integrin.

In other embodiments, the present invention relates to an isolated monoclonal antibody or antigen binding fragment thereof, wherein said antibody or fragment specifically binds to the I-domain of a human α2-integrin, said antibody comprising a heavy chain variable region (VH) domain and a light chain variable region (VL) domain, wherein said antibody or fragment competes with a reference antibody for binding to the epitope of the reference antibody, said reference antibody comprising a light chain encoded by the plasmid as deposited with the DSMZ under accession No. DSM 23944 and a heavy chain encoded by either (i) the plasmid as deposited with the DSMZ under accession DSM 23946 or (ii) the plasmid as deposited with the DSMZ under accession No. DSM 23945.

In one embodiment, said antibody or fragment specifically binds to the I-domain of the human α2-integrin with nM binding affinity. In another embodiment, said antibody or fragment inhibits the interaction of the human α2-integrin with collagen in vitro, thereby inhibiting the activation of platelets due to adhesion of said platelets to said collagen.

In one embodiment, said heavy chain variable region domain comprising the heavy chain HCDR3 of SEQ ID NO:5. In another embodiment, said heavy chain variable region domain comprises the heavy chain CDRs of SEQ ID NO:3 (HCDR1), SEQ ID NO:4 (HCDR2), and SEQ ID NO:5 (HCDR3), or functionally active variants thereof. In one embodiment, the functionally active variant of HCDR2 comprises the mutation Asp→Glu at amino acid position 6.

In one embodiment, the light chain variable region domain comprises the light chain LCDR3 of SEQ ID NO:8. In another embodiment, the light chain variable region domain comprises the light chain CDRs of SEQ ID NO:6 (LCDR1), SEQ ID NO:7 (LCDR2), and SEQ ID NO:8 (LCDR3), or functionally active variants thereof. In one embodiment, the functionally active variant of LCDR1 comprises the mutation Asn→Gln at amino acid position 11.

In one embodiment, the heavy chain variable region (VH) domain has at least 90%, 95%, 97% or 99% sequence identity to the VH sequence of SEQ ID NO: 2. In another embodiment, said heavy chain variable region (VH) domain comprises the sequence of SEQ ID NO:2 or a functionally active thereof.

In one embodiment, the light chain variable region (VL) domain has at least 90%, 95%, 97% or 99% sequence identity to the VL sequence of SEQ ID NO: 1. In another embodiment, said light chain variable region (VL) domain comprises the sequence of SEQ ID NO:1 or a functionally active thereof.

In one embodiment, the heavy chain variable region (VH) domain comprises one or more amino acid substitutions at positions selected from the group consisting of H5, H7, H11, H12, H17, H20, H38, H40, H43, H55, H61, H65, H66, H67, H76, H81, H82, H87, H91, H93, H112, H113 and H116. In one embodiment, the one or more amino acid substitutions are selected from the group consisting 5His→Val, 7Pro→Ser, 11Leu→Val, 12Val→Lys, 17Pro→Ser, 20Leu→Val, 38Lys→Arg, 40Arg→Ala, 43Arg→Gln, 55Asp→Glu, 61Asn→Ala, 65Lys→Gln, 66Asp→Gly, 67Lys→Arg, 76Ser→Thr, 81Ile→Met, 82Gln→Glu, 87Thr→Arg, 91Ser→Thr, 93Val→Lys, 112Thr→Leu, 113Leu→Val and 116Ser→Val.

In one embodiment, the light chain variable region (VL) domain comprises one or more amino acid substitutions at positions selected from the group consisting of L9, L12, L15, L22, L34, L46, L47, L80, L83, L85, L87, and L89. In one embodiment, the one or more amino acid substitutions are selected from the group consisting of 9Ala→Ser, 12Ala→Ser, 15Leu→Val, 15Leu→Pro, 22Ser→Thr, 34Asn→Gln, 46Gln→Lys, 47Ala→Pro, 80Asp→Asn, 83Glu→Gln, 85Asp→Glu, 87Ala→Thr and 89Thr→Asn.

In one embodiment, the heavy chain variable region (VH) domain has at least 90%, 95%, 97% or 99% sequence identity to a VH sequence selected from the group consisting of SEQ ID NO: 38 (HC1), SEQ ID NO:39 (HC2), SEQ ID NO:40 (HC3), SEQ ID NO:41 (HC4), SEQ ID NO:42 (HC5), SEQ ID NO:43 (HC6), and SEQ ID NO:44 (HC7). In another embodiment, the heavy chain variable region (VH) domain comprises a VH sequence selected from the group consisting of SEQ ID NO: 38 (HC1), SEQ ID NO:39 (HC2), SEQ ID NO:40 (HC3), SEQ ID NO:41 (HC4), SEQ ID NO:42 (HC5), SEQ ID NO:43 (HC6), and SEQ ID NO:44 (HC7).

In one embodiment, the light chain variable region (VL) domain has at least 90%, 95%, 97% or 99% sequence identity to a VL sequence selected from the group consisting of SEQ ID NO: 33 (LC1), SEQ ID NO:34 (LC2), SEQ ID NO:35 (LC3), SEQ ID NO:36 (LC4), and SEQ ID NO:37 (LC5). In another embodiment, the light chain variable region (VL) domain comprises a VL sequence selected from the group consisting of SEQ ID NO: 33 (LC1), SEQ ID NO:34 (LC2), SEQ ID NO:35 (LC3), SEQ ID NO:36 (LC4), and SEQ ID NO:37 (LC5).

In one embodiment, the antibody or binding portion is a chimeric antibody or humanized antibody. In another embodiment, the antigen binding portion is selected from the group consisting of a Fab, a Fab', a F(ab')2, a Fv, a disulfide linked Fv, a scFv, and a (scFv)$_2$. In another embodiment, the antibody or binding portion is selected from the group consisting of a multispecific antibody, a dual specific antibody, a isotype antibody, a dual variable domain antibody and a bispecific antibody. In another embodiment, the antibody or binding portion comprises a heavy chain immunoglobulin constant domain selected from the group consisting of: a human IgM constant domain, a human IgG1 constant domain, a human IgG2 constant domain, a human IgG3 constant domain, domain, a human IgG4 constant domain, a human IgE constant domain, and a human IgA constant domain. In one embodiment, the antibody or binding portion comprises a human IgG4 constant domain.

In another aspect, the invention provides a nucleic acid encoding the amino acid sequence of the antibody or antigen binding portion of the invention. In another aspect, the invention provides a recombinant expression vector comprising the nucleic acid. In another aspect, the invention provides a host cell comprising the recombinant expression vector. In another aspect, the invention provides a method of producing the antibody or antigen binding fragment comprising culturing the host cell under conditions such that an antibody is produced by the host cell.

In another aspect, the invention provides a pharmaceutical composition comprising the antibody, or antigen binding portion and one or more pharmaceutically acceptable carriers. In another aspect, the invention provides a method of treating, preventing or diagnosing an α2-integrin-related disorder or disease, the method comprising administering to a subject in need of thereof the pharmaceutical composition. In one embodiment, the α2 integrin-related disease or disorder is selected from the group consisting of thrombosis, a vascular disease, cancer, including neo-angiogenesis and metastasis, inflammation, inflammatory disease, autoimmune disease and a disease characterized by abnormal or increase angiogenesis, inflammatory bowel disease, Crohn's disease, ulcerative colitis, reactions to transplant, optical neuritis, spinal cord trauma, rheumatoid arthritis, systemic lupus erythematosus (SLE), multiple sclerosis, Reynaud's syndrome, experimental autoimmune encephalomyelitis, Sjorgen's syndrome, scleroderma, cardiovascular disease, psoriasis, and infections that induce an inflammatory response. In another embodiment, the α2 integrin-related disease or disorder is selected from the group consisting of acute coronary syndrome, percutaneous coronary intervention, ischemic stroke, carotid artery stenosis or peripheral arterial occlusive disease.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W., Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

Sequences: All sequences referred to herein are disclosed in the attached sequence listing that, with its whole content and disclosure, is a part of this specification.

The term "about" when used in connection with a numerical value is meant to encompass numerical values within a range having a lower limit that is 5% smaller than the indicated numerical value and having an upper limit that is 5% larger than the indicated numerical value.

The term "alpha 2 integrin" or "α2 integrin" as used herein, refers to alpha 2 integrin as known in the art, preferably human alpha 2 integrin and especially human alpha 2 integrin having the nucleic acid sequence shown in SEQ ID NO: 21 and the amino acid sequence of SEQ ID NO: 20, or a biologically active fragment thereof. The term "I domain" refers to the part of alpha 2 integrin as underlined and bold-typed in SEQ ID NO:20.

The terms "specifically binds", "specific binding" or the like, mean that the peptide or peptide complex, e.g. an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds alpha 2 integrin may, however, exhibit cross-reactivity to other antigens such as alpha 2 integrin molecules from other species. For example, in certain embodiments, the α2 integrin-specific antibodies of the invention bind to bind to both human and non-human primate α2 integrin with an affinity that is at least two-fold regater than its affinity for a non-specific antigen (e.g., a non-primate α2 integrin). Moreover, multi-specific antibodies (e.g., bispecifics) that bind to alpha 2 integrin and one or more additional antigens are nonetheless considered antibodies that "specifically bind" alpha 2 integrin, as used herein.

The term "$K_D$", as used herein, is intended to refer to the equilibrium dissociation constant of a particular peptide/peptide-complex—target molecule or antibody-antigen interaction. The equilibrium dissociation constant is typically measured in "mol/L" (abbreviated as "M").

By the term "slow off rate", "Koff" or "kd" is meant a peptide/peptide complex or antibody that dissociates from alpha 2 integrin with a rate constant of $1 \times 10^{-3}$ $s^{-1}$ or less, preferably $1 \times 10^{-4}$ $s^{-1}$ or less, as determined by surface plasmon resonance, e.g., BIACORE™.

The term "high affinity" antibody refers to those mAbs having a binding affinity to human alpha 2 integrin of at least $10^{-10}$ M; preferably $10^{-11}$ M; even more preferably $10^{-12}$ M, as measured by surface plasmon resonance, e.g., BIACORE™ or solution-affinity ELISA.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

An "epitope", also known as antigenic determinant, is the region of an antigen that is recognized by the immune system, specifically by antibodies, B cells, or T cells. As used herein, an "epitope" is the part of an antigen capable of binding to an antibody or antigen-binding fragment thereof as described herein. In this context, the term "binding" preferably relates to a "specific binding", as defined herein. Epitopes usually consist of chemically active surface groupings of molecules such as amino acids, sugar side chains, phosphoryl groups, or sulfonyl groups and may have specific three-dimensional structural characteristics and/or specific charge characteristics. Conformational and non-conformational epitopes can be distinguished in that the binding to the former but not the latter is lost in the presence of denaturing solvents.

A "paratope" is the part of an antibody that specifically binds to the epitope.

The term "antibody", as used herein, is intended to refer to immunoglobulin molecules comprised of four polypeptide chains, two heavy (H) chains and two light (L) chains interconnected by disulfide bonds. The term "antibody" also includes all recombinant forms of antibodies, in particular of the antibodies described herein, e.g. antibodies expressed in prokaryotes, unglycosylated antibodies, and any antigen-binding antibody fragments and derivatives as described below. Each heavy chain is comprised of a heavy chain variable region ("HCVR" or "VH") and a heavy chain constant region (comprised of domains CH1, $CH_2$ and CH3). Each light chain is comprised of a light chain variable region ("LCVR or "VL") and a light chain constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

With respect to the present invention, the terms alpha2 antibody, a2 antibody, α2 antibody, alpha2 integrin antibody, a2 integrin antibody, α2 integrin antibody are used synonymously and refer preferably to an inhibitory, i.e. anti-(alpha2 antibody, a2 antibody, α2 antibody, alpha2 integrin antibody, a2 integrin antibody, α2 integrin antibody).

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "antigen-binding fragment" of an antibody (or simply "binding portion"), as used herein, refers to one or more fragments of an antibody that retain the ability to specifically bind to alpha 2 integrin. It has been shown that the antigen-binding function of an antibody can be performed by fragments of a full-length antibody. Examples of binding fragments encompassed within the term "antigen-binding fragment" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies. Further examples of "antigen-binding fragments" are so-called microantibodies, which are derived from single CDRs. For example, Heap et al. describe a 17 amino acid residue microantibody derived from the heavy chain CDR3 of an antibody directed against the gp120 envelope glycoprotein of HIV-1 (Heap C J et al. (2005) J. Gen. Virol. 86:1791-1800). Other examples include small antibody mimetics comprising two or more CDR regions that are fused to each other, preferably by cognate framework regions. Such a small antibody mimetic comprising VH CDR1 and VL CDR3 linked by the cognate VH FR2 has been described by Qiu et al. (Qiu X-Q, et al. (2007) Nature biotechnology 25(8):921-929).

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen binding site derived from another species, e.g. mouse. Moreover antibodies of the invention include humanized molecules in which the antigen binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro and Fransson, the content of which is herein incorporated by reference in its entirety (Almagro J C and Fransson J (2008) Frontiers in Bioscience 13:1619-1633). Almagro and Fransson distinguish between rational approaches and empirical approaches. Rational approaches are characterized by generating few variants of the engineered antibody and assessing their binding or any other property of interest. If the designed variants do not produce the expected results, a new cycle of design and binding assessment is initiated. Rational approaches include CDR grafting, Resurfacing, Superhumanization, and Human String Content Optimization. In contrast, empirical approaches are based on the generation of large libraries of humanized variants and selection of the best clones using enrichment technologies or high-throughput screening. Accordingly, empirical approaches are dependent on a reliable selection and/or screening system that is able to search through a vast space of antibody variants. In vitro display technologies, such as phage display and ribosome display fulfill these requirements and are well-known to the skilled person. Empirical approaches include FR libraries, Guided selection, Framework-shuffling, and Humaneering.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati and Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multi specific, recombinant, heterologous, heterohybrid, chimeric, humanized (in particular CDR-grafted), deimmunized, or human antibodies, Fab fragments, Fab' fragments, F(ab')$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90(14), 6444-6448), nanobodies (also known as single domain antibodies), anti-idiotypic (anti-Id) antibodies (including, e.g., anti-Id antibodies to antibodies of the invention), and epitope-binding fragments of any of the above.

The antibodies described herein are preferably isolated. An "isolated antibody", as used herein, is intended to refer to an antibody that is substantially free of other mAbs having different antigenic specificities (e.g., an isolated antibody that specifically binds alpha 2 integrin is substantially free of mAbs that specifically bind antigens other than alpha integrin). An isolated antibody that specifically binds alpha 2 integrin may, however, have cross-reactivity to other antigens, such as alpha 2 integrin molecules from other species.

The terms "biological function or function of alpha 2 integrin" as used herein, are used synonymously and refer to any function of alpha 2 integrin such as, but not limited to: Binding to and forming a complex with beta1 integrin, binding to any of the known ligands such as binding to collagen, laminin, collagen-induced platelet aggregation, induction of thrombotic responses, thrombocytopenia, cell migration on collagen, cell-dependent reorganization of collagen fibers, collagen-dependent cellular responses resulting in increases in cytokine expression and proliferation, alpha2 integrin or collagen-dependent aspects of T-cell, mast cell or neutrophil function, alpha 2 integrin or collagen-dependent aspects of delayed type hypersensitivity, alpha 2 integrin or collagen-dependent aspects of contact hypersensitivity, collagen-induced arthritis, mammary gland ductal morphogenesis, epidermal wound healing, and processes associated with VEGF-induced angiogenesis.

As used herein, a "alpha 2 integrin antagonist" denotes a compound that inhibits at least one biological activity of alpha 2 integrin, preferably an activity of alpha 2 integrin present on blood platelets, vascular endothelial cells, epithelial cells, activated monocytes/macrophages, fibroblasts, leukocytes, lymphocytes, activated neutrophils and/or mast cells especially when used in stoichiometric amounts. Preferred alpha 2 antagonists of the present invention are neutralizing antibodies.

A "neutralizing antibody", as used herein (or an "antibody that neutralizes alpha 2 integrin activity"), is intended to refer to an antibody whose binding to alpha 2 integrin results in inhibition of at least one biological activity of alpha 2 integrin, preferably inhibition of the platelet activating activity of alpha 2 integrin. This inhibition of the biological activity of alpha 2 integrin can be assessed by measuring one or more indicators of alpha 2 integrin biological activity by one or more of several standard in vitro or in vivo assays known in the art. Examples of such assays are described for example in the examples of present invention.

Since alpha 2 integrin has functions such as listed above, the activity of alpha 2 integrin has an effect on several diseases such as those associated with increased platelet activity. Accordingly, alpha 2 integrin antagonists, such as inhibitory peptide or peptide complexes targeting alpha 2 integrin or neutralizing anti-alpha 2 integrin antibodies or antigen-binding fragments thereof, are useful to reduce or inhibit the effects of alpha 2 integrin, such as platelet activity. Consequently, alpha 2 integrin antagonists are useful for ameliorating, improving, inhibiting or preventing several such diseases, including without limitation thrombosis, a vascular disease, cancer, including neo-angiogenesis and metastasis, inflammation, inflammatory disease, autoimmune disease and a disease characterized by abnormal or increase angiogenesis, inflammatory bowel disease, Crohn's disease, ulcerative colitis, reactions to transplant, optical neuritis, spinal cord trauma, rheumatoid arthritis, systemic lupus erythematosus (SLE), multiple sclerosis, Reynaud's syndrome, experimental autoimmune encephalomyelitis, Sjorgen's syndrome, scleroderma, cardiovascular disease, psoriasis, and infections that induce an inflammatory response.

In specific embodiments, the anti-alpha 2 integrin antibodies or antigen-binding fragments thereof described herein may be conjugated to a therapeutic moiety ("immunoconjugate"), such as a cytotoxin, a chemotherapeutic drug, an immunosuppressant or a radioisotope.

A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331. Examples of groups of amino acids that have side chains with similar chemical properties include
1) aliphatic side chains: glycine, alanine, valine, leucine and isoleucine;
2) aliphatic-hydroxyl side chains: serine and threonine;
3) amide-containing side chains: asparagine and glutamine;
4) aromatic side chains: phenylalanine, tyrosine, and tryptophan;
5) basic side chains: lysine, arginine, and histidine;
6) acidic side chains: aspartate and glutamate, and
7) sulfur-containing side chains: cysteine and methionine.

Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-45. A "moderately conservative" replacement is any change having a nonnegative value in the PAM250 log-likelihood matrix. Given the known genetic code, and recombinant and synthetic DNA techniques, the skilled scientist can readily construct DNAs encoding conservative amino acid variants.

As used herein, "non-conservative substitutions" or "non-conservative amino acid exchanges" are defined as exchanges of an amino acid by another amino acid listed in a different group of the seven standard amino acid groups 1) to 7) shown above.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions which are not identical differ by conservative amino acid substitutions.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

When percentages of sequence identity are referred to in the present application, these percentages are calculated in relation to the full length of the longer sequence, if not specifically indicated otherwise. This calculation in relation to the full length of the longer sequence applies both to nucleic acid sequences and to polypeptide sequences.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in subject.

As used herein, the expressions "is for administration" and "is to be administered" have the same meaning as "is prepared to be administered". In other words, the statement that an active compound "is for administration" has to be understood in that said active compound has been formulated and made up into doses so that said active compound is in a state capable of exerting its therapeutic activity.

The terms "therapeutically effective amount" or "therapeutic amount" are intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage a patient receives can be selected so as to achieve the amount of peptide or peptide complex to exhibit sufficient inhibition of alpha2 integrin function in order to allow for the prophylactic or curative therapy (prevention, improvement or healing) of an α2 integrin-related disease or disorder, preferably selected from the group consisting of thrombosis, a vascular disease, cancer, including neo-angiogenesis and metastasis, inflammation, inflammatory disease, autoimmune disease and a disease characterized by abnormal or increase angiogenesis, inflammatory bowel disease, Crohn's disease, ulcerative colitis, reactions to transplant, optical neuritis, spinal cord trauma, rheumatoid arthritis, systemic lupus erythematosus (SLE), multiple sclerosis, Reynaud's syndrome, experimental autoimmune encephalomyelitis, Sjorgen's syndrome, scleroderma, cardiovascular disease, psoriasis, and infections that induce an inflammatory response.

As used herein, a "patient" means any mammal or bird who may benefit from a treatment with the antibodies and antigen-biding fragments thereof described herein. Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including chimpanzees and human beings. It is particularly preferred that the "patient" is a human being.

"Pharmaceutically acceptable" means approved by a regulatory agency of the Federal or a state government or listed in the U.S. Pharmacopeia (United States Pharmacopeia-33/National Formulary-28 Reissue, published by the United States Pharmacopeial Convention, Inc., Rockville Md., publication date: April 2010) or other generally recognized pharmacopeia for use in animals, and more particularly in humans.

Specific populations treatable by the therapeutic methods of the invention include subjects indicated for alpha 2 integrin-activating mutations (gain of function mutations, "GOF"), subjects with α2 integrin-related disease or disorder, preferably selected from the group consisting of thrombosis, a vascular disease, cancer, including neo-angiogenesis and metastasis, inflammation, inflammatory disease, autoimmune disease and a disease characterized by abnormal or increase angiogenesis, inflammatory bowel disease, Crohn's disease, ulcerative colitis, reactions to transplant, optical neuritis, spinal cord trauma, rheumatoid arthritis, systemic lupus erythematosus (SLE), multiple sclerosis, Reynaud's syndrome, experimental autoimmune encephalomyelitis, Sjorgen's syndrome, scleroderma, cardiovascular disease, psoriasis, and infections that induce an inflammatory response.

EMBODIMENTS OF THE INVENTION

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

Accordingly, a first aspect of the present invention relates to a peptide or peptide complex, preferably an isolated monoclonal antibody or antigen binding fragment thereof, wherein said peptide or peptide complex, antibody or fragment specifically binds to the I-domain of a human α2-integrin, said antibody or fragment comprising a heavy chain variable region (VH) domain and a light chain variable region (VL) domain, wherein said antibody or fragment cross-reacts with a non-human primate α2-integrin but does not cross-react with a non-primate α2-integrin.

A second aspect of the present invention relates to a peptide or peptide complex, preferably an isolated monoclonal antibody or antigen binding fragment thereof, wherein said peptide or peptide complex, antibody or fragment specifically binds to the I-domain of a human α2-integrin, said antibody comprising a heavy chain variable region (VH) domain and a light chain variable region (VL) domain, wherein said antibody or fragment competes with a reference antibody for binding to the epitope of the reference antibody, said reference antibody comprising a light chain encoded by the plasmid as deposited with the DSMZ under accession No. DSM 23944 and a heavy chain encoded by either (i) the plasmid as deposited with the DSMZ under accession DSM 23946 or (ii) the plasmid as deposited with the DSMZ under accession No. DSM 23945.

In a third aspect, present invention relates to a peptide or peptide complex, wherein the peptide or peptide complex comprises one or more of the following components a to f:
LCDR1, wherein LCDR1 is RASESVESYGNSFIY (SEQ ID NO:6) or a functionally active variant thereof,
LCDR2, wherein LCDR2 is LASNLAS (SEQ ID NO:7) or a functionally active variant thereof,
LCDR3, wherein LCDR3 is QQNNEDPYT (SEQ ID NO:8) or a functional active variant thereof,
HCDR1, wherein HCDR1 is GYTFTSYWMN (SEQ ID NO:3) or a functionally active variant thereof,
HCDR2, wherein HCDR2 is RIDPSDSETHYNQKFK (SEQ ID NO:4) or a functionally active variant thereof, and
HCDR3, wherein HCDR3 is VGRGYFDY (SEQ ID NO:5) or a functional active variant thereof, and wherein the one or more components a) to f) are arranged to allow for binding of the peptide or peptide complex to α2 integrin or as heterodimeric α2β1 integrin.

In a fourth aspect, present invention relates to the above peptide or peptide complex for use in the treatment, prophylaxis or diagnosis of an α2-integrin-related disorder or disease.

The sequences of SEQ ID NO:6 to 8 are CDRs of light chains and that of SEQ ID NO:3 to 5 are the CDRs of heavy chains of the analysed antibody (as determined by sequence analysis). In accordance with the present invention, the peptide or peptide complex, comprises one of above the light chain CDRs or a functionally active variant thereof and/or one of the heavy chain CDRs or a functionally active variant thereof. Examples include a peptide or peptide complex comprising one or two or three of the above HCDRS and/or one or two or three of the above LCDRs in any of the conceivable combinations. One embodiment of present invention is a peptide or peptide complex comprising 3 LCDRs and 3HCDRs, wherein at least one of them is one of the above CDRs a to f.

In the context of present invention, the terms LCDR and LDR are used synonymously. The same applies for the terms HCDR and HDR.

If the above CDRs are arranged in a suitable way, the arrangement allows for specific binding to α2 integrin. The suitable arrangement of CDRs to allow for binding of an antigen is known in the art. A variety of different antibody formats or formats of binding parameters have been developed or identified so far. Any of these or any other suitable arrangement may be used for the polypeptide or polypeptide complex of the present invention, as long as the format or arrangement allows for specific binding to α2 integrin.

The CDR sequences, as defined by the above SEQ ID NOs or variants thereof, may be arranged in one (poly)peptide-chain or in a polypeptide or peptide complex. If they are arranged within one (poly)peptide-chain, the sequences may be connected by one or more linker sequences, preferably a peptide linker, e.g. as a fusion protein. According to one embodiment, they may be embedded into a natural or artificial antibody scaffold or framework, as known in the art. For natural antibodies, the CDRs are supported within the variable domains by conserved framework regions. The framework can be modified in order to obtain artificial antibodies, such as Fabs, single chain antibodies etc. which are described below in more detail.

If CDRs are arranged in a peptide complex, two or more (poly)peptides are bound to each other by non-covalent bonding including hydrogen bonds, ionic bonds, Van der Waals forces, and hydrophobic interactions.

A peptide is an organic compound made of 2 or more α-amino acids arranged in a linear chain. The amino acids are joined together by peptide bonds between the carboxyl and amino groups of adjacent amino acid residues. In general, the genetic code specifies 20 standard amino acids. After or even during synthesis, the residues in a protein may be chemically modified by post-translational modification, which alter the physical and chemical properties, folding, stability, activity, and ultimately, the function of the proteins. The peptides according to the different aspects of present invention may be modified or unmodified as long as they are able to bind α2 integrin.

In the art, the term "polypeptide" refers to a molecule comprising about 20, about 25, about 30 or more amino acids coupled to each other by peptide bonds in a linear mode to form a polypeptide chain. Shorter molecules of this kind comprising at least 2 amino acids are generally referred to as peptides. The term "protein" usually refers to molecules comprising one or more polypeptide chains. In the context of present invention, the terms peptide, polypeptide and protein are used synonymously.

In the context of present invention, the term "peptide" or "polypeptide" according to the different aspects of present invention refers to peptides or polypeptides as defined above, and the term "peptide complex" refers to molecule complexes comprising one or more peptides and/or polypeptides as defined above (e.g., the antibodies, antigen binding fragments and other binding molecules of the invention).

Peptide and peptide complexes thereof as defined herein selectively recognize and specifically bind to a α2 integrin antigen. In the context of present invention, the term "specific binding to α2 integrin" refers to the ability of the peptide or peptide complex according to the invention to bind specifically to α2 integrin or to the α2 integrin I domain or to α2 integrin in the complex with any other polypeptide such as in the heterodimeric complex with another integrin subunit, e.g. the α2β1 integrin complex. In a preferred embodiment, the peptide or peptide complexes of present invention comprises or consists of or is an isolated monoclonal antibody or an antigen binding fragment thereof.

The use of the terms "selective" or "specific" herein, when used to describe the binding characteristics of the peptide or peptide complex according to the invention, refers to the fact that the disclosed peptides or peptide complexes do not show significant binding to other than α2 integrin, except in those specific instances where the peptide/complex is supplemented to confer an additional, distinct specificity to the α2 integrin-specific binding portion (as, for example, in bispecific or bifunctional molecules where the molecule is designed to bind or effect two functions, at least one of which is to specifically bind α2 integrin). In specific embodiments, α2 integrin-specific peptides or complexes thereof bind to human α2 integrin with a $K_D$ of at least $1.2 \times 10^{-6}$. In specific embodiments, α2 integrin-specific peptides or complexes thereof bind to human α2 integrin with a $K_D$ of $5 \times 10^{-7}$ or more, of $2 \times 10^{-7}$ or more, or of $1 \times 10^{-7}$ or more. In additional embodiments, α2 integrin-specific peptides or complexes thereof bind to human α2 integrin with a $K_D$ of $1 \times 10^{-8}$ or more. In other embodiments, α2 integrin-specific peptides or complexes thereof bind to human α2 integrin with a $K_D$ of $5 \times 10^{-9}$ or more or of $1 \times 10^{-9}$ or more. In further embodiments, α2 integrin-specific peptides or complexes thereof bind to human α2 integrin with a $K_D$ of $2 \times 10^{-10}$ or more. In specific embodiments, α2 integrin-specific peptides or complexes thereof do not bind other proteins at the above $K_D$s. In other embodiments, the α2 integrin-specific peptides or complexes thereof binding to an α2 integrin (e.g., human and/or non-human primate α2 integrin) with an affinity that is at least two-fold greater than its affinity for a non-specific antigen.

$K_D$ relates to the dissociation constant obtained from the ratio of $k_d$ (the dissociation rate of a particular binding molecule-target protein interaction; also referred to as $k_{off}$) to $k_a$ (the association rate of the particular binding molecule-target protein interaction; also referred to as $k_{on}$), or $k_d/k_a$ which is expressed as a molar concentration (M). $K_D$ values can be determined using methods well established in the art. A preferred method for determining the $K_D$ of a binding molecule is described in Example 1D.

α2 integrin-specific peptides or complexes thereof have been shown to dose-dependently inhibit α2 integrin/ligand interaction (see FIG. 2 and Examples). Accordingly, α2 integrin-specific peptides or complexes thereof may be characterized by their ability to counteract binding of collagen to α2 integrin. The extent of inhibition by any α2 integrin-specific peptide or complex thereof may be measured quantitatively in statistical comparison to a control, or via any alternative method available in the art. In specific embodiments, the inhibition is about 10% inhibition or more. In other embodiments, the inhibition is 20% or more, 30% or more, 40% or more 50% or more, 60% or more 70% or more, 80% or more, 90% or more, or 95% or more.

The peptide or peptide complex may also comprise a functionally active variant of the above sequences. A functionally active variant of the peptides or peptide complexes of the invention is characterized by having a biological activity similar to that displayed by the complete peptide, including the ability to bind to α2 integrin, and optionally to inhibit α2 integrin. The variant is functionally active in the context of the present invention, if the activity (e.g. binding activity, optionally expressed as $K_D$) of the variant amounts to 10% or more, 25% or more, 50% or more, 70% or more, 80% or more, 90% or more, 95% or more, or 99% or more of the activity of the peptide/complex without sequence alteration. Suitable methods for determining binding activity to α2 integrin are given in the Examples. A functionally active variant may be obtained by a limited number of amino acid substitutions, deletions and/or insertions.

In preferred embodiments of the present invention the peptide or peptide complex of the invention is further characterized by one or more of the following features:
(i) One, two or three components a) to c) are comprised in a variable domain of a light chain (VL)
(ii) One, two or three components d) to f) are comprised in a variable domain of a heavy chain (VH)
(iii) The peptide or peptide complex is an antibody
(iv) The peptide or peptide complex is Fab, a Fab', a F(ab')2, a Fv, a disulfide-linked Fv, a scFv, a (scFv)$_2$, a bispecific antibody, a multispecific antibody, a diabody, a triabody, a tetrabody or a minibody, a monoclonal antibody, a chimeric antibody or a humanized antibody
(v) The peptide or peptide complex comprises a heavy chain immunoglobulin constant domain selected from the group consisting of: a human IgM constant domain, a human IgG1 constant domain, a human IgG2 constant domain, a human IgG3 constant domain, domain, a human IgG4 constant domain, a human IgE constant domain, and a human IgA constant domain
(vi) The functionally active variant is a functionally active fragment consisting of 60% or more, 70% or more, 80% or more, 90% or more, 95% or more, or 99% or more of an amino acid sequence of any of SEQ ID NOS: 3 to 8;
(vii) The functionally active variant is a functionally active variant having 60% or more, 70% or more, 80% or more, 90% or more, 95% or more, or 99% or more sequence identity to an amino acid sequence of any of SEQ ID NOS: 3 to 8, particularly wherein the functionally active variant is derived from the amino acid sequence of any of SEQ ID NOS: 3 to 8 by one or more conservative amino acid substitutions
(viii) The peptide or peptide complex comprises the amino acid sequence of
SEQ ID NO: 1, or a functionally active variant thereof, and/or
SEQ ID NO: 2, or a functionally active variant thereof, and/or
SEQ ID NO:9, or a functionally active variant thereof, and/or
SEQ ID NO:10, or a functionally active variant thereof, and/or
SEQ ID NO:11, or a functionally active variant thereof, and/or
(ix) The peptide or peptide complex consists of the amino acid sequence of
SEQ ID NO: 9, or a functionally active variant thereof, and
SEQ ID NO: 10, or a functionally active variant thereof, and
optionally 50 or less additional amino acid residue(s), 1 to 40, 1 to 30, 1 to 25, 1 to 15, 1 to 10, or 5, 4, 3, 2, or 1 additional amino acids residue(s)
(x) The peptide or peptide complex consists of the amino acid sequence of
SEQ ID NO: 9, or a functionally active variant thereof, and
SEQ ID NO: 11, or a functionally active variant thereof, and
optionally 50 or less additional amino acid residue(s), 1 to 40, 1 to 30, 1 to 25, 1 to 15, 1 to 10, or 5, 4, 3, 2, or 1 additional amino acids residue(s).

SEQ ID NOs 1 and 2 can be gained from FIG. 5: SEQ ID NO: 1 is the amino acid sequence of the α2 integrin antibody-variable light chain. SEQ ID NO:2 is the amino acid sequence of the variable heavy chain, respectively.

SEQ ID NOs 9, 10 and 11 can be gained from FIG. 7: SEQ ID NO:9 is the amino acid sequence of the chimeric light chain of the antibody produced as an IgG4 format (CDRs underlined), SEQ ID NO:10 is the amino acid sequence of the chimeric heavy chain of the antibody produced as an IgG4 format (CDRs underlined), and SEQ ID NO 11 is the amino acid sequence of the chimeric heavy chain in Fab format with a 6× his tag (SEQ ID NO: 55). The constant regions were derived from human sequence backbones (see Examples). The invention also relates to any of the antibody constructs or fragments, peptide or polypeptide complexes without the his tag.

According to one embodiment, the variable domains of the HC and LC are coupled to respective constant regions and to form chimeric HC or LC constructs. Specific embodiments are a chimeric α2 integrin antibody LC variable region fused to the constant region of IGKC protein (such as e.g. in SEQ ID NO:9), a chimeric α2 integrin antibody HC variable region fused to the constant region of IGHG4 (such as e.g. in SEQ ID NO:10) or a chimeric α2 integrin antibody HC variable region fuse to the constant region CH1 domain of IGHG1 (such as e.g. in SEQ ID NO:11).

As detailed above, components a) to c) (LC CDRs) and d) to f) (HC CDRs) were obtained by sequencing variable domain of a light chain (VL) and variable domain of a heavy chain (VH), respectively, of the monoclonal antibody produced and tested. Accordingly, they may be comprised in the same. It may be any naturally occurring VL or VH framework or an artificial VL or VH framework. In one embodiment of the present invention, one or more of the CDRs (LCDR1, LCDR2, LCDR3, HCDR1, HCDR2 and HCDR3) are arranged in the framework of the prevailing variable domain, i.e. LCDR1, LCDR2 and LCDR3 in the framework of VL and HCDR1, HCDR2 and HCDR3 in the framework of VH. This means that the CDRs, as identified by any suitable method described above (cf. SEQ ID NOs: 1 and 2) alone, together or in any combination thereof, may be removed from the shown neighborhood and transferred into the framework of another (second) variable domain, thereby substituting the CDRs of the second variable domain. A variety of variable domains or antibody sequences is known in the art and may be used for this purpose. For example, variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992, Bio/Technology 10:779-783. A variable heavy domain may be paired with a variable light domain to provide an antigen binding site. In addition, independent regions (e.g., a variable heavy domain alone) may be used to bind antigen.

Combinations of the above described heavy or light chain chimeras with artificially generated light or heavy chains generated by CDR grafting as described in the previous paragraph are also conceivable as long as they show α2 integrin binding specificity.

The peptides or peptide-complexes of present invention can be glycosylated. The glycosylation of proteins and its physiological affect is known in the art. The oligosaccharide component can significantly (in the positive or negative) affect properties relevant to the efficacy of a therapeutic glycoprotein, including physical stability, resistance to protease attack, interactions with the immune system, pharmacokinetics, and specific biological activity. For the expression of glycosylated proteins, mammalian host cells are commonly used in the art (Cumming et al., 1991, Glycobiology 1: 115-130; Jenkins et al., 1996, Nature Biotechn. 14: 975-981). Examples include Chinese hamster ovary (CHO) cells, baby hamster kidney (BHK) cells, NSO- and SP2/0-mouse myeloma cells. The production of glycosylated proteins from transgenic animals has also been published (Jenkins et al., 1996, supra). Moreover, engineered recombinant host cells heterologously expressing/overexpressing glycosyl transferase genes are known in the art (Bailey, 1991, Science 252: 1668-1675). WO 9954342 (A1) discloses methods for the generation of glycosylated proteins using host cells expressing a range of a glycoprotein-modifying glycosyl transferase activity which increases complex N-linked oligosaccharides carrying bisecting GlcNAc reported to have improved function.

According to one embodiment of the present invention, the peptide or peptide complex can be coupled to one or more molecules that are not identical with the peptide or peptide complex according to present invention (additional moieties), the whole complex being a "conjugate". Examples of additional moieties comprise, e.g. one or more further biomolecules, as peptides or peptide complexes, nucleic acids (e.g. oligonucleotides, or RNA molecules, such as an RNAi) or organic (small) molecules, radioactive moieties. These additional moieties can have their own function, e.g. cytotoxicity, therapeutic activity, immunosuppressive activity, etc. or they can be beneficial for the whole conjugate for other reason (e.g. improved or decreased stability of the conjugate etc.) Present invention encompasses peptides or peptide complexes conjugated to one or more additional moieties. In the case of the peptide or peptide complex being an antibody, derivative of fragment thereof, this conjugate is an immunoconjugate. Examples of immunoconjugates are known in the art (see e.g. WO05/103081), e.g. one or more chemotherapeutic substances, prodrugs, cytotoxins, radioisotopes or radioactive nucleotides, immunosuppressive moieties, therapeutic oligonucleotides, inhibitory RNA (RNAi).

According to one embodiment, the peptide or peptide complex is an antibody. Naturally occurring antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. In the present invention, examples of suitable formats include the format of naturally occurring antibodies including antibody isotypes known as IgA, IgD, IgE, IgG and IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals. Other types of light chains, such as the ι chain, are found in lower vertebrates like Chondrichthyes and Teleostei.

In addition to naturally occurring antibodies, artificial antibody formats including antibody fragments have been developed. Some of them are described in the following. However, any other antibody format comprising or consisting of the above polypeptide(s) and allowing for specific binding to α2 integrins is encompassed by the present invention as well.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

Accordingly, the term "antibody", as used herein, means any polypeptide which has structural similarity to a naturally occurring antibody and is capable of specifically binding to α2 integrins, wherein the binding specificity is determined by the CDRs of in SEQ ID NOs: 3 to 8. Hence, "antibody" is intended to relate to an immunoglobulin-derived structure with specific binding to α2 integrin including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which selectively binds to α2 integrin and optionally inhibits the function of α2 integrin. The antibody may be any polypeptide which comprises at least one antigen binding fragment. Antigen binding fragments consist of at least the variable domain of the heavy chain and the variable domain of the light chain, arranged in a manner that both domains together are able to bind to the specific antigen.

"Full length" or "complete" antibodies refer to proteins that comprise two heavy (H) and two light (L) chains interconnected by disulfide bonds which comprise: (1) in terms of the heavy chains, a variable region and a heavy chain constant region which comprises three domains, CH1, CH2 and CH3; and (2) in terms of the light chains, a light chain variable region and a light chain constant region which comprises one domain, CL. With regard to the term "complete antibody", any antibody is meant that has a typical overall domain structure of a naturally occurring antibody (i.e. comprising a heavy chain of three or four constant domains and a light chain of one constant domain as well as the respective variable domains), even though each domain may comprise further modifications, such as mutations, deletions, or insertions, which do not change the overall domain structure.

An "antibody fragment" also contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'.

Moreover, the variable regions of the heavy and light chains can be fused together to form a single chain variable fragment (scFv).

As the first generation of full sized antibodies presented some problems, many of the second generation antibodies have comprised only fragments of the antibody. Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFV). Alternatively, disulfide-linked Fv (dsFv) fragments may be used. The binding domains of fragments can be combined with any constant domain in order to produce full length antibodies or can be fused with other proteins and polypeptides.

A recombinant antibody fragment is the single-chain Fv (scFv) fragment. In general, it has a high affinity for its antigen and can be expressed in a variety of hosts. These and other properties make scFv fragments not only applicable in medicine, but also of potential for biotechnological applications. As detailed above, in the scFv fragment the VH and VL domains are joined with a hydrophilic and flexible peptide linker, which improves expression and folding efficiency. Usually linkers of about 15 amino acids are used, of which the (Gly$_4$Ser)$_3$ linker (SEQ ID NO: 56) has been used most frequently. scFv molecules might be easily proteolytically degraded, depending on the linker used. With the development of genetic engineering techniques these limitations could be practically overcome by research focused on improvement of function and stability. An example is the generation of disulfide-stabilized (or disulfide-linked) Fv fragments where the VH-VL dimer is stabilized by an interchain disulfide bond. Cysteines are introduced at the interface between the VL and VH domains, forming a disulfide bridge, which holds the two domains together.

Dissociation of scFvs results in monomeric scFvs, which can be complexed into dimers (diabodies or (scFv)$_2$), trimers (triabodies) or larger aggregates such as T and Abs and Flexibodies.

Antibodies with two binding domains can be created either through the binding of two scFv with a simple polypeptide link (scFv)$_2$ or through the dimerisation of two monomers (diabodies). The simplest designs are diabodies that have two functional antigen-binding domains that can be either the same, similar (bivalent diabodies) or have specificity for distinct antigens (bispecific diabodies). These bispecific antibodies allow for example the recruitment of novel effector functions (such as cytotoxic T cells) to the target cells, which make them very useful for applications in medicine.

Recently, antibody formats comprising four variable domains of heavy chains and four variable domains of light chains have been developed. Examples of these include tetravalent bispecific antibodies (T and Abs and Flexibodies, Affimed Therapeutics AG, Heidelberg. Germany). In contrast to a bispecific diabody, a bispecific T and Ab is a homodimer consisting of only one polypeptide. Flexibodies are a combination of scFv with a diabody multimer motif resulting in a multivalent molecule with a high degree of flexibility for joining two molecules which are quite distant from each other on the cell surface. If more than two functional antigen-binding domains are present and if they have specificity for distinct antigens, the antibody is multispecific.

Certain antibody molecules including, but not limited to, Fv, scFv, diabody molecules or domain antibodies (Domantis) may be stabilized by incorporating disulfide bridges to line the VH and VL domains. Bispecific antibodies may be produced using conventional technologies, specific methods of which include production chemically, or from hybrid hybridomas) and other technologies including, but not limited to, the BiTE™ technology (molecules possessing antigen binding regions of different specificity with a peptide linker) and knobs-into-holes engineering.

Preferably, the antibody may be a Fab, a Fab', a F(ab')2, a Fv, a disulfide-linked Fv, a scFv, a (scFv)$_2$, a bispecific antibody, a multispecific antibody, a diabody, a triabody, a tetrabody or a minibody.

In one embodiment, the antibody is a monoclonal antibody, a chimeric antibody or a humanised antibody. Monoclonal antibodies are monospecific antibodies that are identical because they are produced by one type of immune cell that are all clones of a single parent cell. A chimeric antibody is an antibody in which at least one region of an immunoglobulin of one species is fused to another region of an immunoglobulin of another species by genetic engineering in order to reduce its immunogenicity. For example murine $V_L$ and $V_H$ regions may be fused to the remaining part of a human immunoglobulin. A particular type of chimeric antibodies is a humanised antibody. Humanised antibodies are produced by merging the DNA that encodes the CDRs of a non-human antibody with human antibody-producing DNA (or vice versa). The resulting DNA construct can then be used to express and produce antibodies that are usually not as immunogenic as the non-human parenteral antibody or as a chimeric antibody, since merely the CDRs are non-human.

According to one embodiment of the different aspects of present inventions, human or humanized antibodies or fragments thereof can be used. Accordingly, the peptide or peptide complex may comprise a heavy chain immunoglobulin constant domain selected from the group consisting of: a human IgM constant domain, a human IgG1 constant domain, a human IgG2 constant domain, a human IgG3 constant domain, domain, a human IgG4 constant domain, a human IgE constant domain, and a human IgA constant domain. In the context of the invention, the anti-α2-Integrin antibody has been humanized using a method previously described in WO2009/032661, but any suitable humanization method known in the art can be used.

As detailed above, the CDR may also be a functionally active variant of any of the CDRs specified in the claims. In one embodiment the functionally active variant is a functionally active fragment consisting of 90% or more of an amino acid sequence of any of SEQ ID NOS: 3 to 8. Alternatively, the functionally active variant is a functionally active variant having 70% or more, preferably 80% or more, more preferably 90% or 95% or more sequence identity to an amino acid sequence of any of SEQ ID NOS: 3 to 8, particularly wherein the functionally active variant is derived from the amino acid sequence of any of SEQ ID NOS: 3 to 8 by means of one or more conservative amino acid substitution (see below).

In one embodiment of the different aspects of present invention, the peptide or peptide complex comprises the amino acid sequence of
SEQ ID NO: 1, or a functionally active variant thereof, and/or
SEQ ID NO: 2, or a functionally active variant thereof and/or
SEQ ID NO: 9, or a functionally active variant thereof, and/or
SEQ ID NO: 10, or a functionally active variant thereof, and/or
SEQ ID NO: 11, or a functionally active variant thereof.

Alternatively, the peptide or peptide complex consists of the amino acid sequence of
SEQ ID NO: 9, or a functionally active variant thereof, and
SEQ ID NO: 10, or a functionally active variant thereof, and
optionally 50 additional amino acid residue(s), or 1 to 40, 1 to 30, 1 to 25, 1 to 15, 1 to 10, 1 or 2, 3, 4 or 5 additional amino acids residue(s).

Alternatively, the peptide or peptide complex consists of the amino acid sequence of
SEQ ID NO: 9, or a functionally active variant thereof, and
SEQ ID NO: 11, or a functionally active variant thereof, and
optionally 50 additional amino acid residue(s), or 1 to 40, 1 to 30, 1 to 25, 1 to 15, 1 to 10, 1 or 2, 3, 4 or 5 additional amino acids residue(s).

The functionally active variant may be a fragment characterized by being derived from any of the sequences of SEQ ID NO: 1 or 2 or 9 or 10 or 11 by one or more deletions. The deletion(s) may be C-terminally, N-terminally and/or internally. The fragment may e.g. be obtained by 10 or less deletions, such as 1, 2, 3, 4, 5, 6, 7, 8, 9 or 10, or by 5 or less, such as 1, 2, 3, 4 or 5, or by 3 or less, such as 1, 2 or 3, or by 2 or less, such as 1 or 2, or by 1 deletion(s). The functionally active fragment of the invention is characterized by having a biological activity similar to that displayed by the complete protein, including the ability to bind to α2 integrin and/or α2β1 integrin and optionally to inhibit α2 and/or α2β1 integrin. The fragment of an antigen is functionally active in the context of the present invention, if the activity of the fragment amounts to 10% or more, preferably 25% or more, more preferably 50% or more, more preferably 70% or more, more preferably 80% or more, more preferably 90% or more, more preferably 95% or more, most preferably or 99% or more of the activity of the amino acid sequence without sequence alteration. Suitable methods for determining binding activity to α2β1 integrin are given in the Examples, particularly Example 1 D.

The variant may be characterized by being derived from any of the sequences of SEQ ID NO: 1 or 2 or 9 or 10 or 11 by one or more amino acid modifications including deletions, additions and/or substitutions. The modification(s) may be C-terminally, N-terminally and/or internally. The fragment may be obtained by 10 or less deletions, such as 1, 2, 3, 4, 5, 6, 7, 8, 9 or 10, or by or less, such as 1, 2, 3, 4 or 5, or by 3 or less, such as 1, 2 or 3, or by 2 or less, such as 1 or 2, or by 1 deletion(s). The functionally active variant of the invention is characterized by having a biological activity similar to that displayed by the complete protein, including the ability to bind to α2 integrin and/or α2β1 integrin and optionally to inhibit α2 and/or α2β1 integrin. The variant is functionally active in the context of the present invention, if the activity of the variant amounts to 10% or more, preferably 25% or more, more preferably 50% or more, even more preferably 70% or more, still more preferably 80% or more, especially 90% or more, particularly 95% or more, most preferably 99% or more of the activity of the amino acid sequence without sequence alteration.

The additional amino acids of (ix, x or xi) may be C-terminally, N-terminally and/or internally located. According to one embodiment, there are 50 or less additions, or 40 or less or 30 or less or 20 or less additions or 10 or less additions such as 1, 2, 3, 4, 5, 6, 7, 8, 9 or 10, or 5 or less additions, such as 1, 2, 3, 4 or 5, or 3 or less additions, such as 1, 2 or 3, or 2 or less, such as 1 or 2, or only 1 addition(s).

The additional amino acid residue(s) may be any amino acid, which may be either an L- and/or a D-amino acid, naturally occurring and otherwise. Preferably, the amino acid is any naturally occurring amino acid such as alanine, cysteine, aspartic acid, glutamic acid, phenylalanine, glycine, histidine, isoleucine, lysine, leucine, methionine, asparagine, proline, glutamine, arginine, serine, threonine, valine, tryptophan or tyrosine.

The amino acid may also be a modified or unusual amino acid. Examples of those are 2-aminoadipic acid, 3-aminoadipic acid, β-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine N-ethylasparagine, hydroxylysine, allo-hydroxylysine, 3-hydroxyproloine, 4-hydroxyproloine, isodesmosine, allo-isoleucine, N-methylglycine, N-methylisoleucine, 6-N-Methyllysine, N-methylvaline, norvaline, norleucine or ornithine. Additionally, the amino acid may be subject to modifications such as posttranslational modifications. Examples of modifications include acetylation, amidation, blocking, formylation, γ-carboxyglutamic acid hydroxylation, glycosilation, methylation, phosphorylation and sulfatation. If more than one additional or heterologous amino acid residue is present in the peptide, the amino acid residues may be the same or different from one another.

The percentage of sequence identity can be determined e.g. by sequence alignment. Methods of alignment of sequences for comparison are well known in the art. Various programs and alignment algorithms have been described e.g. in Smith and Waterman, Adv. Appl. Math. 2: 482, 1981 or Pearson and Lipman, Proc. Natl. Acad. Sci. U.S.A. 85: 2444, 1988.

The NCBI Basic Local Alignment Search Tool (BLAST) (Altschul et al., J. Mol. Biol. 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. Variants of any of the sequences of SEQ ID NOS: 1 to 8 are typically characterized using the NCBI Blast 2.0, gapped blastp set to default parameters. For comparisons of amino acid sequences of at least 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set t default parameters (open gap 9, extension gap 1 penalties). Methods for determining sequence identity over such short windows such as 15 amino acids or less are described at the website that is maintained by the National Center for Biotechnology Information in Bethesda, Md.

In another embodiment of the different aspects of present invention, the functionally active variant, as defined above, is derived from the amino acid sequence of any of the SEQ ID NOS: 1 or 2 or 9 or 10 or 11 of any of said sequences by one or more conservative amino acid substitution.

Conservative amino acid substitutions, as one of ordinary skill in the art will appreciate, are substitutions that replace an amino acid residue with one imparting similar or better (for the intended purpose) functional and/or chemical characteristics. For example, conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Such modifications are not designed to significantly reduce or alter the binding or functional inhibition characteristics of the polypeptide (complex), albeit they may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis. The altered polypeptides are then tested for retained or better functioning using functional assays available in the art or described in the Examples. In a more preferred embodiment of the present invention the number of conservative substitutions in any of the sequences of SEQ ID NO: 1 or 2 or 9 or 10 or 20 is 20 or less such as, 20, 19, 18, 17, 16, 15, 14, 13, 12 or 11, preferably 10 or less, such as 10, 9, 8, 7 or 6, especially 5 or less, such as 5, 4, 3 particularly 2 or 1.

In yet another embodiment of the different aspects of the present invention, the peptide or peptide complex comprises one or more functionally active variants,
  wherein the functionally active variant of LDR1 comprises the mutation at amino acid position 11, particularly 11Asn→Gln;
  wherein the functionally active variant of HDR2 comprises the mutation at amino acid position 6, particularly 6Asp→Glu;
  wherein the functionally active variant of SEQ ID NO: 1 comprises one or more mutations at amino acid positions 9, 12, 15, 22, 34, 46, 47, 80, 83, 85, 87 and/or 89, preferably selected from the group consisting of 9Ala→Ser, 12Ala→Ser, (15Leu→Val, 15Leu→Pro, 22Ser→Thr, 34Asn→Gln, 46Gln→Lys, 47Ala→Pro, 80Asp→Asn, 83Glu→Gln, 85Asp→Glu, 87Ala→Thr and 89Thr→Asn, or wherein the functionally active variant of SEQ ID NO:1 comprises the following mutations (LC1), i.e. 9Ala→Ser or 15Leu→Val or 46Gln→Lys or 83Glu→Gln or 9Ala→Ser and 15Leu→Val or 9Ala→Ser and 46Gln→Lys or 9Ala→Ser and 83Glu→Gln or 15Leu→Val and 46Gln→Lys or 15Leu→Val and 83Glu→Gln or 46Gln→Lys and 83Glu→Gln or 9Ala→Ser and 15Leu→Val and 46Gln→Lys or 9Ala→Ser and 15Leu→Val and 83Glu→Gln or 9Ala→Ser and 46Gln→Lys and 83Glu→Gln or 15Leu→Val and 46Gln→Lys and 83Glu→Gln or LC1 of table 5: 9Ala→Ser and 15Leu→Val and 46Gln→Lys and 83Glu→Gln, or wherein the functionally active variant of SEQ ID NO:1 comprises the following mutations (LC2), i.e. 9Ala→Ser or 15Leu→Val or 34Asn→Gln or 46Gln→Lys or 83Glu→Gln or 9Ala→Ser and 15Leu→Val or 9Ala→Ser and 34Asn→Gln or 9Ala→Ser and 46Gln→Lys or 9Ala→Ser and 83Glu→Gln or 15Leu→Val and 34Asn→Gln or 15Leu→Val and 46Gln→Lys or 15Leu→Val and 83Glu→Gln or 34Asn→Gln and 46Gln→Lys or 34Asn→Gln and 83Glu→Gln or 9Ala→Ser and 15Leu→Val and 34Asn→Gln or 9Ala→Ser and 15Leu→Val and 46Gln→Lys or 9Ala→Ser and 15Leu→Val and 83Glu→Gln or 9Ala→Ser and 34Asn→Gln and 46Gln→Lys or 9Ala→Ser and 34Asn→Gln and 83Glu→Gln or 9Ala→Ser and 46Gln→Lys and 83Glu→Gln or 15Leu→Val and 34Asn→Gln and 46Gln→Lys or 15Leu→Val and 34Asn→Gln and 83Glu→Gln or 15Leu→Val and 46Gln→Lys and 83Glu→Gln or 34Asn→Gln and 46Gln→Lys and 83Glu→Gln or 9Ala→Ser and 15Leu→Val and 34Asn→Gln and 46Gln→Lys or 9Ala→Ser and 15Leu→Val and 34Asn→Gln and 83Glu→Gln or 9Ala→Ser and 15Leu→Val and 46Gln→Lys and 83Glu→Gln or 9Ala→Ser and 34Asn→Gln and 46Gln→Lys and 83Glu→Gln or 15Leu→Val and 34Asn→Gln and 46Gln→Lys and 83Glu→Gln or LC2 of table 5: 9Ala→Ser and 15Leu→Val and 34Asn→Gln and 46Gln→Lys and 83Glu→Gln, or wherein the functionally active variant of SEQ ID NO:1 comprises the following mutations (LC3), i.e. 9Ala→Ser or 12Ala→Ser or 15Leu→Val or 83Glu→Gln or 85Asp→Glu or 9Ala→Ser and 12Ala→Ser or 9Ala→Ser and 15Leu→Val or 9Ala→Ser and 83Glu→Gln or 9Ala→Ser and 85Asp→Glu or 12Ala→Ser and 15Leu→Val or 12Ala→Ser and 83Glu→Gln or 12Ala→Ser and 85Asp→Glu or 15Leu→Val and 83Glu→Gln or 15Leu→Val and 85Asp→Glu or 83Glu→Gln and 85Asp→Glu or 9Ala→Ser and 12Ala→Ser and 15Leu→Val or 9Ala→Ser and 12Ala→Ser and 83Glu→Gln or 9Ala→Ser and 12Ala→Ser and 85Asp→Glu or 9Ala→Ser and 15Leu→Val and 83Glu→Gln or 9Ala→Ser and 15Leu→Val and 85Asp→Glu or 9Ala→Ser and 83Glu→Gln and 85Asp→Glu or 12Ala→Ser and 15Leu→Val and 83Glu→Gln or 12Ala→Ser and 15Leu→Val and 85Asp→Glu or 12Ala→Ser and 83Glu→Gln and 85Asp→Glu or 15Leu→Val and 83Glu→Gln and 85Asp→Glu or 9Ala→Ser and 12Ala→Ser and 15Leu→Val and 83Glu→Gln or 9Ala→Ser and 12Ala→Ser and 15Leu→Val and 85Asp→Glu or 9Ala→Ser and 12Ala→Ser and 83Glu→Gln and 85Asp→Glu or 9Ala→Ser and 15Leu→Val and 83Glu→Gln and 85Asp→Glu or 12Ala→Ser and 15Leu→Val and 83Glu→Gln and 85Asp→Glu or (LC3) according to table 5: 9Ala→Ser and 12Ala→Ser and 15Leu→Val and 83Glu→Gln and 85Asp→Glu, or wherein the functionally active variant of SEQ ID NO:1 comprises the following mutations (LC4), i.e. 9Ala→Ser or 12Ala→Ser or 15Leu→Val or 34Asn→Gln or 83Glu→Gln or 85Asp→Glu or 9Ala→Ser and 12Ala→Ser or 9Ala→Ser and 15Leu→Val or 9Ala→Ser and 34Asn→Gln or 9Ala→Ser and 83Glu→Gln or 9Ala→Ser and 85Asp→Glu or 12Ala→Ser and 15Leu→Val or 12Ala→Ser and 34Asn→Gln or 12Ala→Ser and 83Glu→Gln or 12Ala→Ser and 85Asp→Glu or 15Leu→Val and 34Asn→Gln or 15Leu→Val and 83Glu→Gln or 15Leu→Val and 85Asp→Glu or 34Asn→Gln and 83Glu→Gln or 34Asn→Gln and 85Asp→Glu or 83Glu→Gln and 85Asp→Glu or 9Ala→Ser and 12Ala→Ser and 15Leu→Val or 9Ala→Ser and 12Ala→Ser and 34Asn→Gln or 9Ala→Ser and 12Ala→Ser and 83Glu→Gln or 9Ala→Ser and 12Ala→Ser and 85Asp→Glu or 9Ala→Ser and 15Leu→Val and 34Asn→Gln or 9Ala→Ser and 15Leu→Val and 83Glu→Gln or 9Ala→Ser and 15Leu→Val and 85Asp→Glu or 9Ala→Ser and 34Asn→Gln and 83Glu→Gln or 9Ala→Ser and 34Asn→Gln and 85Asp→Glu or 9Ala→Ser and 83Glu→Gln and 85Asp→Glu or 12Ala→Ser and 15Leu→Val and 34Asn→Gln or 12Ala→Ser and 15Leu→Val and 83Glu→Gln or 12Ala→Ser and 15Leu→Val and 85Asp→Glu or 12Ala→Ser and 34Asn→Gln and 83Glu→Gln or 12Ala→Ser and 34Asn→Gln and 85Asp→Glu or 12Ala→Ser and 83Glu→Gln and 85Asp→Glu or 15Leu→Val and 34Asn→Gln and 83Glu→Gln or 15Leu→Val and 34Asn→Gln and 85Asp→Glu or 15Leu→Val and 83Glu→Gln and 85Asp→Glu or 34Asn→Gln and 83Glu→Gln and 85Asp→Glu or 9Ala→Ser and 12Ala→Ser and 15Leu→Val and 34Asn→Gln or 9Ala→Ser and 12Ala→Ser and 15Leu→Val and 83Glu→Gln or 9Ala→Ser and 12Ala→Ser and 15Leu→Val and 85Asp→Glu or 9Ala→Ser and 12Ala→Ser and 34Asn→Gln and 83Glu→Gln or 9Ala→Ser and 12Ala→Ser and 34Asn→Gln and 85Asp→Glu or 9Ala→Ser and 12Ala→Ser and 83Glu→Gln and 85Asp→Glu or 9Ala→Ser and 15Leu→Val and 34Asn→Gln and 83Glu→Gln or 9Ala→Ser and 15Leu→Val and 34Asn→Gln and 85Asp→Glu or 9Ala→Ser and 15Leu→Val and 83Glu→Gln and 85Asp→Glu or 9Ala→Ser and 34Asn→Gln and 83Glu→Gln and 85Asp→Glu or 12Ala→Ser and 15Leu→Val and 34Asn→Gln and 83Glu→Gln or 12Ala→Ser and 15Leu→Val and 34Asn→Gln and 85Asp→Glu or 12Ala→Ser and 15Leu→Val and 83Glu→Gln and 85Asp→Glu or 12Ala→Ser and 34Asn→Gln and 83Glu→Gln and 85Asp→Glu or 15Leu→Val and 34Asn→Gln and 83Glu→Gln and 85Asp→Glu or 9Ala→Ser and 12Ala→Ser and 15Leu→Val and 34Asn→Gln and 83Glu→Gln or 9Ala→Ser and 12Ala→Ser and 15Leu→Val and 34Asn→Gln and 85Asp→Glu or 9Ala→Ser and 12Ala→Ser and 15Leu→Val and 83Glu→Gln and 85Asp→Glu or 9Ala→Ser and 12Ala→Ser and 34Asn→Gln and 83Glu→Gln and 85Asp→Glu or 9Ala→Ser and 15Leu→Val and 34Asn→Gln and 83Glu→Gln and 85Asp→Glu or 12Ala→Ser and 15Leu→Val and 34Asn→Gln and 83Glu→Gln and 85Asp→Glu or (LC4) according to table 5: 9Ala→Ser and 12Ala→Ser and 15Leu→Val and 34Asn→Gln and 83Glu→Gln and 85Asp→Glu, or wherein the functionally active variant of SEQ ID NO:1 comprises the following mutations (LC5), i.e. 15Leu→Pro, 22Ser→Thr, 47Ala→Pro, 80Asp→Asn, 87Ala→Thr, 89Thr→Asn or 15Leu→Pro and 22Ser→Thr or 15Leu→Pro and 47Ala→Pro or 15Leu→Pro and 80Asp→Asn or 15Leu→Pro and 87Ala→Thr or 15Leu→Pro and 89Thr→Asn or 22Ser→Thr and 47Ala→Pro or 22Ser→Thr and 80Asp→Asn or 22Ser→Thr and 87Ala→Thr or 22Ser→Thr and 89Thr→Asn or 47Ala→Pro and 80Asp→Asn or 47Ala→Pro and 87Ala→Thr or 47Ala→Pro and 89Thr→Asn or 80Asp→Asn and 87Ala→Thr or 80Asp→Asn and 89Thr→Asn or 87Ala→Thr and 89Thr→Asn or 15Leu→Pro and 22Ser→Thr and 47Ala→Pro or 15Leu→Pro and 22Ser→Thr and 80Asp→Asn or 15Leu→Pro and 22Ser→Thr and 87Ala→Thr or 15Leu→Pro and 22Ser→Thr and 89Thr→Asn or 15Leu→Pro and 47Ala→Pro and 80Asp→Asn or 15Leu→Pro and 47Ala→Pro and 87Ala→Thr or 15Leu→Pro and 47Ala→Pro and 89Thr→Asn or 15Leu→Pro and 80Asp→Asn and 87Ala→Thr or 15Leu→Pro and 80Asp→Asn and 89Thr→Asn or 15Leu→Pro and 87Ala→Thr and 89Thr→Asn or 22Ser→Thr and 47Ala→Pro and 80Asp→Asn or 22Ser→Thr and 47Ala→Pro and 87Ala→Thr or 22Ser→Thr and 47Ala→Pro and 89Thr→Asn or 22Ser→Thr and 80Asp→Asn and 87Ala→Thr or 22Ser→Thr and 80Asp→Asn and 89Thr→Asn or 22Ser→Thr and 87Ala→Thr and 89Thr→Asn or 47Ala→Pro and 80Asp→Asn and 87Ala→Thr or 47Ala→Pro and 80Asp→Asn and 89Thr→Asn or 47Ala→Pro and 87Ala→Thr and 89Thr→Asn or 80Asp→Asn and 87Ala→Thr and 89Thr→Asn or 15Leu→Pro and 22Ser→Thr and 47Ala→Pro and 80Asp→Asn or 15Leu→Pro and 22Ser→Thr and 47Ala→Pro and 87Ala→Thr or 15Leu→Pro and 22Ser→Thr and 47Ala→Pro and 89Thr→Asn or 15Leu→Pro and 22Ser→Thr and 80Asp→Asn and 87Ala→Thr or 15Leu→Pro and 22Ser→Thr and 80Asp→Asn and 89Thr→Asn or 15Leu→Pro and 22Ser→Thr and 87Ala→Thr and 89Thr→Asn or 15Leu→Pro and 47Ala→Pro and 80Asp→Asn and 87Ala→Thr or 15Leu→Pro and 47Ala→Pro and 80Asp→Asn and 89Thr→Asn or 15Leu→Pro and 47Ala→Pro and 87Ala→Thr and 89Thr→Asn or 15Leu→Pro and 80Asp→Asn and 87Ala→Thr and 89Thr→Asn or 22Ser→Thr and 47Ala→Pro and 80Asp→Asn and 87Ala→Thr or 22Ser→Thr and 47Ala→Pro and 80Asp→Asn and 89Thr→Asn or 22Ser→Thr and 47Ala→Pro and 87Ala→Thr and 89Thr→Asn or 22Ser→Thr and 80Asp→Asn and 87Ala→Thr and 89Thr→Asn or 47Ala→Pro and 80Asp→Asn and 87Ala→Thr and 89Thr→Asn or 15Leu→Pro and 22Ser→Thr and 47Ala→Pro and 80Asp→Asn and 87Ala→Thr or 15Leu→Pro and 22Ser→Thr and 47Ala→Pro and 80Asp→Asn and 89Thr→Asn or 15Leu→Pro and 22Ser→Thr and 47Ala→Pro and 87Ala→Thr and 89Thr→Asn or 15Leu→Pro and 22Ser→Thr and 80Asp→Asn and 87Ala→Thr and 89Thr→Asn or 15Leu→Pro and 47Ala→Pro and 80Asp→Asn and 87Ala→Thr and 89Thr→Asn or 22Ser→Thr and 47Ala→Pro and 80Asp→Asn and 87Ala→Thr and 89Thr→Asn or (LC5) according to table 5: 15Leu→Pro and 22Ser→Thr and 47Ala→Pro and 80Asp→Asn and 87Ala→Thr and 89Thr→Asn and/or wherein the functionally active variant of SEQ ID NO: 2 comprises one or more mutations at amino acids positions 5, 7, 11, 12, 17, 20, 38, 40, 43, 55, 61, 65, 66, 67, 76, 81, 82, 87, 91, 93, 112, 113 and/or 116, particularly selected from the group consisting of 5His→Val, 7Pro→Ser, 11Leu→Val, 12Val→Lys, 17Pro→Ser, 20Leu→Val, 38Lys→Arg, 40Arg→Ala, 43Arg→Gln, 55Asp→Glu, 61Asn→Ala, 65Lys→Gln, 66Asp→Gly, 67Lys→Arg, 76Ser→Thr, 81Ile→Met, 82Gln→Glu, 87Thr→Arg, 91Ser→Thr, 93Val→Lys, 112Thr→Leu, 113Leu→Val and 116Ser→Val or wherein the functionally active variant of SEQ ID NO:2 comprises the following mutations (HC1), i.e. 43Arg→Gln or 67Lys→Arg or 116Ser→Val or 43Arg→Gln and 67Lys→Arg or 43Arg→Gln and 116Ser→Val or 67Lys→Arg and 116Ser→Val or (HC1) according to table 6: 43Arg→Gln and 67Lys→Arg and 116Ser→Val, or wherein the functionally active variant of SEQ ID NO:2 comprises the following mutations (HC2), i.e. 43Arg→Gln or 55Asp→Glu or 67Lys→Arg or 116Ser→Val or 43Arg→Gln and 55Asp→Glu or 43Arg→Gln and 67Lys→Arg or 43Arg→Gln and 116Ser→Val or 55Asp→Glu and 67Lys→Arg or 55Asp→Glu and 116Ser→Val or 67Lys→Arg and 116Ser→Val or 43Arg→Gln and 55Asp→Glu and 67Lys→Arg or 43Arg→Gln and 55Asp→Glu and 116Ser→Val or 43Arg→Gln and 67Lys→Arg and 116Ser→Val or 55Asp→Glu and 67Lys→Arg and 116Ser→Val or (HC2) according to table 6: 43Arg→Gln and 55Asp→Glu and 67Lys→Arg and 116Ser→Val, or wherein the functionally active variant of SEQ ID NO:2 comprises the following mutations (HC3), i.e. 17Pro→Ser or 116Ser→Val or (HC3) according to table 6: 17Pro→Ser and 116Ser→Val, or wherein the functionally active variant of SEQ ID NO:2 comprises the following mutations (HC4), i.e.: 17Pro→Ser or 93Val→Lys or 116Ser→Val or 17Pro→Ser and 93Val→Lys or 17Pro→Ser and 116Ser→Val or 93Val→Lys and 116Ser→Val or (HC4) according to table 6: 17Pro→Ser and 93Val→Lys and 116Ser→Val, or wherein the functionally active variant of SEQ ID NO:2 comprises the following mutations (HC5), i.e.: 17Pro→Ser or 55Asp→Glu or 116Ser→Val or 17Pro→Ser and 55Asp→Glu or 17Pro→Ser and 116Ser→Val or 55Asp→Glu and 116Ser→Val or (HC5) according to table 6: 17Pro→Ser and 55Asp→Glu and 116Ser→Val, or wherein the functionally active variant of SEQ ID NO:2 comprises the following mutations (HC6), i.e.: 12Val→Lys or 55Asp→Glu or 93Val→Lys or 116Ser→Val or 12Val→Lys and 55Asp→Glu or 12Val→Lys and 93Val→Lys or 12Val→Lys and 116Ser→Val or 55Asp→Glu and 93Val→Lys or 55Asp→Glu and 116Ser→Val or 93Val→Lys and 55Asp→Glu and 116Ser→Val or 12Val→Lys and 55Asp→Glu and 93Val→Lys or 12Val→Lys and 55Asp→Glu and 116Ser→Val or 12Val→Lys and 93Val→Lys and 116Ser→Val or 55Asp→Glu and 93Val→Lys and 116Ser→Val or (HC6) according to table 6: 12Val→Lys and 55Asp→Glu and 93Val→Lys and 116Ser→Val, or wherein the functionally active variant of SEQ ID NO:2 comprises 1, 2, 3, 4, 5, 6, 7, 8, 9, 10, 11, 12, 13, 14, 15, 16, 17, 18, 19 or all of the following mutations (HC6) 7Pro→Ser, 11Leu→Val, 12Val→Lys, 17Pro→Ser, 20Leu→Val, 38Lys→Arg, 40Arg→Ala, 43Arg→Gln, 61Asn→Ala, 65Lys→Gln, 66Asp→Gly, 67Lys→Arg, 76Ser→Thr, 81Ile→Met, 82Gln→Glu, 87Thr→Arg, 91Ser→Thr, 112Thr→Leu, 113Leu→Val.

The positions and mutations have been introduced based on the consideration described in the Examples in the context of Tables 4, 5 and 6. There may be only one mutation, or a combination of mutations, particularly any of the combinations given in Tables 4, 5 and 6. Moreover, the peptide or peptide complex may comprise one or more of the mutations of one of the variant light chains as listed above together with one or more of the variant heavy chains as listed above, e.g. comprise or consist of one of the following combinations of mutations/functional variants: LC1 and HC1, LC1 and HC2, LC1 and HC3, LC1 and HC4, LC1 and HC5, LC1 and HC6, LC1 and HC7, LC2 and HC1, LC2 and HC2, LC2 and HC3, LC2 and HC4, LC2 and HC5, LC2 and HC6, LC2 and HC7, LC3 and HC1, LC3 and HC2, LC3 and HC3, LC3 and HC4, LC3 and HC5, LC3 and HC6, LC3 and HC7, LC4 and HC1, LC4 and HC2, LC4 and HC3, LC4 and HC4, LC4 and HC5, LC4 and HC6, LC4 and HC7, LC5 and HC1, LC5 and HC2, LC5 and HC3, LC5 and HC4, LC5 and HC5, LC5 and HC6, LC5 and HC7.

Additionally, it may be desirable, to add a marker e.g. for detection or purification of the peptide or peptide complex of the invention. Suitable markers include without limitation a tag (e.g. 6 His (SEQ ID NO: 55) (or HexaHis) tag (SEQ ID NO: 55), 7 His (SEQ ID NO: 57), 8 His (SEQ ID NO: 58), GlyGlyGlyGlySer (SEQ ID NO: 59), (GlyGlyGlyGlySer)$_2$ (SEQ ID NO: 60) Strep tag, HA tag, c-myc tag or glutathione S-transferase (GST) tag), fluorescence marker (e.g. FITC, fluorescein, rhodamine, Cy dyes or Alexa), enzyme label (e.g. penicillinase, horseradish peroxidase and alkaline phosphatase), a radiolabel (e.g. $^3$H, $^{32}$P, $^{35}$S, $^{125}$I or $^{14}$C) Additionally, the polypeptide (complex) may be add to a support, particularly a solid support such as an array, bead (e.g. glass or magnetic), a fiber, a film etc. The skilled person will be able to adapt the binding molecule comprising the polypeptide or polypeptide complex of the present invention and a further component to the intended use by choosing a suitable further component.

According to another embodiment of present invention, the peptide or peptide complex exhibits one or more of the following characteristics A-E (i.e. A or B or C or D or E or A and B or A and C or A and D or A and E or B and C or B and D or B and E or C and D or C and E or A and B and C or A and B and D or A and B and E or A and C and D or A and C and E or A and D and E or B and C and D or B and C and E or B and D and E or A and B and C and D or A and B and C and E or A and B and D and E or A and C and D and E or B and C and D and E or A and B and C and D and E:

A) kinetic binding constants (as determined by surface plasmon resonance, e.g. by Biacore) according to the data provided in table 11.
B) a molecular mass for the light chain as follows: 23.73+/−0.05 kDa or 23.73 kDa (LC1) or of 23.74+/−0.05 kDa or 23.7 kDa (LC2) or 23.75+/−0.05 kDa or 23.8 kDa (LC3) or of 23.77+/−0.05 kDa or of 23.77 kDa (LC4) or of 23.79+/−0.05 kDa or 23.79 kDa (LC5) of 50.31+/−0.05 kDA and/or a molecular mass for the heavy chain as follows: 50.31 kDa (HC1) or of 50.33+/−0.05 kDA or of 50.33 kDa (HC2) or of 50.30+/−0.05 kDa or of 50.30 kDa (HC3) or of 50.33+/−0.05 kDa or of 50.33 kDa (HC4) or of 50.32+/−0.05 kDa or of 50.32 kDa (HC5) or of 50.35+/−0.05 kDa or of 50.35 kDa (HC6) or of 50.19+/−0.05 kDa or of 50.19 kDa (HC7), C) inhibition of binding of washed human platelets to collagen with an IC50 µg/ml value of <0.1, <0.09, <0.08, <0.07, <0.06, <0.05, <0.04, <0.03, <0.02 or <0.01 as determined under static conditions, D) inhibition of binding of human platelets from platelet-rich plasma to collagen with an IC50 µg/ml of <0.3, <0.2, <0.1, <0.15, <0.14 or <0.13 as determined under static conditions, E) an aggregation percentage as determined by size exclusion chromatography of <10, <9, <8, <7, <6, <5, <4, <3, <2.5, <2, <1.5, <1 or <0.5%.

In a fifth aspect, the present invention relates to one or more nucleic acid(s) coding for the peptide or peptide complex according to the present invention.

Nucleic acid molecules of the present invention may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

Additionally, the nucleic acid may contain one or more modified bases. Such nucleic acids may also contain modifications e.g. in the ribose-phosphate backbone to increase stability and half life of such molecules in physiological environments. Thus, DNAs or RNAs with backbones modified for stability or for other reasons are "nucleic acid molecule" as that feature is intended herein. Moreover, DNAs or RNAs comprising unusual bases, such as inosine, or modified bases, such as tritylated bases, to name just two examples, are nucleic acid molecule within the context of the present invention. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia. For example, nucleotide substitutions can be made which do not affect the polypeptide encoded by the nucleic acid, and thus any nucleic acid molecule which encodes an antigen or fragment or functional active variant thereof as defined above is encompassed by the present invention.

Furthermore, any of the nucleic acid molecules encoding one or more polypeptides of the invention including fragments or functionally active variants thereof can be functionally linked, using standard techniques such as standard cloning techniques, to any desired regulatory sequence, leader sequence, heterologous marker sequence or a heterologous coding sequence to create a fusion protein.

The nucleic acid of the invention may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

In another embodiment of the different aspects of the present invention, the nucleic acid(s) is/are located in a vector. A vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, Molecular Cloning. A Laboratory Manual, 2d edition, Cold Spring Harbor Laboratory, New York (1989)). In one embodiment, the vector is a viral vector. Viral vectors include, but are not limited to, retroviral and adenoviral vectors.

Suitable host cells or cell lines for transfection by this method include bacterial cells. For example, the various strains of E. coli are well-known as host cells in the field of biotechnology. Various strains of B. subtilis, Pseudomonas, Streptomyces, and other bacilli and the like may also be employed in this method. Many strains of yeast cells known to those skilled in the art are also available as host cells for expression of the peptides of the present invention. Other fungal cells or insect cells such as Spodoptera frugipedera (519) cells may also be employed as expression systems. Alternatively, mammalian cells, such as human 293 cells, Chinese hamster ovary cells (CHO), the monkey COS-1 cell line or murine 3T3 cells derived from Swiss, BALB/c or NIH mice may be used. Still other suitable host cells, as well as methods for transfection, culture, amplification, screening, production, and purification are known in the art.

In one embodiment of the different aspects of present invention, a hybridoma cell line can be used, the hybridoma cell line expressing desirable monoclonal antibodies generated by well-known conventional techniques. In the context of the present invention the hybridoma cell is able to produce an antibody specifically binding to α2 integrin, particularly to α2β1 integrin. The hybridoma cell can be generated by fusing a normal-activated, antibody-producing B cell with a myeloma cell. In particular, the hybrodoma cell may be produced as follows: B-cells are removed from the spleen of an animal that has been challenged with the relevant antigen. These B-cells are then fused with myeloma tumor cells that can grow indefinitely in culture. This fusion is performed by making the cell membranes more permeable. The fused hybrid cells (called hybridomas), being cancer cells, will multiply rapidly and indefinitely and will produce large amounts of the desired antibodies. They have to be selected and subsequently cloned by limiting dilution. Supplemental media containing Interleukin-6 (such as briclone) are usually essential for this step. Selection occurs via culturing the newly fused primary hybridoma cells in selective-media, specifically media containing 1× concentration HAT for roughly 10-14 days. After using HAT it is often desirable to use HT containing media. Cloning occurs after identification of positive primary hybridoma cells.

A peptide or peptide complex of the invention may be produced by expressing a nucleic acid of the invention in a suitable host cell. Accordingly, in another aspect, the present invention relates to a method for producing a peptide or peptide complex according to the invention comprising culturing the host cell comprising the nucleic acid(s) of the invention under conditions permitting expression of the antibody and optionally recovering the peptide or peptide complex from the host cell.

For this, host cells can be transfected, e.g. by conventional means such as electroporation with at least one expression vector containing a nucleic acid of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art. For example, the proteins are isolated in soluble form following cell lysis, or extracted using known techniques, e.g. in guanidine chloride. If desired, the polypeptide(s) of the invention are produced as a fusion protein. Such fusion proteins are those described above. Alternatively, for example, it may be desirable to produce fusion proteins to enhance expression of the protein in a selected host cell or to improve purification. The molecules comprising the polypeptides of this invention may be further purified using any of a variety of conventional methods including, but not limited to: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention. Such purification provides the antigen in a form substantially free from other proteinaceous and non-proteinaceous materials of the microorganism.

Suitable host cells are e.g. eukaryotic cells or cell lines derived from multicellular organisms (such as defined above, e.g. CHO cells or BHK cells), eukaryotic single cell organisms such as yeast (e.g. *s. pombe* or *s. cerevisiae*) or procaryotic cells such as *e. coli*. A big variety of suitable host cells is known in the art.

One embodiment of the different aspects of present invention relates to a recombinant cell producing the peptide or peptide complex, wherein the peptide or peptide complex is heterologously expressed by said cell/host cell. Heterologous expression of a peptide or protein (here: peptide or peptide complex) means that the recombinant cell is derived from a cell that does not naturally express the peptide or protein or peptide complex and which has been modified (e.g. transfected or transformed) to express it; e.g. carrying a nucleic acid (such as an artificial nucleic acid construct (a vector) carrying an insert coding for the peptide or peptide complex) allowing for the expression of said peptide or peptide complex, such as an antibody or fragment thereof, by said cell.

The recombinant cell may be derived from any cell, cell line or host cells as defined above, including eukaryotic as well as procaryotic cells.

Accordingly, a sixth aspect of present invention relates to a cell heterologously expressing one of the nucleic acids of present invention.

In a seventh aspect, present invention relates to a method for producing a peptide or peptide complex of present invention comprising culturing the cell according to present invention under conditions permitting expression of the peptide or peptide complex and optionally recovering the peptide or peptide complex from the host cell.

An eighth aspect of the present invention relates to a composition comprising at least one peptide or peptide complex or a conjugate comprising the peptide or peptide complex according the invention and/or at least one nucleic acid according to the invention for use as a medicament.

The (pharmaceutical) composition of the present invention may further encompass pharmaceutically acceptable carriers and/or excipients. The pharmaceutically acceptable carriers and/or excipients useful in this invention are conventional and may include buffers, stabilizers, diluents, preservatives, and solubilizers. Remington's Pharmaceutical Sciences, by E. W. Martin, Mack Publishing Co., Easton, Pa., 15th Edition (1975), describes compositions and formulations suitable for pharmaceutical delivery of the polypeptides/nucleic acids disclosed herein. The content of the active ingredient (polypeptide or nucleic acid) in the pharmaceutical composition is not limited as far as it is useful for treating or preventing, but preferably contains 0.0000001-10% by weight per total composition.

In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Generally, an appropriate amount of a pharmaceutically acceptable salt is used in the carrier to render the formulation isotonic. Examples of the carrier include but are not limited to saline, Ringer's solution and dextrose solution. Preferably, acceptable excipients, carriers, or stabilisers are preferably non-toxic at the dosages and concentrations employed, including buffers such as citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol).

The pharmaceutical composition encompasses at least one peptide, peptide complex or nucleic acid of the invention; however, it may also contain a cocktail (i.e., a simple mixture) containing one or more different peptides and/or peptide complexes and/or nucleic acids of the invention. The peptide(s) or peptide complex(es) of the present invention may also be used in the form of a pharmaceutically acceptable salt. Suitable acids and bases which are capable of forming salts with the peptides of the present invention are well known to those of skill in the art, and include inorganic and organic acids and bases.

Preferably, the pharmaceutical composition may be used for treating or preventing an $\alpha 2$ integrin-related disease or disorder. In the context of present invention, an 2 integrin-related disease or disorder can be understood as any unwanted condition of the body that involves, is caused, contributed to or affected by one or more of $\alpha 2$-integrin functions or activities. Examples include signaling pathways or processes involving $\alpha 2$ integrin mediating aberrant cellular reactions such as collagen-mediated increased or aberrant cellular proliferation or cytokine secretion, resulting e.g. in neo-angiogenesis, inflammatory conditions or wound healing disorders. Specific examples comprise (but are not limited to): Thrombosis, vascular disease, cancer, including neo-angiogenesis and metastasis, pancreatic cancer, colon cancer, e.g. metastatic spreading of colon cancer to other organs (e.g. lung and liver) and melanoma, inflammation, inflammatory disease, autoimmune disease and a disease characterized by abnormal or increase angiogenesis, inflammatory bowel disease, Crohn's disease, ulcerative colitis, reactions to transplant, optical neuritis, spinal cord trauma, rheumatoid arthritis, systemic lupus erythematosus (SLE), multiple sclerosis, Reynaud's syndrome, Sjorgen's syndrome, scleroderma, cardiovascular disease, psoriasis, atherosclerosis, and infections that induce an inflammatory response.

In one embodiment of the present invention, the pharmaceutical composition may be used for treating or preventing a vascular disease and/or thrombosis, particularly in the treatment of certain clinical indications, as for example acute coronary syndrome, percutaneous coronary intervention, ischemic stroke, carotid artery stenosis or peripheral arterial occlusive disease.

In the context of present invention, the treatment or prevention can affect any animal (non-human or human, especially mammals such as humans, farm animals or pet animals) in need of treatment (i.e. in order to lessen or abolish the diseased state or disorder or in order to prevent or delay the onset of the diseased state or disorder in individuals that do not yet display the diseased state or disorder).

$\alpha 2\beta 1$ integrin is an interesting target in the treatment or prevention of thrombosis. In vivo studies with $\alpha 2\beta 1$ knockout mice showed decreased thrombus formation and increased time to occlusion in arterial thrombosis models as well as prolonged tail bleeding times. In clinical studies relating to $\alpha 2$ integrin deficiency and polymorphisms, patients showed mild to severe bleeding disorder and defective collagen response of platelets. The polymorphism leads to increased expression of $\alpha 2\beta 1$, resulting in an independent risk factor for non fatal myocardial infarction in individuals <age 62, increased risk of stroke in patients <age 50, and increased risk for development of diabetic retinopathy in type II diabetics. Furthermore, platelets and $\alpha 2$ integrin are involved in angiogenesis, tumor progression/metastasis.

Accordingly, cancer is a further interesting therapeutic field. Inhibition of $\alpha 2$ integrin has been shown to antagonizes stromal tumor invasion in vitro and Integrin-ECM/$\alpha 2$ integrin-mediated type I collagen adhesion in particular is involved in the promotion of the malignant phenotype in pancreatic cancer in vitro. In vivo, anti-$\alpha 2$ antagonistic mAbs prevent operation-induced augmentation of liver metastases in a rat model inhibit differentiation of multipotent human colorectal cancer cells and suppress the growth and vascularization of human squamous cell carcinoma xenografts.

For colorectal cancer it has been shown that removal of primary colorectal carcinoma may paradoxically increase the risk of metastases development, because accumulating evidence suggests that surgical trauma can stimulate tumor growth. Manipulation of the primary tumour during surgery results in tumor cell detachment which overcomes the need of complex cellular changes. In addition, operative trauma induces exposure of subendothelial ECM and thereby facilitates binding through commonly expressed integrins, promoting tumor cell adherence. In an animal model, blocking $\alpha 2$ integrin on tumor cells completely abrogated operation-induced adhesion and completely reverted the enhanced outgrowth of liver metastases after abdominal surgery.

For pancreatic cancer, current therapy is often insufficient, because it extends life by only 4 months. Integrin-ECM and $\alpha 2\beta 1$-integrin mediated type I collagen adhesion in particular are involved in the promotion of the malignant phenotype in pancreatic cancer in vitro. Studies in animal models using inhibitors of $\alpha 2\beta 1$ integrin function such as mAbs are warranted and should be evaluated for therapeutic efficacy in the treatment of pancreatic cancer.

Based on these findings, a functional blocking of $\alpha 2$ and/or $\alpha 2\beta 1$ integrin may provide an interesting therapeutic opportunity, in particular for colorectal and pancreatic cancer.

A ninth aspect of the present invention relates to a method of diagnosing a disease associated with altered $\alpha 2$ integrin expression, the method comprising
  a) contacting a sample from a subject comprising $\alpha 2$ integrin with the peptide or peptide complex of the invention;
  b) detecting binding of $\alpha 2$ integrin to the peptide or peptide complex; and
  c) comparing the binding of step b) with a reference,
  wherein an altered $\alpha 2$ integrin binding in the sample relative to the reference is indicative of the disease. The altered binding can e.g. be identified by an altered signal (i.e. an increased or decreased signal) as detected in step b in comparison with a reference sample.

The peptide (complex) of the present invention may also be used for diagnostic assays. As detailed above altered expression of $\alpha 2$ integrin and/or mutations thereof may be associate with particular diseases. Accordingly, the peptide (complex) may be used to determine binding to $\alpha 2$ integrin. If binding (quantitatively or qualitatively) relative to a control or reference is changed, this may be indicative of a disease.

Accordingly, another aspect of present invention relates to a method of diagnosing a disease associated with altered $\alpha 2$ integrin, the method comprising
  a) contacting a taken sample of an individual with the peptide or peptide complex of present invention; and
  b) detecting binding of $\alpha 2$ integrin to the peptide or peptide complex; and
  c) comparing the binding of step b) with the binding of $\alpha 2$ integrin to the peptide or peptide complex in one or more reference samples,
  wherein an altered binding in the taken sample relative to the binding detected in the one or more reference samples is indicative of the disease.

Generally, a test sample obtained from a subject can be contacted with the peptide (complex) of the invention that specifically binds α2 integrin. Optionally, the peptide (complex) can be fixed to a solid support prior to contacting the antibody with a test sample to facilitate washing and subsequent isolation of the complex. Examples of solid supports include glass or plastic in the form of, for example, a microtiter plate, a glass microscope slide or cover slip, a stick, a bead, or a microbead.

After incubating the sample with antibodies, the mixture is washed and the peptide (complex)/α2 integrin/complexes formed can be detected. This can be accomplished by incubating the washed mixture with a detection reagent. This detection reagent may be by use of a detectable label. A variety of labels and detection methods are known to the skilled person. In terms of the detectable label, any detectable label known in the art can be used. For example, the detectable label can be a radioactive label (such as e.g., $^3$H, $^{125}$I, $^{35}$S, $^{14}$C, $^{32}$P, and $^{33}$P), an enzymatic label (such as, for example, horseradish peroxidase, alkaline phosphatase, glucose 6-phosphate dehydrogenase, and the like), a chemiluminescent label (such as, for example, acridinium esters, acridinium thioesters, acridinium sulfonamides, phenanthridinium esters, luminol, isoluminol and the like), a fluorescence label (such as, for example, fluorescein (for example, 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (for example, zinc sulfide-capped cadmium selenide), a thermometric label, a tag (as defined above) or an immuno-polymerase chain reaction label.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, biomarker (antigen), volume of solution, concentrations and the like. Usually the assays will be carried out at ambient temperature, although they can be conducted over a range of temperatures, such as 10° C. to 40° C.

As a matter of convenience, the peptide (complex) can be provided in a kit, such as a packaged combination of reagents in predetermined amounts with instructions, including for performing a diagnostic assay. Where the peptide (complex) is labeled with an enzyme, the kit will include substrates and cofactors required by the enzyme (e.g., a substrate precursor which provides the detectable chromophore or fluorophore). Other additives may be included in the kit such as stabilizers, buffers (e.g., a block buffer or lysis buffer) and the like. The relative amounts of the various reagents provided in I the kit may be varied widely, for example, to provide for concentrations in solution of the reagents which substantially optimize the sensitivity of the assay. The reagents may be provided as dry powders, usually lyophilized, including excipients, for example, which on dissolution will provide a reagent solution having the appropriate concentration.

The reference may be a sample from a healthy subject or determined at a group of healthy subjects: Alternatively, it may be a known reference value. The person skilled in the art knows statistical procedures to assess whether two values are significantly different from each other such as Student's t-test or chi-square tests. Furthermore, the skilled person knows how to select a suitable control.

The terms "sample from a subject" and "test sample" relates to all biological fluids, excretions and tissues isolated from any given subject, particularly a human. In the context of the present invention such samples include, but are not limited to, blood, blood serum, blood plasma, nipple aspirate, urine, semen, seminal fluid, seminal plasma, prostatic fluid, excreta, tears, saliva, sweat, biopsy, ascites, cerebrospinal fluid, milk, lymph, bronchial and other lavage samples, or tissue extract samples. Typically, blood samples are preferred test samples for use in the context of the present invention.

In a tenth aspect, present invention relates to an article of manufacture comprising
a) a packaging material (e.g. one or more containers for the peptide or peptide complex and the label or package insert)
b) a peptide or peptide complex of present invention or a pharmaceutically acceptable salt thereof,
c) a label (e.g. comprising written information and/or a bar code and/or any other kind of information) or a package insert (i.e. any kind of data carrier such as a chip, a leaflet, a booklet etc.), the insert contained within said packaging material indicating that said peptide or peptide complex is effective for treatment of a disease or disorder, especially an α2 integrin-related disease disorder, such as herein defined.

In an eleventh aspect, present invention relates to a diagnostic kit for the diagnosis of an α2-integrin related disorder or disease comprising a peptide or peptide complex of present invention and a suitable packaging, and possibly suitable instructions for using said peptide or peptide complex in the detection of α2 integrin.

A diagnostic kit according to the ninth aspect of present invention is an article of manufacture that comprises at least the components as defined in the ninth aspect and optionally one or more further components (e.g. buffers and other reagents necessary or suitable for carrying out the detection of alpha 2 integrin in the sample or further means for detecting alpha 2 integrin or other markers of a given disease, or negative/positive standards, one or more secondary antibodies (suitably labelled) for detecting and/or visualising and/or quantifying the alpha 2 integrin-(peptide/peptide complex) complex suitably contained within one or more suitable containers) that are preferably combined to a spatially assembled unit and that is intended for use in the diagnosis of an α2-integrin related disorder or disease According to one embodiment of the ninth aspect, the kit further comprises a data carrier comprising instructions for a method according to the seventh or eleventh aspect of present invention and any one its embodiments.

In a twelfth aspect, present invention relates to a method of treatment or diagnosis of an α2 integrin-related disorder or disease using one or more peptide or peptide complexes of present invention and/or one or more nucleic acids Accordingly, aspect of present invention relates to a method of diagnosing a disease associated with altered α2 integrin, the method comprising
   a) contacting a taken sample of an individual with the peptide or peptide complex of present invention; and
   b) detecting and/or quantifying the binding of α2 integrin to the peptide or peptide complex; and
   c) comparing the binding of step b) with the binding of α2 integrin to the peptide or peptide complex in one or more reference samples,
   wherein an altered binding in the taken sample relative to the binding detected in the one or more reference samples is indicative of the disease. The binding can be detected or quantified in terms of the affinity (e.g. KD, Koff, Kon rate) using known methods or simply by means of the signal (intensity) of the peptide/peptide-complex—alpha 2 integrin complex caused e.g. by a labelled antibody against the peptide/peptide complex in comparison to that of the reference sample.

The term "reference", especially in the context of "reference individual", "reference sample" or "reference value" in the context of present invention refers to a comparison or standard that is characteristic or representative for a certain (health) status, disease etc. Thus, a reference value, is a standard value for a certain parameter (e.g. expression level of a certain indicator/biomarker molecule) that is typical for a certain status (e.g. a disease status or health status), a reference individual is an individual that has been selected for comparison and has a certain health state or disease, a reference sample can e.g. be a sample from a reference individual or an artificial sample with a characteristic level of a certain indicator or biomarker typical for a disease state or health state.

The term "reference sample" as used herein, refers to a sample which is analysed in a substantially identical manner as the sample of interest and whose information is compared to that of the sample of interest. A reference sample thereby provides a standard allowing for the evaluation of the information obtained from the sample of interest.

A reference sample may be derived from a healthy or normal tissue, organ or individual, thereby providing a standard of a healthy status of a tissue, organ or individual. Differences between the status of the normal reference sample and the status of the sample of interest may be indicative of the risk of disease development or the presence or further progression of such disease or disorder.

A reference sample may be derived from an abnormal or diseased tissue, organ or individual thereby providing a standard of a diseased status of a tissue, organ or individual. Differences between the status of the abnormal reference sample and the status of the sample of interest may be indicative of a lowered risk of disease development or the absence or bettering of such disease or disorder.

A reference sample may also be derived from the same tissue, organ, or individual as the sample of interest but has been taken at an earlier time point. Differences between the status of the earlier taken reference sample and the status of the sample of interest may be indicative of the progression of the disease, i.e. a bettering or worsening of the disease over time. A reference sample was taken at an earlier or later time point in case a period of time has lapsed between taking of the reference sample and taking of the sample of interest. Such period of time may represent years (e.g. 1, 2, 3, 4, 5, 10, 15, 20, 25, 30, 35, 40, 45, 50, 60, 70, 80, 90, 100 years), months (1, 2, 3, 4, 5, 6, 7, 8, 9, 10, 11, 12 months), weeks (e.g. 1, 2, 3, 4, 5, 6, 7, 8 weeks), days (e.g. 1, 2, 3, 4, 5, 10, 15, 20, 25, 30, 35, 40, 45, 50, 60, 70, 80, 90, 100, 200, 300, 400, 500 days), hours (1, 2, 3, 4, 5, 6, 7, 8, 9, 10, 11, 12 hours), minutes (e.g. 1, 2, 3, 4, 5, 10, 15, 20, 25, 30, 35, 40, 45, 50, 60 minutes), or seconds (e.g. 1, 2, 3, 4, 5, 10, 15, 20, 25, 30, 35, 40, 45, 50, 60 seconds).

The reference sample representative for a status or stage of pain may be from a control subject known to suffer from the disorder or disease that is to be diagnosed, i.e. an alpha-2 integrin related disorder or disease, e.g. such as herein defined. The control subject may be a mammal such as a human, rodent (e.g. rat, hamster, or mouse) or monkey, or may be another animal than a mammal such as an avian.

Preferably, both the sample or value and the reference sample or value are from subjects of the same species (e.g. human), more preferably of the same gender (e.g. female or male) and/or of a similar age or phase of life (e.g. infant, young child, juvenile, adult, or elderly).

The reference or reference sample in the different aspects and embodiments of present invention is preferably derived from a healthy individual, a diseased individual, or from the same individual as the sample of interest. Where the reference (e.g. reference value) or reference sample was taken from the same individual as the sample of interest, the reference (e.g. reference value) or reference sample was preferably taken at an earlier or later time point then the sample of interest. The time period which has lapsed between taking of the reference (e.g. reference value) or reference sample and taking of the reference (e.g. reference value) or sample or value of interest preferably represents years (e.g. 1, 2, 3, 4, 5, 10, 15, 20, 25, 30, 35, 40, 45, 50, 60, 70, 80, 90, 100 years), months (1, 2, 3, 4, 5, 6, 7, 8, 9, 10, 11, 12 months), weeks (e.g. 1, 2, 3, 4, 5, 6, 7, 8 weeks), days (e.g. 1, 2, 3, 4, 5, 10, 15, 20, 25, 30, 35, 40, 45, 50, 60, 70, 80, 90, 100, 200, 300, 400, 500 days), hours (1, 2, 3, 4, 5, 6, 7, 8, 9, 10, 11, 12 hours), minutes (e.g. 1, 2, 3, 4, 5, 10, 15, 20, 25, 30, 35, 40, 45, 50, 60 minutes), or seconds (e.g. 1, 2, 3, 4, 5, 10, 15, 20, 25, 30, 35, 40, 45, 50, 60 seconds). Alternatively or additionally, the reference sample is a reference sample with a level of alpha 2 integrin representative for a healthy individual or representative for the presence or absence of an alpha 2 integrin related disorder or disease or representative for an increased or decreased risk of developing an alpha 2 integrin related disorder or disease.

In embodiments, wherein the reference or reference sample is derived from a healthy individual or an individual with a decreased risk of developing an alpha 2 integrin related disorder or disease or with a level of alpha 2 integrin representative of the absence of an alpha 2 integrin related disorder or disease, an elevated level of alpha 2 integrin in the reference sample or value, or in the sample or value of interest in comparison to said reference value or reference sample indicates (a) the presence of an alpha 2 integrin related disorder or disease and/or (b) an increased risk to develop an alpha 2 integrin related disorder or disease and/or (c) the progression of an alpha 2 integrin related disorder or disease in the individual. In embodiments, wherein the reference is derived from a diseased individual or an individual with an increased risk of developing an alpha 2 integrin related disorder or disease or a value representative of the presence of an alpha 2 integrin related disorder or disease, a similar level of alpha 2 integrin indicates (a) the presence of an alpha 2 integrin related disorder or disease and/or (b) an increased risk to develop an alpha 2 integrin related disorder or disease and/or (c) the progression of an alpha 2 integrin related disorder or disease in the individual.

In embodiments, wherein the reference (value) or reference sample is (from) the same individual as the individual of interest at an earlier time point, an elevated level of alpha 2 integrin in the individual/value/sample of interest indicates (a) the presence of an alpha 2 integrin related disorder or disease and/or (b) an increased risk to develop an alpha 2 integrin related disorder or disease and/or (c) the progression of an alpha 2 integrin related disorder or disease in the individual. In embodiments, wherein the reference (value) or reference sample is (from) the same individual as the individual/sample of interest at an earlier time point, a lowered level of alpha 2 integrin in the sample of interest indicates (a) an alteration of the alpha 2 integrin related disorder or disease or an improvement or absence of the alpha 2 integrin related disorder or disease and/or (b) a decreased risk to develop an alpha 2 integrin related disorder or disease and/or (c) a declined progression of the alpha 2 integrin related disorder or disease.

In embodiments, wherein the reference (value) or reference sample is (from) the same individual as the sample/value of interest at an earlier time point, a similar level of alpha 2 integrin in the sample of interest indicates (a) a similar risk to develop an alpha 2 integrin related disorder or disease and/or (b) a stagnation in the progression of an alpha 2 integrin related disorder or disease, and/or (c) a persistence of the alpha 2 integrin related disorder or disease in the individual.

In embodiments, wherein the reference (value) or reference sample is derived from a healthy individual or from an individual with a decreased risk of developing an alpha 2 integrin related disorder or disease or comprises a level of alpha 2 integrin representative of a healthy individual or of a status of disease-absence or of a decreased risk of developing an alpha 2 integrin related disorder or disease, wherein an elevated level of alpha 2 integrin indicates (a) the presence of an alpha 2 integrin related disorder or disease and/or (b) an increased risk to develop an alpha 2 integrin related disorder or disease and/or (c) the progression of an alpha 2 integrin related disorder or disease in the individual.

In embodiments, wherein the reference (value) or reference sample is derived from a diseased individual or from an individual with an increased risk of developing an alpha 2 integrin related disorder or disease or comprises a level or amount of alpha 2 integrin representative for a diseased individual or for a status of disease-presence or for an increased risk of developing an alpha 2 integrin related disorder or disease, wherein a similar level of alpha 2 integrin indicates (a) the presence of an alpha 2 integrin related disorder or disease and/or (b) an increased risk to develop an alpha 2 integrin related disorder or disease and/or (c) the progression of an alpha 2 integrin related disorder or disease in the individual.

In embodiments, wherein the reference (value) or sample is derived from the same individual as sample of interest and was taken at an earlier time point, an elevated level of alpha 2 integrin in the sample of interest indicates (a) the presence of an alpha 2 integrin related disorder or disease and/or (b) an increased risk to develop an alpha 2 integrin related disorder or disease and/or (c) the progression of an alpha 2 integrin related disorder or disease in the individual.

In embodiments, wherein the reference (value) or reference sample is derived from the same individual as sample of interest and was taken at an earlier time point, a lowered level of alpha 2 integrin in the sample of interest indicates (a) an alteration of the alpha 2 integrin related disorder or disease or an improvement or absence of an alpha 2 integrin related disorder or disease and/or (b) a decreased risk to develop an alpha 2 integrin related disorder or disease and/or (c) a declined progression of the alpha 2 integrin related disorder or disease. In embodiments, wherein the reference sample is derived from the same individual as sample of interest and was taken at an earlier time point, a similar level of alpha 2 integrin in the sample of interest indicates (a) a similar risk to develop an alpha 2 integrin related disorder or disease and/or (b) a stagnation in the progression of an alpha 2 integrin related disorder or disease, and/or (c) a persistence of the alpha 2 integrin related disorder or disease in the individual.

According to a preferred embodiment of the different aspects of present invention, the peptide or peptide complex comprises or consists of (is) an isolated monoclonal antibody or antigen binding fragment thereof. In the following, some preferred embodiments relating to an isolated monoclonal antibody or antigen-binding fragment thereof are listed:

1. Isolated monoclonal antibody or antigen binding fragment thereof, wherein said antibody or fragment specifically binds to the I-domain of a human α2-integrin, said antibody or fragment comprising a heavy chain variable region (VH) domain and a light chain variable region (VL) domain, wherein said antibody or fragment cross-reacts with a non-human primate α2-integrin but does not cross-react with a non-primate α2-integrin.

2. Isolated monoclonal antibody or antigen binding fragment thereof, wherein said antibody or fragment specifically binds to the I-domain of a human α2-integrin, said antibody comprising a heavy chain variable region (VH) domain and a light chain variable region (VL) domain, wherein said antibody or fragment competes with a reference antibody for binding to the epitope of the reference antibody, said reference antibody comprising a light chain encoded by the plasmid as deposited with the DSMZ under accession No. DSM 23944 and a heavy chain encoded by either (i) the plasmid as deposited with the DSMZ under accession DSM 23946 or (ii) the plasmid as deposited with the DSMZ under accession No. DSM 23945.

3. The antibody, or antigen binding portion thereof, of embodiment 1 or 2, wherein said antibody or fragment specifically binds to the I-domain of the human α2-integrin with nM binding affinity.

4. The antibody, or antigen binding portion thereof, of any one of the previous embodiments, wherein said antibody or fragment inhibits the interaction of the human α2-integrin with collagen in vitro, thereby inhibiting the activation of platelets due to adhesion of said platelets to said collagen.

5. The antibody, or antigen binding portion thereof, of any one of the previous embodiments, said heavy chain variable region domain comprising the heavy chain HCDR3 of SEQ ID NO:5.

6. The antibody, or antigen binding portion thereof, of any one of the previous embodiments, said heavy chain variable region domain comprising the heavy chain CDRs of SEQ ID NO:3 (HCDR1), SEQ ID NO:4 (HCDR2), and SEQ ID NO:5 (HCDR3), or functionally active variants thereof.

7. The antibody, or antigen binding portion thereof, of embodiment 6, wherein the functionally active variant of HCDR2 comprises the mutation Asp→Glu at amino acid position 6.

8. The antibody, or antigen binding portion thereof, of any one of the previous embodiments, said light chain variable region domain comprising the light chain LCDR3 of SEQ ID NO:8.

9. The antibody, or antigen binding portion thereof, of any one of the previous embodiments, said light chain variable region domain comprising the light chain CDRs of SEQ ID NO:6 (LCDR1), SEQ ID NO:7 (LCDR2), and SEQ ID NO:8 (LCDR3), or functionally active variants thereof.

10. The antibody, or antigen binding portion thereof, of embodiment 9, wherein the functionally active variant of LCDR1 comprises the mutation Asn→Gln at amino acid position 11.

11. The antibody, or antigen binding portion thereof, of any one of the previous embodiments, said heavy chain variable region (VH) domain having at least 90%, 95%, 97% or 99% sequence identity to the VH sequence of SEQ ID NO: 2.

12. The antibody, or antigen binding portion thereof, of embodiment 11, wherein said heavy chain variable region (VH) domain comprises the sequence of SEQ ID NO:2 or a functionally active thereof.

13. The antibody, or antigen binding portion thereof, of any one of the previous embodiments, said light chain variable region (VL) domain having at least 90%, 95%, 97% or 99% sequence identity to the VL sequence of SEQ ID NO: 1.

14. The antibody, or antigen binding portion thereof, of embodiment 13, wherein said light chain variable region (VL) domain comprises the sequence of SEQ ID NO:1 or a functionally active thereof.

15. The antibody, or antigen binding portion thereof, of any one of the previous embodiments, wherein said heavy chain variable region (VH) domain comprises one or more amino acid substitutions at positions selected from the group consisting of H5, H7, H11, H12, H17, H20, H38, H40, H43, H55, H61, H65, H66, H67, H76, H81, H82, H87, H91, H93, H112, H113 and H116.

16. The antibody, or antigen binding portion thereof, of embodiment 15, wherein the one or more amino acid substitutions are selected from the group consisting 5His→Val, 7Pro→Ser, 11Leu→Val, 12Val→Lys, 17Pro→Ser, 20Leu→Val, 38Lys→Arg, 40Arg→Ala, 43Arg→Gln, 55Asp→Glu, 61Asn→Ala, 65Lys→Gln, 66Asp→Gly, 67Lys→Arg, 76Ser→Thr, 81Ile→Met, 82Gln→Glu, 87Thr→Arg, 91Ser→Thr, 93Val→Lys, 112Thr→Leu, 113Leu→Val and 116Ser→Val.

17. The antibody, or antigen binding portion thereof, of any one of the previous embodiments, wherein said light chain variable region (VL) domain comprises one or more amino acid substitutions at positions selected from the group consisting of L9, L12, L15, L22, L34, L46, L47, L80, L83, L85, L87, and L89.

18. The antibody, or antigen binding portion thereof, of embodiment 17, wherein the one or more amino acid substitutions are selected from the group consisting of 9Ala→Ser, 12Ala→Ser, 15Leu→Val, 15Leu→Pro, 22Ser→Thr, 34Asn→Gln, 46Gln→Lys, 47Ala→Pro, 80Asp→Asn, 83Glu→Gln, 85Asp→Glu, 87Ala→Thr and 89Thr→Asn.

19. The antibody, or antigen binding portion thereof, of any one of the previous embodiments, said heavy chain variable region (VH) domain having at least 90%, 95%, 97% or 99% sequence identity to a VH sequence selected from the group consisting of SEQ ID NO: 38 (HC1), SEQ ID NO:39 (HC2), SEQ ID NO:40 (HC3), SEQ ID NO:41 (HC4), SEQ ID NO:42 (HC5), SEQ ID NO:43 (HC6), and SEQ ID NO:44 (HC7).

20. The antibody, or antigen binding portion thereof, of embodiment 19 said heavy chain variable region (VH) domain comprising a VH sequence selected from the group consisting of SEQ ID NO: 38 (HC1), SEQ ID NO:39 (HC2), SEQ ID NO:40 (HC3), SEQ ID NO:41 (HC4), SEQ ID NO:42 (HC5), SEQ ID NO:43 (HC6), and SEQ ID NO:44 (HC7).

21. The antibody, or antigen binding portion thereof, of any one of the previous embodiments, said light chain variable region (VL) domain having at least 90%, 95%, 97% or 99% sequence identity to a VL sequence selected from the group consisting of SEQ ID NO: 33 (LC1), SEQ ID NO:34 (LC2), SEQ ID NO:35 (LC3), SEQ ID NO:36 (LC4), and SEQ ID NO:37 (LC5).

22. The antibody, or antigen binding portion thereof, of embodiment 21, said light chain variable region (VL) domain comprising a VL sequence selected from the group consisting of SEQ ID NO: 33 (LC1), SEQ ID NO:34 (LC2), SEQ ID NO:35 (LC3), SEQ ID NO:36 (LC4), and SEQ ID NO:37 (LC5).

23. The antibody, or antigen binding portion thereof, of any one of the previous embodiments, wherein said antibody or binding portion is a chimeric antibody or humanized antibody.

24. The antibody, or antigen binding portion thereof, of any one of the previous embodiments, wherein the antigen binding portion is selected from the group consisting of a Fab, a Fab', a F(ab')2, a Fv, a disulfide linked Fv, a scFv, and a (scFv)$_2$.

25. The antibody, or antigen binding portion thereof, of any one of the previous embodiments, which is selected from the group consisting of a multispecific antibody, a dual specific antibody, a isotype antibody, a dual variable domain antibody and a bispecific antibody.

26. The antibody, or antigen binding portion thereof, of any one of the previous embodiments, comprising a heavy chain immunoglobulin constant domain selected from the group consisting of: a human IgM constant domain, a human IgG1 constant domain, a human IgG2 constant domain, a human IgG3 constant domain, domain, a human IgG4 constant domain, a human IgE constant domain, and a human IgA constant domain.

27. The antibody, or antigen binding portion thereof, of any one of the previous embodiments, comprising a human IgG4 constant domain.

28. An isolated nucleic acid encoding the amino acid sequence of the antibody, or antigen binding portion thereof, of any one of the preceding embodiments.

29. A recombinant expression vector comprising the nucleic acid of embodiment 28.

30. A host cell comprising the recombinant expression vector of embodiment 29.

31. A method of producing the antibody or antigen binding fragment of any one of embodiments 1-26, comprising culturing the host cell of embodiment 30 under conditions such that an antibody is produced by the host cell.

32. A pharmaceutical composition comprising the antibody, or antigen binding portion thereof, of any one of embodiments 1-27 and one or more pharmaceutically acceptable carriers.

33. A method of treating, preventing or diagnosing an α2-integrin-related disorder or disease, the method comprising administering to a subject in need of thereof the pharmaceutical composition of embodiment 32.

34. The method of embodiment 33, wherein the α2 integrin-related disease or disorder is selected from the group consisting of thrombosis, a vascular disease, cancer, including neo-angiogenesis and metastasis, inflammation, inflammatory disease, autoimmune disease and a disease characterized by abnormal or increase angiogenesis, inflammatory bowel disease, Crohn's disease, ulcerative colitis, reactions to transplant, optical neuritis, spinal cord trauma, rheumatoid arthritis, systemic lupus erythematosus (SLE), multiple sclerosis, Reynaud's syndrome, experimental autoimmune encephalomyelitis, Sjorgen's syndrome, scleroderma, cardiovascular disease, psoriasis, and infections that induce an inflammatory response.

35. The method of embodiment 33, wherein the α2 integrin-related disease or disorder is selected from the group consisting of acute coronary syndrome, percutaneous coronary intervention, ischemic stroke, carotid artery stenosis or peripheral arterial occlusive disease.

36. A method of diagnosing a disease associated with altered α2 integrin, the method comprising
a) contacting a sample containing an α2 integrin with the antibody or antigen binding fragment of any one of embodiments 1-27;
b) detecting binding of α2 integrin to the antibody or antigen binding fragment; and
c) comparing the binding of step b) with a reference, wherein a altered α2 integrin binding in
the sample relative to the reference is indicative of the disease.

37. An article of manufacture comprising
a) a packaging material,
b) the antibody or antigen binding fragment of any one of embodiments 1-27,
c) a label or a package insert, the insert contained within said packaging material, indicating that said antibody or antigen binding fragment is effective for treatment or diagnosis of an α2 integrin-related disease disorder.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The invention is further illustrated by the following example, although it will be understood that the examples are included merely for purposes of illustration and are not intended to limit the scope of the invention unless otherwise specifically indicated.

FIGURES

FIGS. 1A and B show binding of anti-α2 integrin mAB purified from hybridoma supernatant on HUVEC MesoScale Technology.

FIG. 2 shows the effect of anti-α2 integrin mAb purified from hybridoma supernatant on HUVEC angiogenesis. Anti-α2 integrin mAb was able to inhibit FGF2-induced angiogenesis in a dose-dependent manner.

FIG. 3 shows inhibition of platelet adhesion to collagen under flow by anti-α2 integrin mAB-Fab. Anti-coagulated human blood is incubated for 10 min with DiOC6(3) dye and serial dilutions of anti-α2 integrin Fab at 37° C. Then the blood is flown through collagen-coated capillaries at a shear rate of 3000 s−1. From 10 pictures as representative examples of the covered area the surface coverage is calculated. The values show the percentage of inhibition of said surface coverage as a dose-dependent effect of anti-α2 integrin Fab FIG. 4: Shows interspecies cross reactivity studies performed by FACS analyses using α2 mAb from hybridoma supernatant and blood samples from *macaca* (FIGS. 4*a* and *b*) and human (FIG. 4*c* and *d*), FIGS. 4*a* and 4*c* represent negative controls only using the secondary antibody without use of primary antibody.

FIG. 5: FIG. 5*a*) shows the amino acid sequence (SEQ ID NO:1) and coding sequence (SEQ ID NO:12) of the variable light chain of the anti-α2 integrin monoclonal mouse antibody produced by hybridoma. FIG. 5*b*) shows the amino acid sequence (SEQ ID NO:2) and coding sequence (SEQ ID NO:13) of the variable heavy chain of the anti-α2 integrin monoclonal mouse antibody. In the amino acid sequences, the CDRs are marked bold and underlined.

FIG. 6: Shows the amino acid sequences of the different CDRs of the anti-α2 integrin monoclonal mouse antibody, wherein FIG. 6*a* shows the heavy chain CDRs and FIG. 6*b* shows the light chain CDRs with HCDR1 being SEQ ID NO:3, HCDR2 being SEQ ID NO:4, HCDR3 being SEQ ID NO:5, LCDR1 being SEQ ID NO:6, LCDR2 being SEQ ID NO:7, LCDR3 being SEQ ID NO:8.

FIG. 7 Shows the sequences of the chimeric constructs generated by coupling of the above murine variable light chain region (SEQ ID NO: 1) or variable heavy chain regions (SEQ ID NO: 2) to (parts of) a human constant region as detailed in the Examples. FIG. 7*a* shows the amino acid (SEQ ID NO:9) and coding (SEQ ID NO: 14) sequences of the chimeric light chain, FIG. 7*b* shows the amino acid (SEQ ID NO: 10) and coding (SEQ ID NO: 15) sequences of the chimeric heavy chain, FIG. 7*c* shows the amino acid (SEQ ID NO: 11) and coding (SEQ ID NO: 16) sequences of the chimeric heavy chain Fab fragment. In the amino acid sequences, the CDRs have been underlined, the sequence representing the α2 variable domains have been typed bold and the His tag is written in italics.

FIG. 8 Shows the amino acid sequences of different human constant regions used for generation of the chimeric constructs: SEQ ID NO:17 is the amino acid sequence of human IGKC protein, light chain constant region according to Swiss-Prot accession number Q502W4 as used for the generation of the light chain chimera according to SEQ ID NO:9, SEQ ID NO:18 is the amino acid sequence of human mutated IGHG4, heavy chain constant region according to Swiss-prot accession number P01861.1 as used for construction of the heavy chain chimera according to SEQ ID NO:10 (the mutated amino acids are typed bold), SEQ ID NO:19 is the amino acid sequence of Human IGHG1 protein, heavy chain constant region according to Swiss-Prot accession number Q569F4 as used for the generation of the heavy chain Fab fragment chimera according to SEQ ID NO:11.

FIG. 9 Shows the Amino acid and coding sequences of human α2 and β1 integrin with SEQ ID NO: 20 being the amino acid sequence of α2 integrin precursor protein according to NP_002194.2. The I-Domain, which was used for experiments and recombinantly expressed in *e. coli*, is underlined and bold-typed. SEQ ID NO: 21 is the coding sequence of α2 integrin according to NCBI accession number: NM_002203.3, SEQ ID NO: 22 is the amino acid sequence of β1 integrin isoform 1A precursor protein according to NCBI accession number: NP_002202.2 and SEQ ID NO:23 is the coding sequence of β1 integrin isoform 1A according to NCBI accession number: NM_002211.3.

FIG. 10 shows the amino acid and coding sequences of the original murine anti-α2 integrin antibody from mouse hybridoma and verified by MS: SEQ ID NO: 45 (FIG. 10*a*) is the nucleotide sequence of cDNA encoding the LC of the anti-α2 integrin mAB, SEQ ID NO: 46 (FIG. 10*b*) is the nucleotide sequence of cDNA encoding HC anti-α2 integrin mAB, SEQ ID NO: 47 (FIG. 10*c*) is the amino acid sequence of the LC of anti-α2 integrin mAB as secreted from hybridoma, SEQ ID NO:48 (FIG. 10*d*) is the amino acid sequence of the LC of anti-α2 integrin mAB as secreted from hybridoma. SEQ ID NO: 53 (FIG. 10*e*) is the amino acid sequence of the LC of the comparator mAb TMC2206, SEQ ID NO: 54 (FIG. 10*f*) is the amino acid sequence of the HC of the comparator mAb TMC2206.

Figure 14:
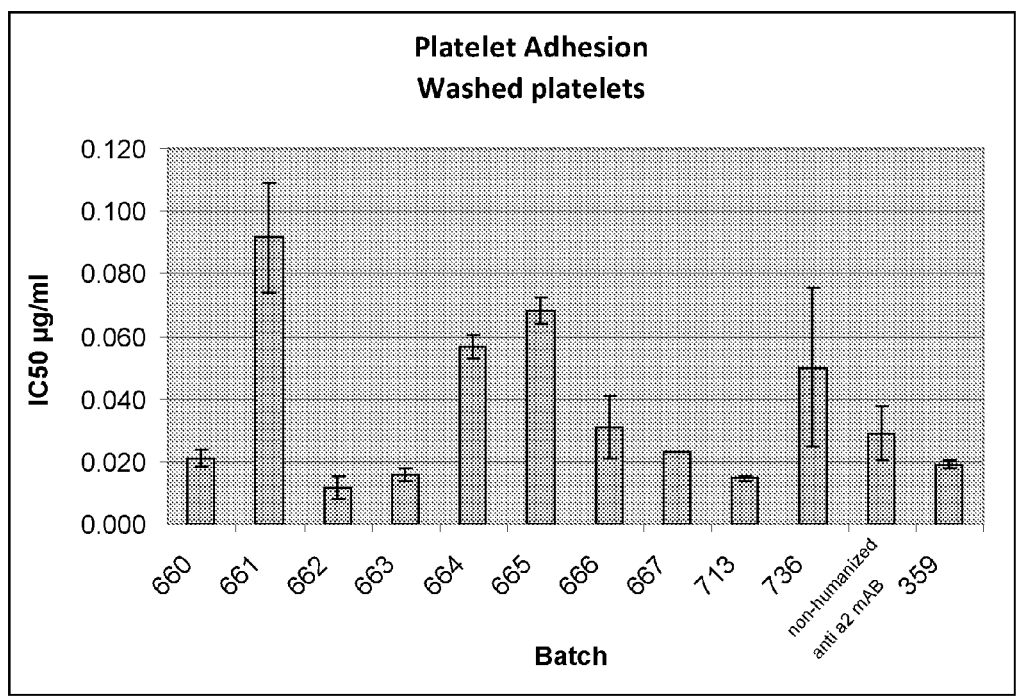

FIG. 14 shows the inhibitor of platelet adhesion to collagen under static conditions using washed platelets. Batch 660 corresponds to LC1/HC1, batch 661 corresponds to LC2/HC2, batch 662 corresponds to LC3/HC3, batch 663 corresponds to LC3/HC4, batch 664 corresponds to LC4/HC5, batch 665 corresponds to LC4/HC6, batch 666 corresponds to LC5/HC7, and batch 667 is the comparator. The results can also be derived from table 12. Batch number 660, 662, and 663 show at least equal or better inhibition of the platelet adhesion to collagen as mAb TMC2206.

EXAMPLES

Example 1

Generation and Selection of Functional Anti-α2 Integrin mAb and Fab

A—Sequence Isolation Out of α2 Integrin mAB Clone Cells Production and Purification of α2 Integrin mAb from Hybridoma One cryovial containing $2\times10^6$ cells of the α2 integrin mAB cell bank was thawed rapidly at 37° C. Cells were transferred into T-25 cm2 flask in 5 mL of fresh media consisting of Dulbecco's Modified Eagle Medium (Gibco 31053-028) supplemented with 10% FBS, 1×ITS (Gibco 41 400-045), 1× sodium pyruvate (Gibco 11 360-039), 150 μg/mL of oxaloacetic acid, 2 mM of glutamine (Gibco 25030-024) and 100 U/ml penicillin/streptomycin (Gibco 15070-063) in a 37° C. incubator under a humidified atmosphere of 5% $CO_2$ in air on an orbital shaker platform rotating at 110 rpm.

Isotyping of purified mAb from hybridoma was performed by using standard commercial isotyping kit from Serotec (Mouse Monoclonal Antibody Isotyping Test Kit; ref MMT1) revealed a mCk, mIgG2a isotype.

Cells were subcultured every 2 to 3 days for cell amplification. For production, cells were inoculated at $1.8\times10^5$ C/mL in Iscove's Modified Dulbecco's medium (Sigma I3390) supplemented with 10% FBS, 1×ITS, 1× sodium pyruvate, 150 μg/mL of oxaloacetic acid, 2 mM of glutamine and 100 U/ml penicillin/streptomycin into six T500 flasks (200 mL) for 10 days.

For purification, the anti-α2 integrin mAb was directly captured from supernatant on Protein G affinity chromatography (Hitrap Protein G, GE Healthcare) and eluted by 0.1 M acetic acid.

After polishing the protein by SEC using a Superdex 200 (GE Healthcare) and ultrafiltration the protein was used in indicated experiments.

Determination of the Sequence of the Heavy and Light Chains of the α2 Integrin mAb The cDNA encoding the variable domains of the monoclonal antibody were obtained as follows: mRNA was extracted from hybridoma cells with the Oligotex kit from Qiagen. The corresponding cDNA was amplified by RT-PCR by the RACE method utilizing the Gene Racer kit (Invitrogen), the transcriptase SuperScript III at 55° C. (Invitrogen) and primers described on Table 1 (RACEMOG2a or CKFOR). The cDNA fragments were amplified by PCR with the polymerase Phusion at 55° C. (Finnzymes) and primers also described in Table 1.

TABLE 1

Primers used for RT-PCR and PCR

| Primer | Sequence 5' to 3' |
| --- | --- |
| 5'-GeneRacer Primer | CGACTGGAGCACGAGGACACTGA (SEQ ID NO: 24) |
| RACEMOG2a: 3'-Primer internal to murine hinge | AGGACAGGGCTTGATTGTGGG (SEQ ID NO: 25) |
| CKFOR: 3'-Primer internal to murin Ck murine | CTCATTCCTGTTGAAGCTCTTGAC (SEQ ID NO: 26) |

The amplified fragments encoding the variable regions of heavy (VH) and light (VL) chains were cloned into pCR4-Topo plasmids from Invitrogen which were amplified in *E. coli*. Cloned cDNA was then sequenced on both strands.

Protein sequences were translated from plasmid coding sequences and the masses of the heavy (HC) and light (LC) chains were calculated (Table 2). The values obtained were in perfect agreement with mass spectrometry data obtained from preparation of mAb purified from culture of the corresponding hybridoma, see Table 2. Nucleic acid and amino acid sequences of HC and LC are reported in the sequence listing as follows: SEQ ID NOs 46 and 48 correspond to the HC of the α2-integrin mAb purified from hybridoma supernatant and SEQ ID NOs. 45 and 47 correspond to the LC of α2-integrin mAb purified from hybridoma supernatant.

TABLE 2

Mass spectrometry analysis of α2-integrin mAb from hybridoma

| | Chain | Mass (Da) by LC/MS | Mass (Da) in silico value |
| --- | --- | --- | --- |
| α2 INTEGRIN mAB | LC | 23899 | 23896 |
| | HC | 50728 (G0F) | 50725 (G0F) |

B—Determination of the Sequences of the CDR of the Anti-α2-Integrin mAbs

The sequences for the CDR regions were deduced from the protein sequence using the KABAT nomenclature.

For the HC, CDR1 corresponds to SEQ ID NO.3, CDR2 corresponds to SEQ ID NO.4, CDR3 corresponds to SEQ ID NO.5.

For the LC, CDR1 corresponds to SEQ ID NO.6, CDR2 corresponds to SEQ ID NO.7, CDR3 corresponds to SEQ ID NO.8.

C—Generation of Chimeric Anti-α2-Integrin mAb Expression Plasmids

The variable heavy and light chain of the anti-α2-integrin mAb was generated by PCR, using the AccuPrimePfx SuperMix (Invitrogen; Cat. No.: 12344-040) and the anti-α2-integrin mAb heavy and light chain cDNA respectively (for cDNA generation see above). In a 25 μl PCR reaction, 5 cycles were run with the primers α2 mAB-VH FOR and REV (heavy chain) or primers α2 mAB-VL FOR and REV (light chain) primers (95° C., 15 sec; 62° C., 30 sec; 68° C., 1 min). To introduce the leader sequence, 0.5 μl of each of the first PCR sample were used as template for a second PCR with Leader FOR1-54 and α2 mAB-VL (or -VH) REV primers using the same PCR conditions as for the first PCR. Finally, 0.5 μl of the second PCR were used as template for a third PCR performing 25 cycles with Leader FOR1-23 and α2 integrin mAB-VL (or -VH) REV primers using the same PCR conditions as for the first reaction. The PCR products of the 3rd PCR were purified using the PCR purification kit (Qiagen, Cat. No. 28104) as described in the kit protocol). PCR products were cloned into the pCR2.1-TOPO using the Invitrogen TOPO TA cloning kit (Cat #450001) as described in the vendor's manual and sequenced using M13 forward and M13 reverse primers included in the cloning kit.

The sequences of the murine α2 antibody variable light and heavy chain can be gained from FIG. 5 with SEQ ID NO:1 referring to the amino acid sequence and SEQ ID NO:12 referring to the coding sequence of the variable light chain domain and with SEQ ID NO:2 referring to the amino acid sequence and SEQ ID NO:13 referring to the coding sequence of the variable heavy chain domain.

The variable light domain (according to SEQ ID NO:1) was fused to the constant light chain (IGKC, Swiss-Prot: Q502W4), by digesting the VL with NheI/BsiWI and IGKC BsiWI/HindIII giving rise to the α2 antibody VL-IGKC light chain chimera according to SEQ ID NOs:9 and 14. This fusion was ligated into the NheI/HindIII sites of the episomal expression vector pXL (Durocher et al. (2002), Nucl. Acids Res. 30(2)), E9, creating the mammalian expression plasmid of the chimeric α2 antibody light chain "pFF0033_pXLc-AscII-IGKC" as deposited with the DSMZ under accession No. DSM 23944.

The variable heavy domain (according to SEQ ID NO:2) was fused to a mutated variant of the human constant heavy chain (IGHG4, Swiss-Prot P01861, S108P, L115E) giving rise to the α2 integrin VH-IGHG4 constant heavy chain chimera according to SEQ IDs NO: 10/15 or in order to create a Fab, fused to a 6× His (SEQ ID NO: 55) tagged CH1 domain from the human constant IGHG1 (Swiss-Prot: Q569F4) giving rise to the α2 integrin VH-IGHG1 constant heavy chain Fab chimera according to SEQ ID NOs:11/16. To this end, the VH was digested NheI/ApaLI and fused to the ApaI/HindIII digested IGHG4 or His tagged CH1 domain respectively. This fusion was ligated into the NheI/HindIII sites of the episomal expression vector pXL, respectively creating for the mammalian expression plasmid of the chimeric α2 antibody heavy chain-IgG4 "pFF0036_pXLc-AscII-IGHG4" as deposited with the DSMZ under accession DSM 23946, or for the mammalian expression plasmid of the chimeric α2 antibody heavy chain-Fab "pFF0035_pXLc-AscII-CH1-Hi" as deposited with the DSMZ under accession No. DSM 23945.

The different plasmids have been deposited with the Deutsche Sammlung von Mikroorganismen und Zellkulturen GmbH (DSMZ), Braunschweig under the following accession numbers: DSM 23945 (plasmid for eucaryotic expression of the chimeric anti α2 antibody heavy chain Fab fragment), DSM 23946 (plasmid for the expression of the chimeric anti α2 antibody IgG4 heavy chain) and DSM 23944 (plasmid for the expression of the chimeric anti α2 antibody IGKC light chain).

Sequences of the Above Used Primers

|  | SEQ ID NO: |
|---|---|
| α2mAB-VL FOR:<br>CTGGTGGCCACCGCCACCGGCGTGCACAGCAACATTGTGCTGACCCAATCTC | 27 |
| α2mAB-VL REV:<br>ACCGTACGTTTTATTTCCAGCTTGGTCCCC | 28 |
| α2mAB mAB-VH FOR:<br>CTGGTGGCCACCGCCACCGGCGTGCACAGCCAGGTCCAACTGCATCAGCCTG | 29 |
| α2mAB mAB-VH REV:<br>TAGGGCCCTTGGTGCTGGCTGAGGAGACTGTGAGAGTGG | 30 |
| Leader for 1-54:<br>GCTAGCACCATGGGCTGGTCCTGCATCATCCTGTTTCTGGTGGCCACCGCCACC | 31 |
| Leader for 1-23:<br>CAAGCTAGCACCATGGGCTGGTCCTG | 32 |

Example 2

Properties of Anti α2-Integrin mAb and Fab

A—Production of Recombinant Anti α2 Integrin mAB and Fab Fragments

Expression of Chimeric Anti α2integrin-IgG4 and Anti α2-Integrin—Fab Molecules

The expression plasmids encoding the heavy and light chain of the antibody were propagated in *E. coli* DH5a. Plasmids used for transfection were prepared from *E. coli* using the Qiagen EndoFree Plasmid Mega Kit.

HEK 293-FS cells growing in Freestyle Medium (Invitrogen) were transfected with indicated LC and HC plasmids using Fugene (Roche) transfection reagent. After 7 days the cells were removed by centrifugation and the supernatant and passed over a 0.22 µm filter to remove particles.

Purification of Chimeric Anti α2-Integrin-IgG4 and Anti α2-Integrin—Fab Molecules IgG4 Protein was purified by affinity chromatography on Protein A (HiTrap Protein A HP Columns, GE Life Sciences). After elution from the column with 100 mM acetate buffer with 100 mM NaCl pH 3.5, the monoclonal antibodies were desalted using HiPrep 26/10 Desalting Columns, formulated in PBS at a concentration of 1 mg/mL and 0.22 µm filtered.

Fab proteins were purified by IMAC on HiTrap IMAC HP Columns (GE Life Sciences). After elution from the column with a linear gradient (Elution buffer: 20 mM sodium phosphate, 0.5 M NaCl, 50-500 mM imidazole, pH 7.4), the protein containing fractions were pooled and desalted using HiPrep 26/10 Desalting Columns, formulated in PBS at a concentration of 1 mg/mL and 0.22 µm filtered.

Protein concentration was determined by measurement of absorbance at 280 nm. Each batch was analyzed using a Protein 200 Plus LabChip kit on the Agilent 2100 bioanalyzer under reducing and non-reducing conditions to determine the purity and the molecular weight of each subunit and of the monomer.

B—Binding Properties of the Anti-α2 Integrin mAb or Fab

Surface plasmon resonance technology on a Biacore 3000 (GE Healthcare) was used for detailed kinetic characterisation of the purified antibody and the corresponding Fab fragment. A direct binding assay was used with the anti-integrin antibody or the Fab fragment as the ligand and the integrin α2β1 I-domain as analyte. Typically, 600 RU of antibody or Fab fragment were immobilised on a research grade CM5 chip by amine reactive coupling, resulting in an Rmax of 80 and 140 RU for the I domain bound to the antibody and the Fab fragment, respectively. Binding kinetics were measured over a concentration range between 0.4 to 28 nM I-domain in HBS-P buffer supplemented with 4 mM MgCl2 (10 mM HEPES pH 7.4, 150 mM NaCl, 0.005% Surfactant P20) at a flow rate of 30 μl/min. Chip surfaces were regenerated with 10 mM glycine pH 2.2. Kinetic parameters were analysed and calculated in the BIAevaluation program package (version 4.1) using a flow cell without immobilised anti-integrin antibody or Fab fragment as reference. A 1:1 binding model with mass transfer was applied for a global fit of the data for curves corresponding to analyte concentrations from 0.4-28 nM of antibody or Fab fragment.

TABLE 3

The binding kinetics of anti-α2-integrin mAb and Fab fragment against the integrin I-domain.

| Ligand | ka (1/Ms) E+05 | kd (1/s) E−04 | KD (M) E−10 |
|---|---|---|---|
| Antibody | 8.6 | 11.7 | 13.5 |
| Fab frament | 9.9 | 8.3 | 8.4 |

The blocking mAb and Fab displayed affinities in the nanomolar range to human α2β1-domain (Table 3).

Figure 1A:
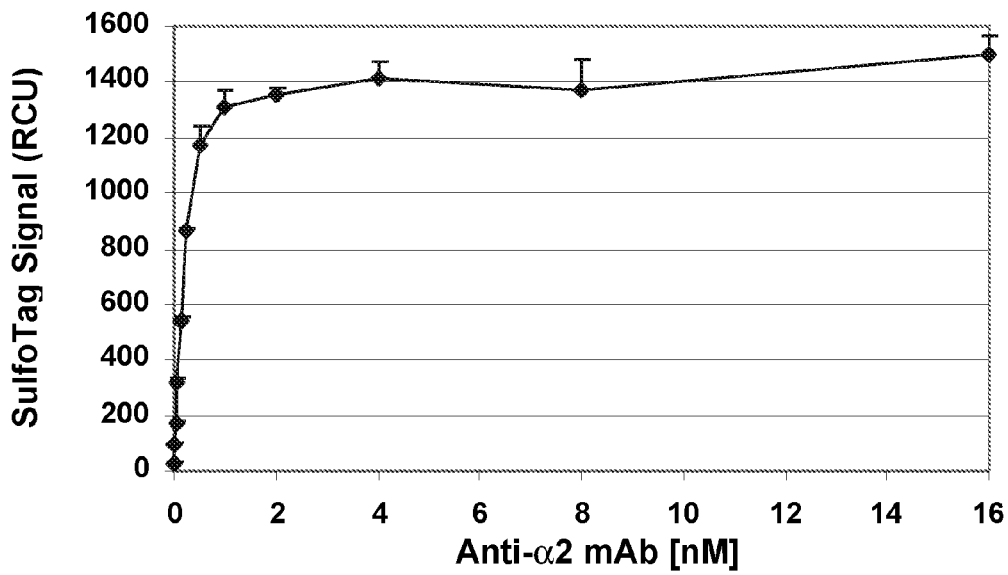
Figure 1B:
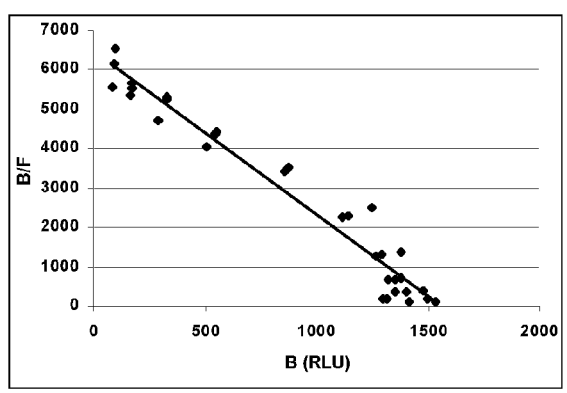

To further assess the binding properties of the anti-α2 integrin mAb, a cell based assay with HUVEC cells (promocell C12200, lot 6062203) was performed. Cells were coated onto high binding plates (Meso Scale Discovery (MSD), L15XB-3) in PBS (10.000 cells/well) and incubated for 2 hrs at room temperature. Then the plates were emptied, washed twice with PBS and blocked with blocking solution (MSD, R93BA-4) for 90 min. After emptying and washing the plates again as described above, serial dilutions of anti α2-mAb were added and incubated with the cells for 1 h at room temperature. Following another washing step as above Read buffer T without surfactant (Meso scale Discovery, R92TD-2) was added. Electrochemilumenescence was read in a suitable device (Meso scale Discovery, Sector imager). Scatchard plot analysis was used to determine KD of the tested mAbs (see FIG. 1).

C—Cross-Reactivity Properties of the Anti-α2-Integrin mAb

The anti α2 integrin mAb was assessed for its ability to specifically interact with platelets from *macaca* and man by means of FACS experiments using blood samples or human platelets. The mAb was incubated with samples of human blood, *macaca* blood or human platelets and with goat-anti-mouse-IGg Phycoerithrin (PE) coupled secondary mAbs (Beckman Coulter #731856). The samples were treated with Lysing Solution (BD #349202) and the platelets spun down, resuspended and analysed by FACS.

The anti α2 integrin mAb showed similar reactivity with blood samples of *macaca fascicularis* (97.3% positives, FIG. 4b) as with human whole blood sample (>98% positives, FIG. 4d), whereas no reactivity has been detected against mouse, rat, dog, guinea pig, pig or rabbit α2β1 integrin as tested with whole blood from those species (data not shown). Thus, according to the FACS analyses, there appears to be interspecies crossreactivity of the antibody with primate α2β1 integrin on platelets from *macaca* blood, whereas no cross-reactivity has been detected against mouse, rat, dog, guinea pig, pig or rabbit α2β1 integrin as tested with whole blood from those species.

Example 3

Humanization and Engineering of the Fv Domain of Anti-α2 IgG and Fab

Humanization

The 3D homology models of the VL and VH sequences of the anti-α2 integrin mAB antibody were built using the antibody modeler application in MOE 2008. Several PDB templates were identified to build the LC and HC frameworks and CDR loops. All templates had an identity above 83% vs. the VL and VH anti-α2 integrin mAB sequences, except the best template vs. the H3 loop (56% identity). The resulting LC and HC models were subsequently energy minimized using the standard procedure implemented in MOE. A molecular dynamic (MD) calculation of the minimized 3D homology model of the murine VL/VH was subsequently performed, with constraints on the protein backbone and at 500K temperature, for 1.1 nanoseconds in Generalized Born implicit solvent. 10 diverse conformations were extracted from this first MD run every 100 ps for the last 1 ns. These 10 diverse conformations were then each submitted to a MD, with no constraints on the protein backbone and at 300K temperature, for 2.3 nanoseconds in Generalized Born implicit solvent. For each of the 10 MD runs, the last 2,000 snapshots, one every picoseconds, from the MD trajectory were then used to calculate, for each anti-α2 integrin mAB amino-acid, its root mean square deviations (rmsd) compared to a reference medoïd position. By comparing the average rmsd on the 10 separate MD runs of a given amino-acid to the overall average rmsd of all anti-α2 integrin mAB murine amino-acids, one decides if the amino-acid is flexible enough, as seen during the MD, to be considered as likely to interact with T-cell receptors and responsible for activation of the immune response. 64 amino-acids are finally identified as flexible in the anti-α2 integrin mAB antibody, of which 34 are not located in the CDRs or their immediate vicinity (5 Å). Amino-acids located in the "Vernier" zone are also not considered (J. Mol. Biol. 1992, 224, 487-499).

The motion of the most 34 flexible anti-α2 integrin mAB amino-acids (excluding the CDR+5 Å region), during the 20 ns (10×2 ns), were then compared to the motion of the corresponding flexible amino-acids of 49 human germlines homology models, for each of which were run the 10×2 ns MD simulations. The 49 human germlines models were built by systematically combining the 7 most common human germline light chains (vk1, vk2, vk3, vk4, vlambda1, vlambda2, vlambda3) and 7 most common human germline heavy chains (vh1a, vh1b, vh2, vh3, vh4, vh5, vh6). The vk1-vh1b human germline antibody showed a 62% 4D similarity of its flexible amino-acids compared to the flexible amino-acids of the anti-α2 integrin mAB; the vk1-vh1b germline antibody was therefore used to humanize the anti-α2 integrin mAB antibody focusing on the flexible amino-acids. For the pairwise amino-acid association between anti-α2 integrin mAB and vk1-vh1b amino-acids, the 2 sequences were aligned based on the optimal 3D superposition of the α carbons of the 2 corresponding homology models.

Stabilisation

The amino-acids of the light and heavy chains with low frequency of occurrence vs. their respective canonical sequences, excluding the CDRs, are originally proposed to be mutated into the most frequently found amino-acids (ΔΔGth>0.5 kcal/mol; [E. Monsellier, H. Bedouelle.

Improving the stability of an antibody variable fragment by a combination of knowledge-based approaches: validation and mechanisms. J. Mol. Biol. 2006, 362, 580-593]). A first list of consensus mutations for the LC and for the HC has been restricted to the amino-acids found in the closest human germline (i.e. vk1-vh1b), i.e. to 4 potential mutations in the LC and 3 in the HC. None of these mutations are located in the CDRs, its immediate vicinity (+5 Angstroms) or in the "Vernier" zone (J. Mol. Biol. 1992, 224, 487-499). Other criteria are taken into account to consider these consensus mutations for potentially stabilizing the anti-alpha2 integrin antibody. These criteria are a favourable change of hydropathy at the surface or a molecular mechanics based predicted stabilisation of the mutant.

Humanization by Grafting

The humanization starts by identifying the closest human germlines to, respectively, the anti-α2 integrin mAB light and heavy chains. This is done by performing a BLAST search vs. all the human germlines which were systematically enumerated (all possible combinations of the V and J domains for the kappa and lambda chains; V, D and J domains for the heavy chains). The BLAST searches were performed using an in-house intranet application.

The following closest human germlines were identified with respectively 77% and 68% identity to the anti-α2 integrin light (SEQ ID NO: 1) and heavy chains (SEQ ID NO: 2):

```
α2_lc               NIVLTQSPAS LAVSLGQRAT ISCRASESVE SYGNSFIYWY QQKPGQAPKL LIYLASNLAS
IGLKV79_IGLKJ2      DIVLTQSPAS LAVSPGQRAT ITCRASESVS FLGINLIHWY QQKPGQPPKL LIYQASNKDT

α2_lc               GVPARFSGSG SRTDFTLTID PVEADDAATY YCQQNNEDPY TFGGGTKLEI K
IGLKV79_IGLKJ2      GVPARFSGSG SGTDFTLTIN PVEANDTANY YCLQSKNFPY TFGQGTKLEI K

α2_hc               QVQLHQPGAE LVKPGAPVKL SCKASGYTFT SYWMNWVKQR PGRGLEWIGR IDPSDSETHY
IGHV11_IGHD33_IGHJ8 QVQLVQSGAE VKKPGASVKV SCKASGYTFT SYYMHWVRQA PGQGLEWMGI INPSGGSTSY

α2_hc               NQKFKDKATL TVDKSSSTAY IQLSSLTSED SAVYYCAKVG RGYFDYWGQG TTLTVSS
IGHV11_IGHD33_IGHJ8 AQKFQGRVTM TRDTSTSTVY MELSSLRSED TAVYYCARL- TGYFDYWGQG TLVTVSS
```

IGLKV79_IGLKJ2 corresponds to SEQ ID NO: 49. IGHV11_IGHD33_IGHJ8 corresponds to SEQ ID NO. 50.

The humanizing mutations are obtained by performing a pairwise comparison of the 2 aligned sequences, excluding the CDR (Kabat numbering) and Vernier zone residues.

Mutation of Unwanted Sequence Motifs

The following motifs of sequences were considered: Asp-Pro (acide labile bond), Asn-X-Ser/Thr (glycosylation, X=any amino-acid but Pro), Asp-Gly/Ser/Thr (succinimide/iso-asp formation in flexible areas), Asn-Gly/His/Ser/Ala/Cys (exposed deamidation sites), Met (oxidation in exposed area). The resulting humanised sequences were blasted for sequence similarity against the IEDB database (http://www.immuneepitope.org/home.do; version June 2009) to ensure that none of the sequences contain any known B- or T-cell epitope.

1. Original Sequences of the Anti-a2b1 Integrin Variable Domains a. Light Chain (CDRs + 5Å are in bold, 1 NS potential problematic motif in the CDRs region underlined)

NIVLTQSPAS LAVSLGQRAT ISCRASESVE SYGNSFIYWY QQKPGQAPKL
LIYLASNLAS GVPARFSGSG SRTDFTLTID PVEADDAATY YCQQNNEDPY
TFGGGTKLEI K (SEQ ID NO: 1)

b. Heavy Chain (CDRs + 5Å are in bold, 1 problematic site in the CDRs region [DS succinimide and iso-Asp formation site] underlined)

QVQLHQPGAE LVKPGAPVKL SCKASGYTFT SYWMNWVKQR PGRGLEWIGR
IDPSDSETHY NQKFKDKATL TVDKSSSTAY IQLSSLTSED SAVYYCAKVG
RGYFDYWGQG TTLTVSS (SEQ ID NO: 2)

Engineered Sequences Five versions for the light chain (light chain variants LC1, LC2, LC3, LC4, LC5) and seven versions for the heavy chain were designed (heavy chain variants HC1, HC2, HC3, HC4, HC5, H6, H7). The LC1 version displays 4 mutations which derive from the direct comparison between the non-CDR most flexible amino-acids of the anti-α2 integrin mAB light chain and the VK1 human germline light chain. The LC2 version includes one additional mutation to remove a potentially deamidation site in the CDRs region (N34Q). The LC3 version includes humanizing and stabilizing mutations predicted to optimally stabilize the anti-α2 integrin mAB light chain. The LC4 version includes one additional mutation to remove the potentially (N34Q) deamidation site. The LC5 version displays 6 mutations which derive from the grafting method.

The HC1 version displays 3 mutations, which derive from the direct comparison between the non-CDR most flexible amino-acids of the anti-α2 integrin mAB heavy chain and the VH1b human germline. The HC2 version includes another additional mutation to remove a potentially problematic succinimide Iso-Asp formation site in the CDRs region (D55E). The HC3 version includes humanizing and stabilizing mutations predicted to optimally stabilize the anti-α2 integrin mAB heavy chain. The HC4 version includes an additional mutation to address a potential aggregation issue. The HC5 version includes HC3 mutations and an additional mutation to remove a potentially problematic succinimide Iso-Asp formation site in the CDRs region (D55E). The HC6 version includes an additional mutation to address the potential aggregation issue. The HC7 version displays 20 mutations which derive from the grafting method.

In total seven combinations have been prepared:
- LC1/HC1 (mutations addressing humanization only)
- LC2/HC2 (mutations addressing humanization and LC/HC potentially problematic site [N and DS])
- LC3/HC3 (mutations addressing humanization and stabilization)
- LC3/HC4 (mutations addressing humanization and stabilization and anti-aggregation)
- LC4/HC5 (mutations addressing humanization and stabilisation and LC potentially problematic site [NS] and HC potentially problematic site [DS])
- LC4/HC6 (mutations addressing humanization, stabilisation, anti-aggregation and LC potentially problematic site [NS] and HC potentially problematic site [DS])
- LC5/HC7 (mutations addressing humanization by grafting)

TABLE 4 summary of the 7 LC × HC combinations

|  | (LC1) Humanization | LC2 humanization and NS site in CDRs | LC3 humanization and stabilization | LC4 humanization and NS site in CDRs and stabilization | LC5 (grafting) |
|---|---|---|---|---|---|
| (HC1) Humanization | x | | | | |
| (HC2) Humanization and DS in CDRs | | x | | | |
| (HC3) Humanization and stabilization | | | x | | |
| (HC4) Humanization and stabilization and "anti-aggregation" | | | x | | |
| (HC5) Humanization and DS in CDRs and stabilization | | | | x | |
| (HC6) Humanization and stabilization and "anti-aggregation" and DS in CDRs | | | | x | |
| HC7 (grafting) | | | | | x |

TABLE 5

Summary of the mutations introduced for the engineered light chain of the anti-α2β1 Fab

| Light Chain (Sequential numbering) | (LC1) Humanization | (LC2) humanization and NS in CDRs | (LC3) humanization and stabilization | (LC4) humanization and NS in CDRs and stabilization | (LC5) grafting |
|---|---|---|---|---|---|
| ALA9 | SER | SER | SER | SER | |
| ALA12 | | | SER | SER | |
| LEU15 | VAL | VAL | VAL | VAL | PRO |
| SER22 | | | | | THR |
| ASN34 | | GLN | | GLN | |

TABLE 5-continued

Summary of the mutations introduced for the engineered light chain of the anti-α2β1 Fab

| Light Chain (Sequential numbering) | (LC1) Humanization | (LC2) humanization and NS in CDRs | (LC3) humanization and stabilization | (LC4) humanization and NS in CDRs and stabilization | (LC5) grafting |
|---|---|---|---|---|---|
| GLN46 | LYS | LYS | | | |
| ALA47 | | | | | PRO |
| ASP80 | | | | | ASN |
| GLU83 | GLN | GLN | GLN | GLN | |
| ASP85 | | | GLU | GLU | |
| ALA87 | | | | | THR |
| THR89 | | | | | ASN |

TABLE 6

Mutations of the 7 HC variants of the anti- α 2 integrin antibody

| Heavy Chain (Sequential numbering) | (HC1) Humanization | (HC2) Humanization and DS in CDRs | (HC3) Humanization and stabilization | (HC4) Humanization and stabilization and "anti-aggregation" | (HC5) Humanization and DS in CDRs and stabilization | (HC6) Humanization and stabilization and "anti-aggregation" and DS in CDRs | (HC7) grafting |
|---|---|---|---|---|---|---|---|
| HIS5 | | | | | | | VAL |
| PRO7 | | | | | | | SER |
| LEU11 | | | | | | | VAL |
| VAL12 | | | | | | | LYS |
| PRO17 | | | SER | SER | SER | SER | SER |
| LEU20 | | | | | | | VAL |
| LYS38 | | | | | | | ARG |
| ARG40 | | | | | | | ALA |
| ARG43 | GLN | GLN | | | | | GLN |
| ASP55 | | GLU | | | GLU | GLU | |
| ASN61 | | | | | | | ALA |
| LYS65 | | | | | | | GLN |
| ASP66 | | | | | | | GLY |
| LYS67 | ARG | ARG | | | | | ARG |
| SER76 | | | | | | | THR |
| ILE81 | | | | | | | MET |
| GLN82 | | | | | | | GLU |
| THR87 | | | | | | | ARG |
| SER91 | | | | | | | THR |
| VAL93 | | | | LYS | | LYS | |
| THR112 | | | | | | | LEU |
| LEU113 | | | | | | | VAL |
| SER116 | VAL | VAL | VAL | VAL | VAL | VAL | |
| | 3 mutations | 4 mutations | 2 mutations | 3 mutations | 3 mutations | 4 mutations | 20 mutations |

Humanized variable sequences were generated by gene synthesis and cloned into the corresponding heavy and light chain expression vectors as described in example 1C.

Engineered Light Chain Sequences

Five versions light chain variants were cloned (LC1, LC2, LC3, LC4, LC5). Mutations introduced through the engineering of the variable chains are highlighted or underlined.

```
LC1 (humanizing mutations bold underlined):
                                                       (SEQ ID NO: 33)
NIVLTQSPSS LAVSVGQRAT ISCRASESVE SYGNSFIYWY QQKPGKAPKL

LIYLASNLAS GVPARFSGSG SRTDFTLTID PVQADDAATY YCQQNNEDPY

TFGGGTKLEI K

LC2 (humanizing mutations are highlighted, mutation for CDR NS site
typed bold underlined):

(SEQ ID NO: 34)
NIVLTQSPSS LAVSVGQRAT ISCRASESVE SYGQSFIYWY QQKPGKAPKL LIYLASNLAS

GVPARFSGSG SRTDFTLTID PVQADDAATY YCQQNNEDPY TFGGGTKLEI K

LC3 (humanizing and stabilizing mutations highlighted):

(SEQ ID NO: 35)
NIVLTQSPSS LSVSVGQRAT ISCRASESVE SYGNSFIYWY QQKPGQAPKL LIYLASNLAS

GVPARFSGSG SRTDFTLTID PVQAEDAATY YCQQNNEDPY TFGGGTKLEI K

LC4 (humanizing and stabilizing mutations are highlighted,
mutation for CDR NS site bold underlined):
                                                       (SEQ ID NO: 36)
NIVLTQSPSS LSVSVGQRAT ISCRASESVE SYGQSFIYWY QQKPGQAPKL LIYLASNLAS

GVPARFSGSG SRTDFTLTID PVQAEDAATY YCQQNNEDPY TFGGGTKLEI K

LC5 (grafted mutations are highlighted):
                                                       (SEQ ID NO: 37)
NIVLTQSPAS LAVSPGQRAT ITCRASESVE SYGNSFIYWY QQKPGKPPKL LIYLASNLAS

GVPARFSGSG SRTDFTLTIN PVEADDTANY YCQQNNEDPY TFGGGTKLEI K
```

Below is the alignment of the LC anti-α2β1 integrin vs. the VK1-Vh1b human germline:

```
LC_anti_a2b1  NIVLTQSPAS LAVSLGQRAT ISCRASESVE SYGNSFIYWY QQKPGQAPKL

Vk1LC         DIQMTQSPSS LSASVGDRVT ITCRASQSIS SYLN----WY QQKPGKAPKL

LC_anti_a2b1  LIYLASNLAS GVPARFSGSG SRTDFTLTID PVEADDAATY YCQQNNEDPY

Vk1LC         LIYAASSLQS GVPSRFSGSG SGTDFTLTIS SLQPEDLATY YCQQSYSTPP

LC_anti_a2b1  TFGGGTKLEI K- (SEQ ID NO: 1)

Vk1LC         TFGQGTKVEI KR (SEQ ID NO: 51)
```

Engineered Heavy Chain Sequences

Seven versions of heavy chain variants (HC1, HC2, HC3, HC4, HC5, HC6, HC7) were cloned. Mutations introduced through the engineering of the variable chains are highlighted.

HC1 (humanizing mutations highlighted):

(SEQ ID NO: 38)
QVQLHQPGAE LVKPGAPVKL SCKASGYTFT SYWMNWVKQR

PGQGLEWIGR IDPSDSETHY NQKFKDRATL TVDKSSSTAY

IQLSSLTSED SAVYYCAKVG RGYFDYWGQG TTLTVWS

HC2 (humanizing mutations are highlighted, potentiallly problematic motifs [CDR DS site]):
(SEQ ID NO: 39)
QVQLHQPGAE LVKPGAPVKL SCKASGYTFT SYWMNWVKQR

PGQGLEWIGR IDPSESETHY NQKFKDRATL TVDKSSSTAY

IQLSSLTSED SAVYYCAKVG RGYFDYWGQG TTLTVWS

-continued

HC6 (humanizing and stabilizing mutations are highlighted, potential problematic motifs [CDR DS site, anti-aggregation mutation):
(SEQ ID NO: 43)
QVQLHQPGAE LVKPGASVKL SCKASGYTFT SYWMNWVKQR

PGRGLEWIGR IDPSESETHY NQKFKDKATL TVDKSSSTAY

IQLSSLTSED SAKYYCAKVG RGYFDYWGQG TTLTVWS

HC7 (grafted mutations are highlighted):

(SEQ ID NO: 44)
QVQLVQSGAE VKKPGASVKV SCKASGYTFT SYWMNWVRQA

PGQGLEWIGR IDPSDSETHY AQKFQGRATL TVDKSTSTAY

MELSSLRSED TAVYYCAKVG RGYFDYWGQG TLVTVSS

Below is the alignment of the HC anti-α21 integrin mAb vs. the HC Vk1_Vh1b human germline:

HC2_anti_α2   QVQLHQPGAE LVKPGAPVKL SCKASGYTFT SYWMNWVKQR PGRGLEWIGR

Vh1b          QVQLVQSGAE VKKPGASVKV SCKASGYTFT SYYMHWVRQA PGQGLEWMGW

HC2_anti_α2   IDPSDSETHY NQKFKDKATL TVDKSSSTAY IQLSSLTSED SAVYYCAKVG

Vh1b          INPNSGGTNY AQKFQGRVTM TRDKSSSTAY MELSSLRSED TAVYYCARWG

HC2_anti_α2   RGY------F DYWGQGTTLT VSS (SEQ ID NO: 2)

Vh1b          YDYDVFYYAM DYWGQGTLVT VSS (SEQ ID NO: 52)

-continued
HC3 (humanizing and stabilizing mutations highlighted):
(SEQ ID NO: 40)
QVQLHQPGAE LVKPGASVKL SCKASGYTFT SYWMNWVKQR

PGRGLEWIGR IDPSESETHY NQKFKDKATL TVDKSSSTAY

IQLSSLTSED SAVYYCAKVG RGYFDYWGQG TTLTVWS

HC4 (humanizing and stabilizing mutations are highlighted, anti-aggregation mutation):
(SEQ ID NO: 41)
QVQLHQPGAE LVKPGASVKL SCKASGYTFT SYWMNWVKQR

PGRGLEWIGR IDPSDSETHY NQKFKDKATL TVDKSSSTAY

IQLSSLTSED SAKYYCAKVG RGYFDYWGQG TTLTVWS

HC5 (humanizing and stabilizing mutations are highlighted, potential problematic motifs [CDR DS site]):
(SEQ ID NO: 42)
QVQLHQPGAE LVKPGASVKL SCKASGYTFT SYWMNWVKQR

PGRGLEWIGR IDPSESETHY NQKFKDKATL TVDKSSSTAY

IQLSSLTSED SAVYYCAKVG RGYFDYWGQG TTLTVWS

The variable heavy and light chains of each anti-integrin $\alpha_2$ mAb variant (5 different light chains: VL1-VL5 and 7 different heavy chains: VH1-VH7) were generated by gene synthesis including a 5'UTR-Sequence (5'-GTGCACAGC-3' (SEQ ID NO: 61)) with ApaLI and a 3'UTR (5'-GCTTCCAC-CAAGGGCCC-3' (SEQ ID NO: 62)) with ApaI (heavy chain) or BsiWI (light chain). The variable heavy domains were ligated into the ApaLI/ApaI sites of a modified pXL expression vector which contains a mutated variant of the human constant heavy chain (IGHG4, Swiss-Prot P01861, S108P, L115E) giving rise to an anti-integrin $\alpha_2$ VH-IGHG4 constant heavy chain mAb.

The variable light domains were ligated into the ApaLI/BsiWI sites of a modified pXL expression vector which contains the human constant light chain (IGKC, Swiss-Prot: Q502W4) giving rise to an anti-integrin $\alpha_2$ VL-IGKC constant light chain mAb. The complete process of gene synthesis, cloning and DNA production was realized by a commercial vendor (Geneart AG).

For comparison, a humanized hIgG4 anti-alpha 2 integrin antibody known in the art (TMC2206) was used ("the comparator"). The comparator light- and heavy chain amino acid sequences are listed herein as SEQ IDs NO: 53 and 54 in FIG. 10e.

TABLE 7

List of humanization variants of anti-α$_2$-integrin mAb

| LC/HC combination | Humanization variant |
|---|---|
| LC1/HC1 | Mutations adressing humanization only |
| LC2/HC2 | Mutations adressing humanization only and LC/HC potentially problematic sites (NS; DS) |
| LC3/HC3 | Mutations adressing humanization and stabilization |
| LC3/HC4 | Mutations adressing humanization and stabilization and anti-aggregation |
| LC4/HC5 | Mutations adressing humanization and stabilization and LC/HC potentially problematic sites (NS; DS) |
| LC4/HC6 | Mutations adressing humanization and stabilization and anti-aggregation and LC/HC potentially problematic sites (NS; DS) |
| LC5/HC7 | Mutations adressing humanization by grafting |
| TMC2206 | Comparator according to SEQ ID NO: 53 |

In order to verify the sequences, the mAbs were analyzed using mass spectrometry. For intact mass measurements the sample was trapped for 20 minutes and desalted with 20 μl/min on a monolithic trap column with 2% Acetonitrile/0.1% TFA (v/v) prior to elution with a gradient ranging from 15% Eluent A (H2O/0.05% TFA) to 50% Eluent B (Acetonitrile/0.05% TFA).

The sample was separated operating in nanoflow (300 nl/min) on an monolithic column (PS-DVB; 100 μm I.D.×5 cm) with a temperature of 37° C. Introduction of the sample was carried out using electrospray needles from new objective with an outer diameter of 365 μm, inner diameter of 75 μm and an end tip diameter of 15 μm plus sheath gas. After acquisition the spectra were summed over the corresponding time range and deconvoluted using the protein reconstruction tool delivered with BioAnalyst from Applied Biosystems/MDS Sciex.

Protein sequences were translated from plasmid coding sequences and the masses of the HC and LC were calculated (Table 8).

TABLE 8

Mass spectrometric analysis of the purified humanized anti-α$_2$-integrin mAbs.

| LC/HC combination | Light chain | | | Heavy chain | | |
|---|---|---|---|---|---|---|
| | Expected Da | Measured Da | ppm | Expected Da (G0F) | Measured Da | ppm |
| LC1/HC1 | 23727.38 | 23724.56 | 119 | 50314.47 | 50311.80 | 53 |
| LC2/HC2 | 23741.41 | 23738.26 | 130 | 50328.5 | 50327.52 | 19 |
| LC3/HC3 | 23757.36 | 23753.89 | 146 | 50304.47 | 50301.96 | 50 |
| LC3/HC4 | 23757.36 | 23754.17 | 134 | 50333.52 | 50331.29 | 44 |
| LC4/HC5 | 23771.39 | 23769.87 | 64 | 50318.5 | 50317.68 | 16 |
| LC4/HC6 | 23771.39 | 23768.13 | 137 | 50347.54 | 50350.26 | 54 |
| LC5/HC7 | 23792.41 | 23789.01 | 142 | 50187.3 | 50184.84 | 49 |
| TMC2206 | 23378.01 | 23374.51 | 150 | 50237.54 | 50233.48 | 81 |

The observed values were in good agreement with the calculated masses and verify the cloned constructs.

Example 4

Evaluation of α2 Integrin mAB in Biochemical and Cell-Based Assays In Vitro

For the Solid Phase Assay, integrin (α$_2$-I-domain: α$_2$-I-domain GST aa 140-339 in TBS/5 mM Mn$^{2+}$, 50 μl/well) was immobilized on 96-well plate (Corning Costar, 3690), at room temperature overnight. Then, 25 μl/well of blocking solution (5% BSA (crude) (A7906), 1×TBS) were added and discarded. 200 μl/well of blocking solution were added and left for 3 h at room temperature. After a washing step (3 times with 200 μl/well binding buffer: 1×TBS and 0.1% BSA (A7638) and 2 mM Mn$^{2+}$; TBS: 150 mM NaCl, 25 mM Tris (Fluka 93371) pH7.4), samples were incubated at RT for 3 h stationary with 50 μl of:

a) biotinylated collagen only—control (10 μl binding buffer and 40 μl biot. collagen)
b) 10 μl/well compound, 40 μl/well biotinylated collagen
c) Blank: 50 μl/well binding buffer After a washing step (3 times with 200 μl/well binding buffer), samples were incubated with 50 μl/well ExtrAvidin Peroxidase (Peroxidase conjugate, Sigma E2886; 1:500 in binding buffer) for 30 min at RT and again washed 4 times with 200 μl/well binding buffer. After addition of 50 μl/well peroxidase substrate (ABTS solution; 2,2'-Azino-bis 3-Ethylbenzthiazoline-6-sulfonic acid), Sigma A-1888; 275 μl (11 mg ABTS dissolved in 0.5 ml dH$_2$O; and 5.5 ml 0.1M Sodium-acetate (Sigma S-3272)/0.05M NaH$_2$PO$_4$ (Riedel de Haen 04270) pH5.0; and 55 μl H$_2$O$_2$ Sigma H-1009 (10 μl (=30%) and 1045 μl dH$_2$O) for 10-30 min at RT, stationary (until green staining is obtained) and addition of 50 μl/well 2% SDS, absorbance was read out at 405 nm (SpectraMax 190). % Inhibition is calculated as 100−((mean value compounds*100)/mean value collagen positive control) after blank subtraction.

TABLE 9

Inhibition of collagen interaction by α 2 integrin mAB

| Assay | a2β1-collagen interaction | α2-I-domain-collagen interaction | α2β1-collagen interaction (4% HSA) | Static human platelet adhesion to collagen (washed plt) | Static human platelet adhesion to collagen (PRP) | Human platelet adhesion to collagen under shear (whole blood) 3000 s-1 |
|---|---|---|---|---|---|---|
| IgG4 IC50 (μg/mL) | 0.05 | 0.2 | na | 0.017 | 0.3 | na |
| IgG4 IC50 (nM) | 0.3 | 1.5 | na | 0.1 | 6.7 | na |

TABLE 9-continued

Inhibition of collagen interaction by α 2 integrin mAB

| Assay | a2β1-collagen interaction | α2-I-domain-collagen interaction | α2β1-collagen interaction (4% HSA) | Static human platelet adhesion to collagen (washed plt) | Static human platelet adhesion to collagen (PRP) | Human platelet adhesion to collagen under shear (whole blood) 3000 s-1 |
|---|---|---|---|---|---|---|
| Fab IC50 (µg/mL) | 0.2 | na | 0.4 | 0.04 | 0.3 | 0.06 |
| Fab IC50 (nM) | 4.2 | na | 8.2 | 0.8 | 6.7 | 1.3 |

In summary, α2 integrin mAB showed no effect on α1β1/collagen interaction (solid phase assay), α5β1/fibronectin interaction (solid phase assay), aIIbb3 (GPIIbIIIa) activation (FACS-assay), P-selectin expression on hu plt (FACS-assay), human platelet aggregation in whole blood alone or after stimulation with ADP, TRAP, collagen, LDH-, TNFα-, or IL1β-release from hu PBL (alone or in combination with LPS).

Huvec Tubule Length Formation

Figure 2:
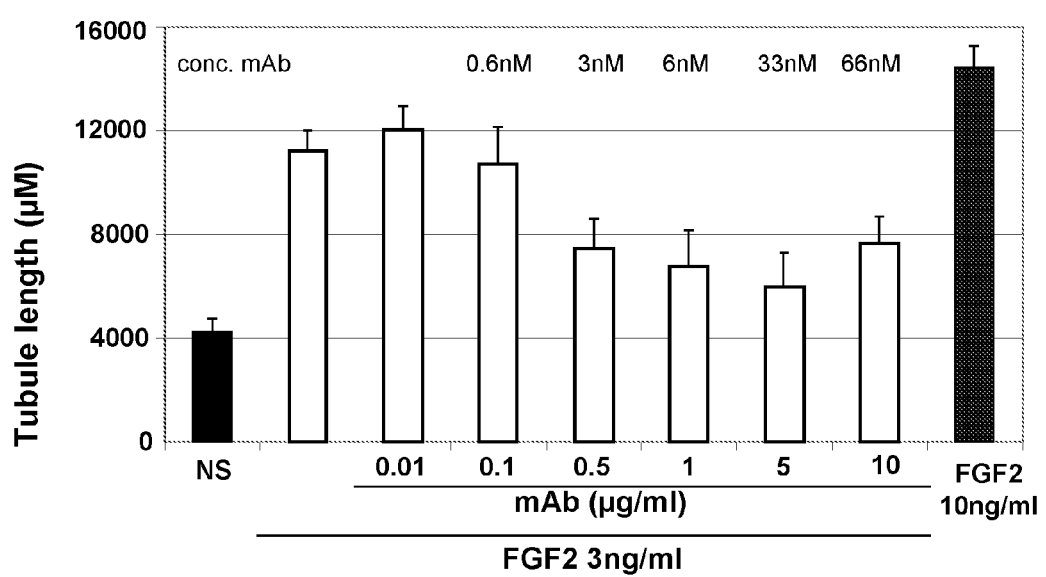

To assess the activity of the integrin anti-α2 mab in angiogenesis an in vitro assay with HUVEC cells was performed. Matrigel (BD Biosciences, #354230) was mixed with collagen type I (BD Biosciences #35429) (matrigel 1/3.25, PBS 5×1/5, collagen I 1 mg/ml, qsp water) and incubated for 1 h at 37° C., 5% CO2. The adherent HUVEC cells were carefully detached from culture flasks with Acutase solution, centrifuged and resuspended in culture medium (EBM, FCS 2%, EGF bullet kit) at 1.2 105 cells/ml. 100 µl of the cell suspension were added to the wells with the matrix in the presence or absence of serial dilutions of anti-α2 mab and FGF2 (Peptrotech, 10 ng/ml) and incubated for 18 h at 37° C., 5% CO2. For detection of tubule formation, cresyl violet solution was added and incubated for 30 min at 37° C. The tubule formation was determined by measuring the sum of the tubule length per well. Calculations were performed versus negative control (without FGF2) and positive controls (with FGF2 abut without anti-α2 mab) using Image Proand software (MediaCybernetics), measuring 6 replicates per condition. The according results are shown in FIG. 2. Anti-alphα2-Integrin mAB was able to inhibit FGF2-induced angiogenesis in a dose dependent manner.

Example 5

Inhibition of Platelet Adhesion to Collagen by Anti-α2 Integrin mAB-Fab Under Flow and Under Static Conditions For protein-protein interaction studies either recombinantly expressed integrin α2β1 integrin or the I-domain of integrin α2β1 integrin was coated to 96-well plates (Corning Costar 3690) in TBS buffer over night at 4° C. After washing off excessive protein, the plates were blocked with BSA solution (5% Sigma A7906) and washed again. Serial dilutions of α2 integrin Mab were added to the plates as well as biotinylated collagen (rat tail, Sigma C8897). This was performed in the presence or absence of 4% HSA. After an incubation of 2 h at room temperature the plates were washed again. Extravidin Peroxidase solution (Sigma E2886) was added and the plates are incubated for 20 min in the dark. Measurement was performed in an Elisa reader (SpectraMax190 Molecular Devices) at 405 nM. Percentage of inhibition and IC50s are calculated versus known standards.

For platelet binding studies to collagen, plates (Isoplate, Perkin Elmer, F1450 571) were coated with collagen (Sigma C8897) in TBS for 1 h at room temperature. The wells were washed with TBS repeatedly before serial dilutions of anti-α2 integrin MAb were added. Freshly prepared human platelet rich plasma or isolated human platelets, which were anticoagulated with hirudin, PGE1 and ReoPro and labelled with CalceinAM (C-3099 Molecular Probes were added and incubated for 90 min at room temperature protected from light. After washing, the plates were measured in an M5 reader (Molecular Devices) at 492 nM EX, 535 nM EM. Percentage of inhibition and IC50s are calculated versus known standards.

In experiments under shear, anti-α2 integrin mAB was analysed for its ability to inhibit platelet adhesion to collagen under flow. Glass capillaries were coated with collagen over night at 4° C. After washing and blocking with BSA, they were installed in a flow device. Freshly drawn anti-coagulated human blood from volunteers was labelled with DiOC6(3) and incubated for 10 min with serial dilutions of anti-α2 integrin mAB at 37° C. The samples were flown through the capillaries at a shear rate of 3000 s-1 mimicking arterial flow. After rinsing the capillaries, 10 pictures were taken representing the surface of the capillary which was in contact with the flowing blood. Using an imaging software, surface coverage was determined and percentage of inhibition and IC50s were calculated versus known standards.

For the thrombocyte adhesion assay, thrombocytes were enriched as follows: Hirudin (20 µg/ml; Refludan (Pharmion)) and blood was centrifuged at 150 g for 20 min to produce anticoagulated human blood platelet rich plasma (PRP) was collected and again centrifuged and collected as above. Platelet poor plasma was obtained from the remaining blood by centrifugation at 1940 g for 10 min (2 times). PPP was added to the diluted cells (2 mM Mg) and concentration of cells was adjusted to $2\times10^5$/µl. Cells were left for 0.5 hrs and diluted to $5\times10^4$/µl. Thereafter cells were contacted with 3 µg/ml ReoPro (2.5 µg/ml; Centocor B.V., Leiden, NL) (10 min, RT), 6 mM $MnCl_2 \times 4H_2O$ (5 mM) was added (incubation for 10 min).

Plates were prepared as follows: Plates (Perkin Elmer, IsoPlate, 1450-571) were incubated with 100 µl/well collagen Type 10 µg/ml (Type I from rat tail C8897 Sigma Stock 200 µg/ml in 0.01 M in acetic acid) at RT for 1 hr. Then, they were washed 3 times with 200 µl/well TBS (50 mM Tris-HCl pH 7.4, 120 mM NaCl, 2.7 mM KCl, 0.05 mM $CaCl_2$, 2 mM $MgCl_2 \times 6 H_2O$, 0.1% BSA. Thereafter, 10 µl/well compound and ReoPro- and Mn-treated thrombocytes ($5\times10^4$ cells/µl, 50 µl/well) were added. Cells were incubated for 1.5 hrs (darkness) and washed 3 times with 200 µl/well TBS. 2.5 µM Calcein AM (50 µl/well, C-3099, Molecular Probes, MW 994.87, 30 min, RT) was added, followed by a washing step.

The read out step was carried out using a SpectraMax M5: Fluoreszenz EX 492 EM 535 Cutoff: 530 Automatic in the absence of cells. % Inhibition is calculated as 100−((mean value compounds*100)/mean value control) after blank subtraction.

Figure 3:
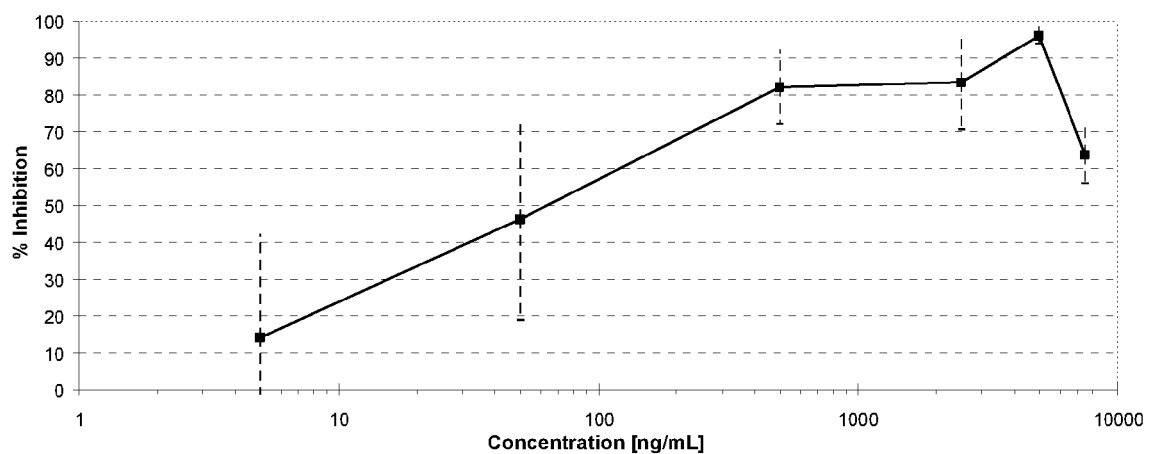
Figure 11:
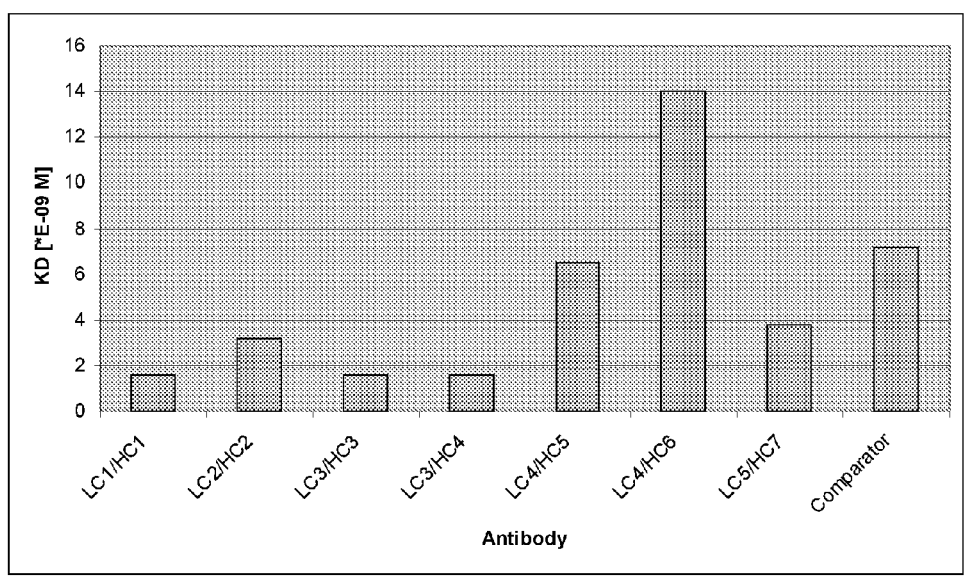
FIG. 11 shows dissociation constants of the different alpha2 integrin antibodies as determined by Biacore. The results exhibit a in many cases better or at least equal dissociation constant as the mAb TMC2206
Figure 12:
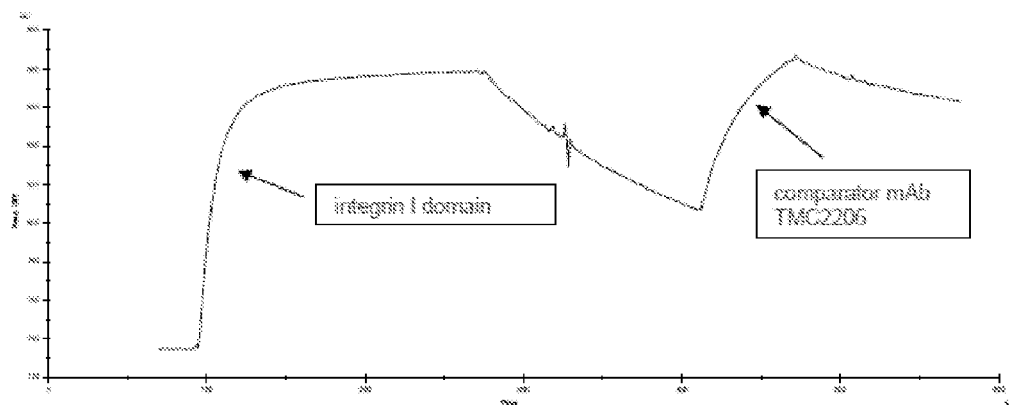
FIG. 12 shows binding of comparator mAb TMC2206 to integrin α₂ I domain pre-bound by non-humanized Fab measured using Biacore (time in (s) seconds (x-axis) versus response difference in (RU) response units (y-axis)). As can be gained from FIG. 12, TMC2206 binds to the integrin I domain pre-bound by non-humanized Fab.

As can be gained from FIG. 3, anti-α2 integrin mAB dose dependently inhibits platelet adhesion under shear stress, with a nanomolar IC50.

Example 6

Aggregation Behavior of Anti-$\alpha_2$-Integrin mAbs as Determined by Size Exclusion Chromatography All humanized variants and the comparator were tested for the aggregation percentage. Size exclusion chromatography was performed on an ÄKTA explorer 10 (GE Healthcare) using a TSKgel G3000SWXL column (7.8 mm ID×30.0 cm L, TosohBioscience) with a TSKgel SWXL guard column (TosohBioscience). 30 μl of sample at 0.4-1 mg/ml were injected and the chromatography was performed at 1 ml/min using 100 mM $Na_2SO_4$, 100 mM $Na_2HPO_4$, 0.05% $NaN_3$ pH 6.7 as running buffer and a detection wavelength of 280 nm. The column was calibrated using gel filtration molecular weight markers (Sigma Aldrich). Data evaluation was done using Unicorn software v5.11 (GE Healthcare).

TABLE 10

Aggregation percentage of anti-$\alpha_2$-integrin mAbs determined by size exclusion chromatography.

| LC/HC combination | Aggregation [%] | Peakheight [mAU] |
|---|---|---|
| LC1/HC1 | <0.5 | 74.4 |
| LC2/HC2 | <0.5 | 47.8 |
| LC3/HC3 | <0.5 | 93.7 |
| LC3/HC4 | 2.3 | 67.2 |
| LC4/HC5 | 1.8 | 67.9 |
| LC4/HC6 | <0.5 | 29.1 |
| LC5/HC7 | <0.5 | 46.5 |
| TMC2206 | 11.8 | 20.7 |

As can be gained from table 10, all tested variants of the alpha-2 integrin mAb have a low percentage of aggregates. When compared with the aggregation behavior of the comparator, all tested alpha-2 integrin antibodies exhibited lower aggregation percentage values than the comparator.

Example 7

Kinetic Binding Data of Anti-$\alpha_2$-Integrin mAbs Determined by Biacore

Surface plasmon resonance technology on a Biacore 3000 (GE Healthcare) was used for a detailed kinetic characterisation of the purified humanized antibodies. A capture assay was used with the anti-integrin antibody captured by an anti-human Fc specific antibody (MAB1302, Millipore) and the integrin $\alpha_2$ I domain was used as analyte. Typically, 120 RU of anti-integrin antibody were captured on a research grade CM5 by the immobilised anti-human Fc specific antibody, resulting in an Rmax of 30 RU for the I domain bound to the antibody. Binding kinetics were measured over a concentration range between 0.8 to 25 nM I domain in HBS-P buffer supplemented with 4 mM $MgCl_2$ (10 mM HEPES pH 7.4, 150 mM NaCl, 0.005% surfactant P20) at a flow rate of 30 μl/min. Chip surfaces were regenerated with 10 mM glycine pH 2.5. Kinetic parameters were analysed and calculated in the BIAevaluation program package (version 4.1) using a flow cell with the immobilised anti-human Fc specific antibody as reference. A 1:1 binding model with mass transfer was applied for a global fit of the data for curves corresponding to analyte concentrations from 0.8-25 nM of antibody.

Table 11). Three variants have a similar $K_D$ in Biacore as the non-humanized mAb:
  combination LC1/HC1 (Mutations addressing humanization only)
  combination LC3/HC3 (Mutations addressing humanization and stabilization)
  combination LC3/HC4 (Mutations addressing humanization and stabilization and anti-aggregation).

The variant mutation by grafting is close to the non-humanized mAb.

Example 8

Epitope Determination of Anti-Alpha 2 Integrin Antibody

In order to verify the epitope of the non-humanized anti-alpha 2 mAb with the comparator mAb, epitope characterisation was performed using surface plasmon resonance technology on a Biacore 3000 (GE Healthcare). The Fab fragment corresponding to the non-humanized anti-alpha 2 mAb was immobilized on a CM5 chip by amine reactive coupling at 500 RU. The integrin I domain was captured by the Fab fragment at 10 μl/min and after a short dissociation period, the antibody TMC2206 was allowed to bind at 30 μl/min to the $\alpha_2$ I domain. Regeneration was performed with 10 mM Glycine buffer pH 2.0. In a second experiment the comparator mAb TMC2206 was captured on a surface of anti-human Fc specific antibody (MAB 1302 Millipore).

Figure 13:
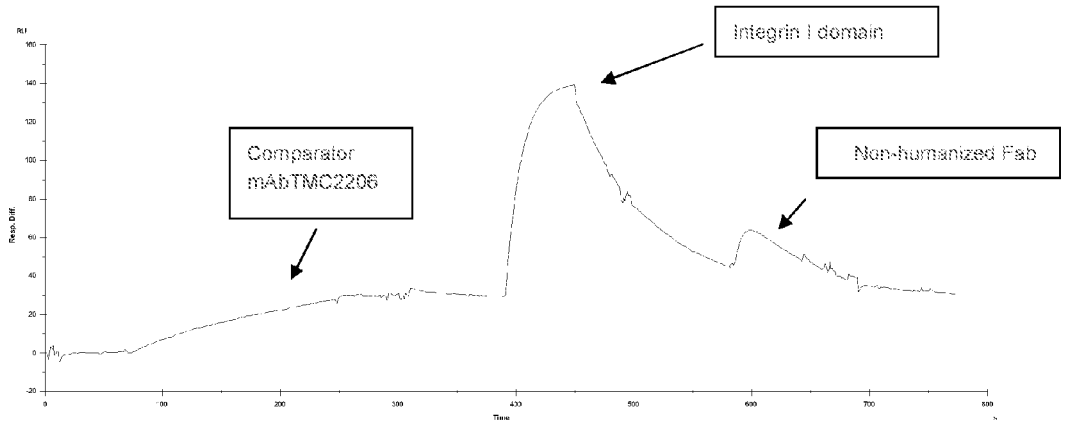
FIG. 13 shows binding of non-humanized Fab to integrin α₂ I domain pre-bound by comparator mAb TMC2206 (time in (s) seconds (x-axis) versus response difference in (RU) response units (y-axis)). As can be gained from FIG. 13, non-humanized Fab binds to the integrin α₂ I domain pre-bound by comparator mAb TMC2206.

Then the integrin I domain was bound followed by the non-humanized Fab. The results can be gained from FIGS. 13 and 14. The results clearly show that the comparator antibody, TMC2206 binds to the integrin I domain prebound by non-humanized Fab.

Thus, the non-humanized Fab binds to the integrin I domain which is pre-bound by the comparator mAb TMC2206. Simultaneous binding of the non-humanized Fab and the comparator mAb to the integrin $\alpha_2$ I domain indicates that the epitope of both the Fab and the comparator mAb are not identical. This means that the anti alpha 2 antibody of present invention and the comparator antibody bind different epitopes within alpha 2 integrin.

Example 9

Platelet Binding Assays Under Static Conditions Using Collagen-Coated Plates and Washed Platelets or Platelet-Rich Plasma As α2β1 integrin is expressed on blood platelets, playing an important role in their adhesion to collagen, an in vitro assay system for platelet binding studies using these cells was used. For platelet binding studies, plates (Isoplate, Perkin Elmer, F1450 571) were coated with collagen (Sigma C8897) in TBS for 1 h at room temperature. The wells were washed with TBS repeatedly before serial dilutions of anti-α2 integrin mAb were added. Freshly prepared human platelet rich plasma or freshly isolated human platelets, which were anti-coagulated with hirudin, PGE1 and ReoPro and labelled with CalceinAM (C-3099 Molecular Probes were added and incubated for 90 min at room temperature protected from light.

After washing, the plates were measured in an M5 reader (Molecular Devices) at 492 nM Exitation, 535 nM Emission. Percentage of inhibition and IC50s are calculated versus titration curves prepared using small molecule inhibitors of alpha-2-Integrin or the non-humanized alpha-2 mAB. The results can be gained from Table 12.

TABLE 12

Inhibition of binding of washed platelets to collagen

| LC/HC combination | IC50 µg/ml |
|---|---|
| LC1/HC1 | 0.021 |
| LC2/HC2 | 0.092 |
| LC3/HC3 | 0.012 |
| LC3/HC4 | 0.016 |
| LC4/HC5 | 0.057 |
| LC4/HC6 | 0.068 |
| LC5/HC7 | 0.031 |
| TMC2206 (comparator) | 0.023 |

As can be gained from the results shown in table 12, platelet inhibition displayed by the different anti alpha 2 antibody variants under static conditions using washed platelets is comparable to that of the comparator antibody and for some variants (LC3/HC3 or LC3/HC4) even significantly or slightly (LC1/HC1) stronger.

TABLE 13

Inhibition of binding of platelets to collagen in platelet rich plasma

| LC/HC combination | MW IC50 µg/ml |
|---|---|
| LC1/HC1 | 0.277 |
| LC2/HC2 | 3.963 |
| LC3/HC3 | 0.132 |
| LC3/HC4 | 0.193 |
| LC4/HC5 | 3.251 |
| LC4/HC6 | 4.113 |
| LC5/HC7 | 0.224 |
| TMC2206 | 0.110 |

As can be gained from the results shown in table 13, platelet inhibition displayed by the different anti alpha 2 antibody variants under static conditions using platelet-rich plasma, variants LC1/HC1, LC3/HC3, LC3/HC4 and LC5/HC7 is comparable to that of the comparator antibody.

As can be concluded from the static platelet binding assays, the humanized forms of the anti-$\alpha_2$-integrin antibody block adhesion of freshly isolated human platelets in the presence or absence of blood plasma in a concentration dependent manner. Four of the variants show a similar inhibitory activity in the bioassay as the non-humanized mAb:

combination LC1/HC1 (Mutations addressing humanization only)
  combination LC3/HC3 (Mutations addressing humanization and stabilization)
  combination LC3/HC4 (Mutations addressing humanization and stabilization and anti-aggregation)
  combination LC5/HC7 (Mutations addressing humanization by grafting)

The three variants addressing the problematic sites (NS; DS) LC2/HC2, LC4/HC5 and LC4/HC6 and showing lower platelet inhibition in the above platelet binding experiments were identical with the variants exhibiting weaker α2 I domain binding activity than not-humanized anti-alpha 2 integrin antibody in the above Biacore experiments of example 7 (see table 11). Thus, the results of the platelet binding assays are well in accordance with the affinity data from the Biacore evaluations.

Example 10

Thermal Stability of the Different Anti Alpha 2 Antibody Variants

Results with respect to thermal stability are summarized in table 14. The antibodies show comparable, equal or better thermal stability as the comparator. Thermostability measurements are performed using a PCR thermocycler (My-IQ—two in a temperature range between 10 and 90° C. with 1° C./min. Two microgram of antibody diluted in PBS buffer was supplemented with 40XSYPRO Orange (Invitrogen).

TABLE 14 thermal stability of the different variants

| LC/HC combination | Melt. Temp ° C. (1) | Melt. Temp ° C. (2) |
|---|---|---|
| LC1/HC1 | 64 | — |
| LC2/HC2 | 63 | — |
| LC3/HC3 | 64 | 68 |
| LC3/HC4 | 66 | — |
| LC4/HC5 | 62 | 67 |
| LC4/HC6 | 66 | — |
| LC5/HC7 | 65 | 72 |
| TMC2206 (comparator) | 65 | 71 |

The invention claimed is:

1. An isolated monoclonal antibody or antigen binding portion thereof, wherein said antibody or portion specifically binds to the I-domain of a human α2-integrin, said antibody comprising
(i) a light chain variable region (VL) domain comprising
   a) LCDR1, wherein LCDR1 is RASESVESYGNFSIY (SEQ ID NO: 6),
   b) LCDR2, wherein LCDR2 is LASNLAS (SEQ ID NO: 7),
   c) LCDR3, wherein LCDR3 is QQNNEDPYT (SEQ ID NO: 8), and
(ii) a heavy chain variable region (VH) domain comprising
   d) HCDR1, wherein HCDR1 is GYTFTSYWMN (SEQ ID NO: 3),
   e) HCDR2, wherein HCDR2 is RIDPSDSETHYN-QKFK (SEQ ID NO: 4), and
   f) HCDR3, wherein HCDR3 is VGRGYFDY (SEQ ID NO: 5), wherein the components a) to f) are arranged to allow for binding of said antibody or portion thereof to the I-domain of human α2-integrin.

2. The antibody, or antigen binding portion thereof, of claim 1, wherein said antibody or portion specifically binds to the I-domain of the human α2-integrin with nM binding affinity.

3. The antibody, or antigen binding portion thereof, of claim 1, wherein said antibody or portion inhibits the interaction of the human α2-integrin with collagen in vitro, thereby inhibiting the activation of platelets due to adhesion of said platelets to said collagen.

4. The antibody, or antigen binding portion thereof, of claim 1, wherein said heavy chain variable region (VH) domain comprises the sequence of SEQ ID NO:2.

5. The antibody, or antigen binding portion thereof, of claim 1, wherein said light chain variable region (VL) domain comprises the sequence of SEQ ID NO:1.

6. The antibody, or antigen binding portion thereof, of claim 1, wherein said antibody or binding portion is a chimeric antibody or humanized antibody.

7. The antibody, or antigen binding portion thereof, of claim 1, wherein the antigen binding portion is selected from the group consisting of a Fab, a Fab', a F(ab')2, a Fv, a disulfide linked Fv, a scFv, and a (scFv)$_2$.

8. The antibody, or antigen binding portion thereof, of claim 1, which is selected from the group consisting of a multispecific antibody, a dual specific antibody, a isotype antibody, a dual variable domain antibody and a bispecific antibody.

9. The antibody, or antigen binding portion thereof, of claim 1, comprising a heavy chain immunoglobulin constant domain selected from the group consisting of: a human IgM constant domain, a human IgG1 constant domain, a human IgG2 constant domain, a human IgG3 constant domain, domain, a human IgG4 constant domain, a human IgE constant domain, and a human IgA constant domain.

10. The antibody, or antigen binding portion thereof, of claim 1, comprising a human IgG4 constant domain.

11. An article of manufacture comprising
a) a packaging material, and
b) the antibody or antigen binding portion of claim 1.

12. The antibody, or antigen binding portion thereof, of claim 1, wherein said heavy chain variable region (VH) domain comprises the sequence of SEQ ID NO:2 and said light chain variable region (VL) domain comprises the sequence of SEQ ID NO:1.

13. A composition comprising the antibody, or antigen binding portion thereof, of claim 1 and one or more pharmaceutically acceptable carriers.

14. An isolated nucleic acid encoding the amino acid sequence of the antibody, or antigen binding portion thereof, of claim 1.

15. A recombinant expression vector comprising the nucleic acid of claim 14.

16. A host cell comprising the recombinant expression vector of claim 15.

17. A method of producing the antibody or antigen binding portion specifically binds to the I-domain of human α2 integrin, comprising culturing the host cell of claim 16 under conditions such that an antibody is produced by the host cell.

* * * * *